United States Patent
Birch et al.

(10) Patent No.: US 7,129,249 B2
(45) Date of Patent: Oct. 31, 2006

(54) HETEROCYCLIC AMIDE DERIVATIVES AS INHIBITORS OF GLYCOGEN PHOSHORYLASE

(75) Inventors: Alan Martin Birch, Cheshire (GB); Andrew David Morley, Cheshire (GB); Andrew Stocker, Cheshire (GB); Paul Robert Owen Whittamore, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 153 days.

(21) Appl. No.: 10/506,741

(22) PCT Filed: Mar. 4, 2003

(86) PCT No.: PCT/GB03/00877

§ 371 (c)(1), (2), (4) Date: Sep. 3, 2004

(87) PCT Pub. No.: WO03/074532

PCT Pub. Date: Sep. 12, 2003

(65) Prior Publication Data

US 2005/0131015 A1  Jun. 16, 2005

(30) Foreign Application Priority Data

Mar. 6, 2002  (GB) .................. 0205165.4

(51) Int. Cl.
A61K 31/4704 (2006.01)
A61K 31/4375 (2006.01)
C07D 215/38 (2006.01)
C07D 471/04 (2006.01)

(52) U.S. Cl. ............... 514/300; 514/312; 546/122; 546/156

(58) Field of Classification Search ............... 546/122, 546/156; 514/300, 312
See application file for complete search history.

(56) References Cited

U.S. PATENT DOCUMENTS

| | | |
|---|---|---|
| 3,706,810 A | 12/1972 | Brabander |
| 4,599,198 A | 7/1986 | Hoover |
| 4,668,769 A | 5/1987 | Hoover |
| 4,692,522 A | 9/1987 | Parsons et al. |
| 4,720,503 A | 1/1988 | Witzel |
| 4,751,231 A | 6/1988 | Halczenko |
| 4,786,641 A | 11/1988 | Goldmann |
| 4,794,120 A | 12/1988 | Manoury |
| 5,863,903 A | 1/1999 | Lundgren |
| 5,998,463 A | 12/1999 | Hulin |
| 2004/0002495 A1 | 1/2004 | Sher |
| 2004/0142938 A1 | 7/2004 | Sher et al. |
| 2004/0220229 A1 | 11/2004 | Bussolotti et al. |
| 2004/0266768 A1 | 12/2004 | Schoenafinger et al. |

FOREIGN PATENT DOCUMENTS

DE  200740  6/1983

(Continued)

(Continued)

OTHER PUBLICATIONS

Crochet, R.A., et al., "Synthesis of Substituted Thieno[2,3-b] pyrroles," vol. 11, 143-150 (Apr. 1974).

(Continued)

*Primary Examiner*—Kamal A. Saeed
*Assistant Examiner*—Jason M. Nolan

(57) ABSTRACT

Heterocyclic amides of formula (1)

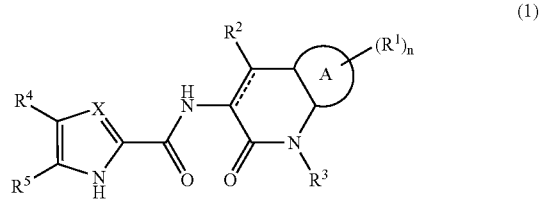

wherein:
X is N or CH;
$R^4$ and $R^5$ together are either —S—C($R^6$)=C($R^7$)— or —C($R^7$)=C($R^6$)—S—;
$R^6$ and $R^7$ are independently selected from, for example hydrogen, halo and $C_{1-4}$alkyl;
A is phenylene or heteroarylene;
n is 0, 1 or 2;
$R^1$ is selected from for example halo, nitro, cyano, hydroxy, carboxy;
$R^2$ is hydrogen, hydroxy or carboxy;
$R^3$ is selected from for example hydrogen, hydroxy, aryl, heterocyclyl and $C_{1-4}$alkyl(optionally substituted by 1 or 2 $R^8$ groups);
$R^8$ is selected from for example hydroxy, —COCOOR$^9$, —C(O)N($R^9$)($R^{10}$), —NHC(O)$R^9$, ($R^9$)($R^{10}$)N— and —COOR$^9$;
$R^9$ and $R^{10}$ are selected from for example hydrogen, hydroxy, $C_{1-4}$alkyl (optionally substituted by 1 or 2 $R^{13}$);
$R^{13}$ is selected from hydroxy, halo, trihalomethyl and $C_{1-4}$alkoxy;
or a pharmaceutically acceptable salt or pro-drug thereof; possess glycogen phosphorylase inhibitory activity and accordingly have value in the treatment of disease states associated with increased glycogen phosphorylase activity. Processes for the manufacture of said heterocyclic amide derivatives and pharmaceutical compositions containing them are described.

15 Claims, No Drawings

FOREIGN PATENT DOCUMENTS

| | | |
|---|---|---|
| DE | 4445968 | 6/1996 |
| EP | 697403 | 2/1996 |
| EP | 0846464 | 6/1998 |
| EP | 0884050 | 12/1998 |
| EP | 0978279 | 2/2000 |
| EP | 1149580 | 2/2001 |
| EP | 1177791 | 7/2001 |
| EP | 1125580 | 8/2001 |
| EP | 1134213 | 9/2001 |
| EP | 1136071 | 9/2001 |
| EP | 1 338 594 A1 | 8/2003 |
| EP | 1 340 500 A1 | 9/2003 |
| EP | 1088824 | 1/2004 |
| EP | 1145717 | 5/2004 |
| ES | 2081747 | 3/1996 |
| JP | 021247565 | 5/1990 |
| JP | 04179949 | 6/1992 |
| JP | 2001 089368 | 4/2001 |
| JP | 2001 206856 | 7/2001 |
| JP | 2001247565 | 9/2001 |
| JP | 2004196702 A | 7/2004 |
| WO | WO-93/25574 | 12/1993 |
| WO | WO-95/24391 | 9/1995 |
| WO | WO-96/39384 | 12/1996 |
| WO | WO-96/39385 | 12/1996 |
| WO | WO-97/09040 | 3/1997 |
| WO | WO-97/31901 | 9/1997 |
| WO | WO-97/45425 | 12/1997 |
| WO | WO-98/27108 | 6/1998 |
| WO | WO-98/40353 | 9/1998 |
| WO | WO-98/50359 | 11/1998 |
| WO | WO-99/26659 | 6/1999 |
| WO | WO-99/36393 | 7/1999 |
| WO | WO-00/42213 | 7/2000 |
| WO | WO-00/47206 | 8/2000 |
| WO | WO-01/05954 | 1/2001 |
| WO | WO-01/23347 | 4/2001 |
| WO | 01/32622 A1 | 5/2001 |
| WO | WO-01/32654 | 5/2001 |
| WO | WO-01/52825 | 7/2001 |
| WO | WO-01/68055 | 9/2001 |
| WO | WO-01/68092 | 9/2001 |
| WO | WO-01/68603 | 9/2001 |
| WO | WO-01/94300 | 12/2001 |
| WO | WO-01/96311 | 12/2001 |
| WO | WO-01/96347 | 12/2001 |
| WO | 02/20530 A1 | 3/2002 |
| WO | WO-02/26714 | 4/2002 |
| WO | WO-02/34718 | 5/2002 |
| WO | WO-02/080844 | 10/2002 |
| WO | WO-02/096864 | 12/2002 |
| WO | WO-02/098348 | 12/2002 |
| WO | WO-03/037864 | 5/2003 |
| WO | 03/045920 A1 | 6/2003 |
| WO | 03/072570 A1 | 9/2003 |
| WO | 03/074484 A1 | 9/2003 |
| WO | 03/074485 A2 | 9/2003 |
| WO | 03/074513 A2 | 9/2003 |
| WO | 03/074517 A1 | 9/2003 |
| WO | 03/074531 A1 | 9/2003 |
| WO | 03/091213 A1 | 11/2003 |
| WO | 2004/031193 A1 | 4/2004 |
| WO | 2004/031194 A1 | 4/2004 |
| WO | 2004/041780 A2 | 5/2004 |
| WO | 2004/092158 A1 | 10/2004 |
| WO | 2004113345 A1 | 12/2004 |
| WO | 2005/013975 A1 | 2/2005 |
| WO | 2005/013981 A1 | 2/2005 |
| WO | 2005/018637 A1 | 3/2005 |
| WO | 2005/019172 A1 | 3/2005 |
| WO | 2005/020985 A1 | 3/2005 |
| WO | 2005/020986 A1 | 3/2005 |
| WO | 2005/020987 A1 | 3/2005 |

OTHER PUBLICATIONS

Hartman, G.D., et al., "The Synthesis of 5-Alkylaminomethylthieno[2,3-b]Pyrrole-5-Sulfonamides," Heterocycles, 29(10):1943-1949 (1989).

Hoover, D.J., et al., "Indole-2-carboxamide Inhibitors of Human Liver Glycogen Phosphorylase," J. Med. Chem., 41:2934-2938 (1998).

Hudson, S., et al., "The effect of a glycogen phosphorylase inhibitor upon muscle fatigue in anaesthetised rats," J. Physiol., 539:52-53 (2002).

Jakobsen, P., et al., "Iminosugars: Potential Inhibitors of Liver Glycogen Phosphorylase.," 2001 Bioorganic Med. Chem., 9:733-744 (2001).

Martin, W.H., et al., "Discovery of a human liver glycogen phophorylase inhibitor that lowers blood glucose in vivo," PNAS, 95:1776-1781 (Feb. 1998).

McCormack, J.G., et al., "Pharmacological Approaches to Inhibit Endogenous Glucose Production as a Means of Anti-diabetic Therapy," Curr. Pharmaceutical Design, 7:1451-1474 (2001).

Oikonomakos, N.G., et al., "Allosteric inhibition of glycogen phosphorylase alpha by the potential antidiabetic drug 3-isopropyl 4-(2-chlorophenyl)-1, 4-dihydro-1-ethyl-1-methyl-pyridine-3,5,6-tricarboxylate," Protein Sci., 8:1930-1945 (1999).

Rath, V.L. et al., "Activation of Human Liver Glycogen Phosphorylase by Alteration of the Secondary Structure and Packing of the Catalytic Core," Mol. Cell, 6:139-148 (Jul. 2000).

Rosauer, K.G., et al., "Novel 3,4-Dihydroquinolin-2(1H)-one Inhibitors of Human Glycogen Phosphorylase a," Bioorganic & Medicinal Chemistry Letters, 13:4385-4388 (2003).

Soman, G., et al., "Aromatic Compounds as Allosteric Inhibitors of Glycogen Phosphorylase beta," Biochimica et Biophysica Acta, 358:359-362 (1974).

Soman, G., et al., "The Nature of the Binding Site for Aromatic Compounds in Glycogen Phosphorylase beta," Biochem. J., 147:369-371 (1975).

Treadway, J.L., et al., "Glycogen phophorlase inhibitors for treatment of type 2 diabetes mellitus," Exp. Opin. Invest. Drugs, 10(3):439-454 (2001).

Venkatarangan, P., et al., "Prediction of Ligand-REceptor Binding Thermodynamics by Free Energy Force Field Three-Dimensional Quantitative Structure-Activity Relationship Analysis: Applications to a Set of Glucose Analogue Inhibitors of Glycogen Phosphorylase," J. Med. Chem., 42:2169-2179 (1999).

Crochet, R.A., et al., J. Het. Chem., "Synthesis of Substituted Thieno[2,3-b] pyrroles," vol. 11, 143-150 (Apr. 1974).

Vertigan, H., "Impact of cell glycogen content on modulation of hepatocyte glucose metabolism by pharmacological agents," Diabetologia, 47, Supp. 1, 589, A214 (2004).

Teague, J., "Mobilisation of Tissue Glycogen Following Inhibition of Glycogen Phosphorylase in fa/fa Rat," Diabetes, 52, Supp. 2, A365, 1521-P (2003).

Font, M. et al. "Indoles and pyridazino[4,5-b]indoles as non-nucleoside analog inhibitors of HIV-1 reverse transcripptase", European Journal Med Chem (1995), 30(12), 963-71.

Vertigan, H. et al. "Impact of cell glycogen content on modulation of hepatocyte glucose metabolism by pharmacological agents", EASD Munich (2004).

Bartlett, J. et al. "In Vitro and In Vivo Profile of Gpi688, a Novel, Potent Inhibitor of Glycogen Phosphorylase", ADA San Diego (2005).

Green, A R. et al. "The Glycogenic Action of Protein Targeting to Glycogen in Hepatocytes Involves Multiple Mechanisms Including Phosphorylase and Glycogen Synthase Translocation", J Biol Chem, 279(45), 46474-46482 (2004).

Roberts, P A. et al. "The temporal relationship between glycogen phosphorylase and activation of the pyruvate dehydrogenase complex during adrenaline infusion in resting canine skeletal muscle", J Physiology-London 545(1), 297-304 (2002).

Simpson, I. et al. "Novel Orally Active Amino-indan Inhibitors of Glycogen Phosphorylase", Cambridge Med Chem Conference, (Sep. 2005). Poster EOM.

Birch, A., et al., "Novel Thienopyrrole Glycogen Phosphorylase Inhibitors: In Vitro SAR and Crystallographic Studies," Poster, Cambridge Med Chem Symposium (Sep. 2003).

Freeman, S., et al., "Effect of Glucose on Rat and Human Liver Glycogen Phosphorylasea Activity and Potency of a Glycogen Phosphoylase Inhibitor," Diabetes, 52, Supp., 1470-P, A340 (2003).

Tumbull, A., et al., "Pharmacological Inhibition of Glycogen Phosphorylase (GP) Lowers Plasma Glucose in Rat Models of Type 2 Diabetes," Dibetes, 52, Supp., 1485-P, A343 (2003).

Lin, T. et al. "Effects of Protein Binding and Experimental Disease States on Brain Uptake of Benzodiazepines in Rats", J Pharmacology & Eptl Therapeutics (1990), 253(1), 45-50.

Varnavas, A. et al. "Quinolone Derivatives: Synthesis and Binding Evaluation on Cholecystokinin Receptors", Farmaco (1996), 51(5), 341-350.

Parsons, W H. et al. "Cholecystokinin Antagonists. Synthesis and Biological Evaluation of 3-Substitued Benzolactams", J Med Chem (1989), 32(8), 1681-5.

HETEROCYCLIC AMIDE DERIVATIVES AS INHIBITORS OF GLYCOGEN PHOSHORYLASE

This application is a national stage filing under 35 U.S.C. 371 of International Application No. PCT/GB03/00877, filed Mar. 4, 2003, which claims priority from United Kingdom Patent Application No. 0205165.4, filed Mar. 6, 2002, the specification of which is incorporated by reference herein. International Application No. PCT/GB03/00877 was published under PCT Article 21(2) in English.

The present invention relates to heterocyclic amide derivatives, pharmaceutically acceptable salts and in vivo hydrolysable esters thereof. These heterocyclic amides possess glycogen phosphorylase inhibitory activity and accordingly have value in the treatment of disease states associated with increased glycogen phosphorylase activity and thus are potentially useful in methods of treatment of a warm-blooded animal such as man. The invention also relates to processes for the manufacture of said heterocyclic amide derivatives, to pharmaceutical compositions containing them and to their use in the manufacture of medicaments to inhibit glycogen phosphorylase activity in a warm-blooded animal such as man.

The liver is the major organ regulating glycaemia in the post-absorptive state. Additionally, although having a smaller role in the contribution to post-prandial blood glucose levels, the response of the liver to exogenous sources of plasma glucose is key to an ability to maintain euglycaemia. An increased hepatic glucose output (HGO) is considered to play an important role in maintaining the elevated fasting plasma glucose (FPG) levels seen in type 2 diabetics; particularly those with a FPG >140 mg/dl (7.8 mM). (Weyer et al, (1999), J Clin Invest 104: 787–794; Clore & Blackgard (1994), Diabetes 43: 256–262; De Fronzo, R. A., et al, (1992) Diabetes Care 15; 318–355; Reaven, G. M. (1995) Diabetologia 38; 3–13).

Since current oral, anti-diabetic therapies fail to bring FPG levels to within the normal, non-diabetic range and since raised FPG (and glycHbAlc) levels are risk factors for both macro—(Charles, M. A. et al (1996) Lancet 348, 1657–1658; Coutinho, M. et al (1999) Diabetes Care 22; 233–240; Shaw, J. E. et al (2000) Diabetes Care 23, 34–39) and micro-vascular disease (DCCT Research Group (1993) New. Eng. J. Med. 329; 977–986); the reduction and normalisation of elevated FPG levels remains a treatment goal in type 2 DM.

It has been estimated that, after an overnight fast, 74% of HGO was derived from glycogenolysis with the remainder derived from gluconeogenic precursors (Hellerstein et al (1997) Am J Physiol, 272: E163). Glycogen phosphorylase is a key enzyme in the generation by glycogenolysis of glucose-1-phosphate, and hence glucose in liver and also in other tissues such as muscle and neuronal tissue.

Liver glycogen phosphorylase a activity is elevated in diabetic animal models including the db/db mouse and the fa/fa rat (Aiston S et al (2000). Diabetalogia 43, 589–597).

Inhibition of hepatic glycogen phosphorylase with chloroindole inhibitors (CP91149 and CP320626) has been shown to reduce both glucagon stimulated glycogenolysis and glucose output in hepatocytes (Hoover et al (1998) J Med Chem 41, 2934–8; Martin et al (1998) PNAS 95, 1776–81). Additionally, plasma glucose concentration is reduced, in a dose related manner, db/db and ob/ob mice following treatment with these compounds.

Studies in conscious dogs with glucagon challenge in the absence and presence of another glycogen phosphorylase inhibitor, Bay K 3401, also show the potential utility of such agents where there is elevated circulating levels of glucagon, as in both Type 1 and Type 2 diabetes. In the presence of Bay R 3401, hepatic glucose output and arterial plasma glucose following a glucagon challenge were reduced significantly (Shiota et al, (1997), Am J Physiol, 273: E868).

The heterocyclic amides of the present invention possess glycogen phosphorylase inhibitory activity and accordingly are expected to be of use in the treatment of type 2 diabetes, insulin resistance, syndrome X, hyperinsulinaemia, hyperglucagonaemia, cardiac ischaemia and obesity, particularly type 2 diabetes.

According to one aspect of the present invention there is provided a compound of formula (1):

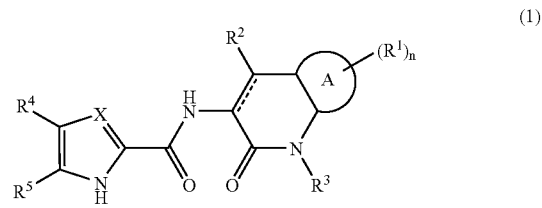

wherein:

----- is a single or double bond;

X is N or CH;

$R^4$ and $R^5$ together are either —S—C($R^6$)=C($R^7$)— or —C($R^7$)=C($R^6$)—S—;

$R^6$ and $R^7$ are independently selected from hydrogen, halo, nitro, cyano, hydroxy, fluoromethyl, difluoromethyl, trifluoromethyl, trifluoromethoxy, carboxy, carbamoyl, $C_{1-4}$alkyl, $C_{2-4}$alkenyl, $C_{2-4}$alkynyl, $C_{1-4}$alkoxy and $C_{1-4}$alkanoyl;

A is phenylene or heteroarylene;

n is 0, 1 or 2;

$R^1$ is independently selected from halo, nitro, cyano, hydroxy, carboxy, carbamoyl, N—$C_{1-4}$alkylcarbamoyl, N,N—($C_{1-4}$alkyl)$_2$carbamoyl, sulphamoyl, N—$C_{1-4}$alkylsulphamoyl, N,N—($C_{1-4}$alkyl)$_2$sulphamoyl, —S(O)$_b$$C_{1-4}$alkyl (wherein b is 0, 1, or 2), $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, hydroxy$C_{1-4}$alkyl, fluoromethyl, difluoromethyl, trifluoromethyl and trifluoromethoxy;

or, when n is 2, the two $R^1$ groups, together with the carbon atoms of A to which they are attached, may form a 4 to 7 membered ring, optionally containing 1 or 2 heteroatoms independently selected from O, S and N, and optionally being substituted by one or two methyl groups;

$R^2$ is hydrogen, hydroxy or carboxy;

$R^3$ is selected from hydrogen, hydroxy, $C_{1-4}$alkoxy, $C_{1-4}$alkanoyl, carbamoyl, $C_{3-7}$cycloalkyl (optionally substituted with 1 or 2 hydroxy groups), cyano($C_{1-4}$)alkyl, aryl, heterocyclyl, $C_{1-4}$alkyl (optionally substituted by 1 or 2 $R^8$ groups), and groups of the formulae B and B':

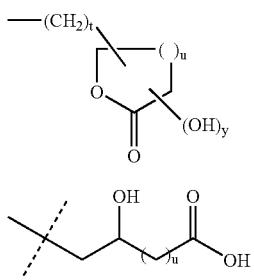

wherein y is 0 or 1, t is 0, 1, 2 or 3 and u is 1 or 2; provided that the hydroxy group is not a substituent on the ring carbon adjacent to the ring oxygen;

$R^8$ is independently selected from hydroxy, $C_{1-4}$alkoxy$C_{1-4}$alkoxy, hydroxy$C_{1-4}$alkoxy, 5- and 6-membered cyclic acetals and mono- and di-methyl derivatives thereof, aryl, heterocyclyl, $C_{3-7}$cycloalkyl, $C_{1-4}$alkanoyl, $C_{1-4}$alkoxy, $C_{1-4}$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), benzylS(O)$_b$— (wherein b is 0, 1 or 2), —N(OH)CHO, —C(=N—OH)NH$_2$, —C(=N—OH)NHC$_{1-4}$alkyl, —C(=N—OH)N(C$_{1-4}$alkyl)$_2$, —C(=N—OH)NHC$_{3-6}$cycloalkyl, —C(=N—OH)N(C$_{3-6}$cycloalkyl)$_2$, —COCOOR$^9$, —C(O)N(R$^9$)(R$^{10}$), —NHC(O)R$^9$, —C(O)NHSO$_2$(C$_{1-4}$alkyl), —NHSO$_2$R$^9$, (R$^9$)(R$^{10}$)NSO$_2$—, —COCH$_2$OR$^{11}$, (R$^9$)(R$^{10}$)N— and —COOR$^9$;

$R^9$ and $R^{10}$ are independently selected from hydrogen, hydroxy, $C_{1-4}$alkyl (optionally substituted by 1 or 2 $R^{13}$), $C_{3-7}$cycloalkyl (optionally substituted by 1 or 2 hydroxy groups), cyano(C$_{1-4}$)alkyl, trihalo(C$_{1-4}$)alkyl, aryl, heterocyclyl and heterocyclyl(C$_{1-4}$alkyl); or $R^9$ and $R^{10}$ together with the nitrogen to which they are attached form a 4- to 6-membered ring where the ring is optionally substituted on carbon by 1 or 2 substituents independently selected from oxo, hydroxy, carboxy, halo, nitro, cyano, carbonyl, $C_{1-4}$alkoxy and heterocyclyl; or the ring may be optionally substituted on two adjacent carbons by —O—CH$_2$—O— to form a cyclic acetal wherein one or both of the hydrogens of the —O—CH$_2$—O— group may be replaced by a methyl;

$R^{13}$ is selected from hydroxy, halo, trihalomethyl and $C_{1-4}$alkoxy;

$R^{11}$ is independently selected from hydrogen, $C_{1-4}$alkyl and hydroxy$C_{1-4}$alkyl;

or a pharmaceutically acceptable salt or pro-drug thereof;

with the proviso that the compound of formula (1) is not:
i) 2,3-dichloro-5-[N-(2-oxo-1,2,3,4-tetrahydroquinol-3-yl)carbamoyl]-4H-thieno[3,2-b]pyrrole;
ii) 2-chloro-5-[N-(2-oxo-1,2,3,4-tetrahydroquinol-3-yl)carbamoyl]-6H-thieno[2,3-b]pyrrole; or
iii) 2-chloro-5-[N-(1-methyl-2-oxo-1,2,3,4-tetrahydroquinol-3-yl)carbamoyl]-6H-thieno[2,3-b]pyrrole.

In another aspect is provided a compound of the formula (1):

wherein:

is a single or double bond;

X is N or CH;

$R^4$ and $R^5$ together are either —S—C(R$^6$)=C(R$^7$)— or —C(R$^7$)=C(R$^6$)—S—;

wherein $R^6$ and $R^7$ are independently selected from hydrogen, halo, nitro, cyano, hydroxy, fluoromethyl, difluoromethyl, trifluoromethyl, trifluoromethoxy, amino, carboxy, carbamoyl, mercapto, sulfamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—(C$_{1-6}$alkyl)amino, N,N—(C$_{1-6}$alkyl)$_2$amino, $C_{1-6}$alkanoylamino, N—(C$_{1-6}$alkyl)carbamoyl, N,N—(C$_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—(C$_{1-6}$alkyl)sulphamoyl, N,N—(C$_{1-6}$alkyl)$_2$sulphamoyl, $C_{1-6}$alkylsulphonylamino and $C_{1-6}$alkylsulphonyl-N—(C$_{1-6}$alkyl)amino;

wherein:
A is phenylene or heteroarylene;
n is 0, 1 or 2;
wherein $R^1$ is independently selected from hydrogen, halo, nitro, cyano, hydroxy, amino, carboxy, carbamoyl, N—C$_{1-4}$alkylcarbamoyl, N,N—(C$_{1-4}$alkyl)$_2$carbamoyl, sulphamoyl, N—C$_{1-4}$alkylsulphamoyl, N,N—(C$_{1-4}$alkyl)$_2$sulphamoyl, sulfino, sulfo, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—(C$_{1-4}$alkyl)amino,
N,N—(C$_{1-4}$alkyl)$_2$amino, hydroxyC$_{1-4}$alkyl, fluoromethyl, difluoromethyl, trifluoromethyl, trifluoromethoxy, $C_{1-4}$alkoxy and
$R^1$ is of the formula A' or A":

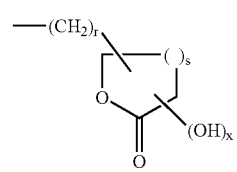

—CH$_2$CH(OH)(CH$_2$)$_u$CO$_2$H (A")

wherein x is 0 or 1, r is 0, 1, 2 or 3 and s is 1 or 2; provided that the hydroxy group is not a substituent on the ring carbon adjacent to the ring oxygen;

$R^2$ is hydrogen, hydroxy or carboxy;

$R^3$ is selected from hydrogen, hydroxy, $C_{1-4}$alkanoyl, carbamoyl, $C_{1-4}$alkyl (optionally substituted by 1 or 2 hydroxy groups provided that when there are 2 hydroxy groups they are not substituents on the same carbon), $C_{5-7}$cycloalkyl (optionally substituted with 1 or 2 hydroxy groups provided that when there are 2 hydroxy groups they are not substituents on the same carbon), cyano(C$_{1-4}$)alkyl, 4-butanolidyl, 5-pentanolidyl, tetrahydrothiopyranyl, 1-oxotetrahydrothiopyranyl, 1,1-dioxotetrahydrothiopyranyl, $C_{1-4}$alkyl [substituted by 1 or 2 $R^8$ groups (provided that when there are 2 $R^8$ groups they are not substituents on the same carbon)] and groups of the formulae B and B':

wherein y is 0 or 1, t is 0, 1, 2 or 3 and u is 1 or 2; provided that the hydroxy group is not a substituent on the ring carbon adjacent to the ring oxygen);

{wherein $R^8$ is independently selected from hydroxy, $C_{1-4}$alkoxyC$_{1-4}$alkoxy, hydroxyC$_{1-4}$alkoxy, 2,2-dimethyl-1,3-dioxolan-4-yl, heterocyclyl, $C_{1-4}$alkanoyl, $C_{1-4}$alkoxy, $C_{1-4}$alkanesulfinyl, $C_{1-4}$alkanesulfonyl, —N(OH)CHO, —COCOOR⁹, (R⁹)(R¹⁰)NCO—, (R⁹)(R¹⁰)NSO₂—, —COCH₂OR¹¹, (R⁹)(R¹⁰)N— and —COOR⁹;

[wherein $R^9$ and $R^{10}$ are independently selected from hydrogen, hydroxy, $C_{1-4}$alkyl (optionally substituted by 1 or 2 hydroxy groups provided that when there are 2 hydroxy groups they are not substituents on the same carbon), $C_{5-7}$cycloalkyl (optionally substituted by 1 or 2 hydroxy groups provided that when there are 2 hydroxy groups they are not substituents on the same carbon), cyano($C_{1-4}$)alkyl, 4-butanolidyl, 5-pentanolidyl, tetrahydrothiopyranyl, 1-oxotetrahydrothiopyranyl, 1,1-dioxotetrahydrothiopyranyl, 2,2-dimethyl-1,3-dioxolan-4-yl and $C_{1-4}$alkyl substituted by $R^{13}$;

(wherein $R^{13}$ is selected from hydroxy, $C_{1-4}$alkoxy, heterocyclyl, $C_{1-4}$alkanoyl, $C_{1-4}$alkanesulfinyl, $C_{1-4}$alkanesulfonyl, —N(OH)CHO, (R¹¹)(R¹²)NCO—, (R¹¹)(R¹²)NSO₂—, —COCH₂OR¹¹, (R¹¹)(R¹²)N—{wherein $R^{11}$ and $R^{12}$ are independently selected from hydrogen, $C_{1-4}$alkyl, $C_{1-4}$alkoxy, hydroxy$C_{1-4}$alkyl, $C_{1-4}$alkylS(O)$_b$ (wherein b is 0, 1 or 2)}); and $R^9$ and $R^{10}$ can together with the nitrogen to which they are attached form 4- to 6-membered ring where the ring is optionally substituted on carbon by 1 or 2 substituents selected from oxo, hydroxy, carboxy, halo, nitro, nitroso, cyano, isocyano, amino, N—$C_{1-4}$alkylamino, N,N—($C_{1-4}$)₂alkylamino, carbonyl, sulfo, $C_{1-4}$alkoxy, heterocyclyl, $C_{1-4}$alkanoyl, $C_{1-4}$alkanesulfinyl, $C_{1-4}$alkanesulfonyl, —N(OH)CHO, (R¹¹)(R¹²)NCO—, (R¹¹)(R¹²)NSO₂—, —COCH₂OR¹¹, (R¹¹)(R¹²)N—;

wherein $R^{11}$ and $R^{12}$ are as defined above]};

provided that when $R^1$ is of the formula A' or A" then $R^3$ does not contain a group of the formula B or B' and when $R^3$ is of the formula B or B' then $R^1$ does not contain a group of the formula A' or A";

or a pharmaceutically acceptable salt or in vivo hydrolysable ester thereof;

with the proviso that the compound of formula (1) is not:

iv) 2,3-dichloro-5-[N-(2-oxo-1,2,3,4-tetrahydroquinol-3-yl)carbamoyl]-4H-thieno[3,2-b]pyrrole;

v) 2-chloro-5-[N-(2-oxo-1,2,3,4-tetrahydroquinol-3-yl)carbamoyl]-6H-thieno[2,3-b]pyrrole; or vi) 2-chloro-5-[N-(1-methyl-2-oxo-1,2,3,4-tetrahydroquinol-3-yl)carbamoyl]-6H-thieno[2,3-b]pyrrole.

It is to be understood that when A is heteroarylene, the bridgehead atoms joining ring A to the piperidinone ring may be heteroatoms. Therefore, for example, the definition of

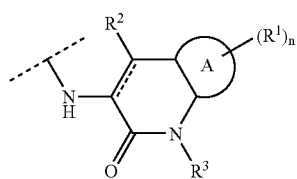

when A is heteroarylene encompasses the structures

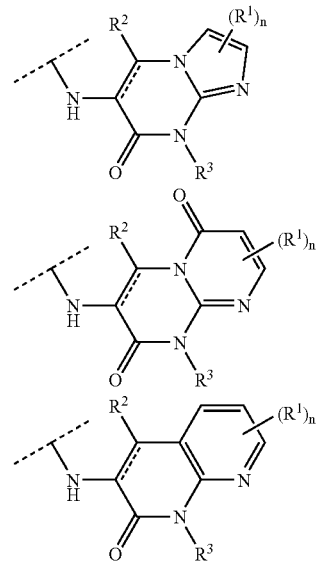

It is to be understood that, where optional substitution on alkyl or cycloalkyl groups in $R^3$, $R^9$ and $R^{10}$ (as defined hereinbefore or hereinafter) allows two hydroxy substituents on the alkyl or cycloalkyl group, or one hydroxy substituent and a second substituent linked by a heteroatom (for example alkoxy), then these two substituents are not substituents on the same carbon atom of the alkyl or cycloalkyl group.

In another aspect, the invention relates to compounds of formula (1) as hereinabove defined or to a pharmaceutically acceptable salt.

In another aspect, the invention relates to compounds of formula (1) as hereinabove defined or to a pro-drug thereof. Suitable examples of pro-drugs of compounds of formula (1) are in-vivo hydrolysable esters of compounds of formula (1). Therefore in another aspect, the invention relates to compounds of formula (1) as hereinabove defined or to an in-vivo hydrolysable ester thereof.

It is to be understood that, insofar as certain of the compounds of formula (1) defined above may exist in optically active or racemic forms by virtue of one or more asymmetric carbon atoms, the invention includes in its definition any such optically active or racemic form which possesses glycogen phosphorylase inhibition activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Within the present invention it is to be understood that a compound of the formula (1) or a salt thereof may exhibit the phenomenon of tautomerism and that the formulae drawings within this specification can represent only one of the possible tautomeric forms. It is to be understood that the invention encompasses any tautomeric form which has glycogen phosphorylase inhibition activity and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It is also to be understood that certain compounds of the formula (1) and salts thereof can exist in solvated as well as unsolvated forms such as, for example, hydrated forms. It is to be understood that the invention encompasses all such solvated forms which have glycogen phosphorylase inhibition activity.

It is also to be understood that certain compounds of the formula (1) may exhibit polymorphism, and that the invention encompasses all such forms which possess glycogen phosphorylase inhibition activity.

The present invention relates to the compounds of formula (1) as hereinbefore defined as well as to the salts thereof. Salts for use in pharmaceutical compositions will be pharmaceutically acceptable salts, but other salts may be useful in the production of the compounds of formula (1) and their pharmaceutically acceptable salts. Pharmaceutically acceptable salts of the invention may, for example, include acid addition salts of the compounds of formula (1) as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. Suitable salts include hydrochlorides, hydrobromides, phosphates, sulphates, hydrogen sulphates, alkylsulphonates, arylsulphonates, acetates, benzoates, citrates, maleates, fumarates, succinates, lactates and tartrates. In addition where the compounds of formula (1) are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

The compounds of the invention may be administered in the form of a pro-drug which is broken down in the human or animal body to give a compound of the invention. A prodrug may be used to alter or improve the physical and/or pharmacokinetic profile of the parent compound and can be formed when the parent compound contains a suitable group or substituent which can be derivatised to form a prodrug. Examples of pro-drugs include in-vivo hydrolysable esters of a compound of the invention or a pharmaceutically-acceptable salt thereof.

Various forms of prodrugs are known in the art, for examples see:
a) Design of Prodrugs, edited by H. Bundgaard, (Elsevier, 1985) and Methods in Enzymology, Vol. 42, p. 309–396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113–191 (1991);
c) H. Bundgaard, Advanced Drug Delivery Reviews, 8, 1–38 (1992);
d) H. Bundgaard, et al., Journal of Pharmaceutical Sciences, 77, 285 (1988); and
e) N. Kakeya, et al., Chem Pharm Bull, 32, 692 (1984).

An in vivo hydrolysable ester of a compound of formula (1) containing carboxy or hydroxy group is, for example a pharmaceutically acceptable ester which is cleaved in the human or animal body to produce the parent acid or alcohol.

Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

Suitable pharmaceutically-acceptable esters for hydroxy include inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include $C_{1-10}$alkanoyl, for example acetyl; benzoyl; phenylacetyl; substituted benzoyl and phenylacetyl, $C_{1-10}$alkoxycarbonyl (to give alkyl carbonate esters), for example ethoxycarbonyl; di-$(C_{1-4})$alkylcarbamoyl and N-(di-$(C_{1-4})$alkylaminoethyl)-N—$(C_{1-4})$alkylcarbamoyl (to give carbamates); di-$(C_{1-4})$alkylaminoacetyl and carboxyacetyl. Examples of ring substituents on phenylacetyl and benzoyl include aminomethyl, $(C_{1-4})$alkylaminomethyl and di-$((C_{1-4})$alkyl)aminomethyl, and morpholino or piperazino linked from a ring nitrogen atom via a methylene linking group to the 3- or 4-position of the benzoyl ring. Other interesting in-vivo hydrolysable esters include, for example, $R^AC(O)O(C_{1-6})$alkyl-CO—, wherein $R^A$ is for example, benzyloxy-$(C_{1-4})$alkyl, or phenyl). Suitable substituents on a phenyl group in such esters include, for example, 4-$(C_{1-4})$piperazino-$(C_{1-4})$alkyl, piperazino-$(C_{1-4})$alkyl and morpholino-$(C_1-C_4)$alkyl.

In this specification the generic term "alkyl" includes both straight-chain and branched-chain alkyl groups. However references to individual alkyl groups such as "propyl" are specific for the straight chain version only and references to individual branched-chain alkyl groups such as t-butyl are specific for the branched chain version only. For example, "$C_{1-4}$alkyl" includes methyl, ethyl, propyl, isopropyl and t-butyl and examples of "$C_{1-6}$alkyl" include the examples of "$C_{1-4}$alkyl" and additionally pentyl, 2,3-dimethylpropyl, 3-methylbutyl and hexyl. An analogous convention applies to other generic terms, for example "$C_{2-4}$alkenyl" includes vinyl, allyl and 1-propenyl and examples of "$C_{2-6}$alkenyl" include the examples of "$C_{2-4}$alkenyl" and additionally 1-butenyl, 2-butenyl, 3-butenyl, 2-methylbut-2-enyl, 3-methylbut-1-enyl, 1-pentenyl, 3-pentenyl and 4-hexenyl. Examples of "$C_{2-4}$alkynyl" includes ethynyl, 1-propynyl and 2-propynyl and examples of "$C_{2-6}$alkynyl" include the examples of "$C_{2-4}$alkynyl" and additionally 3-butynyl, 2-pentynyl and 1-methylpent-2-ynyl.

The term "hydroxy$C_{1-4}$alkyl" includes hydroxymethyl, hydroxyethyl, hydroxypropyl, hydroxyisopropyl and hydroxybutyl. The term "hydroxyethyl" includes 1-hydroxyethyl and 2-hydroxyethyl. The term "hydroxypropyl" includes 1-hydroxypropyl, 2-hydroxypropyl and 3-hydroxypropyl and an analogous convention applies to terms such as hydroxybutyl. The term "dihydroxy$C_{1-4}$alkyl" includes dihydroxyethyl, dihydroxypropyl, dihydroxyisopropyl and dihydroxybutyl. The term "dihydroxypropyl" includes 1,2- dihydroxypropyl and 1,3-dihydroxypropyl. An analogous convention applies to terms such as dihydroxyisopropyl and dihydroxybutyl.

The term "halo" refers to fluoro, chloro, bromo and iodo. The term "dihalo $C_{1-4}$alkyl" includes difluoromethyl and dichloromethyl. The term "trihalo $C_{1-4}$alkyl" includes trifluoromethyl.

Examples of "5- and 6-membered cyclic acetals and mono- and di-methyl derivatives thereof" are:

1,3-dioxolan-4-yl, 2-methyl-1,3-dioxolan-4-yl, 2,2-dimethyl-1,3-dioxolan-4-yl; 2,2-dimethyl-1,3-dioxan-4-yl; 2,2-dimethyl-1,3-dioxan-5-yl; 1,3-dioxan-2-yl.

Examples of "$C_{1-4}$alkoxy" include methoxy, ethoxy, propoxy and isopropoxy. Examples of "$C_{1-6}$alkoxy" include the examples of "$C_{1-4}$alkoxy" and additionally butyloxy, t-butyloxy, pentoxy and 1,2-(methyl)$_2$propoxy. Examples of "$C_{1-4}$alkanoyl" include formyl, acetyl and propionyl. Examples of "$C_{1-6}$alkanoyl" include the example of "$C_{1-4}$alkanoyl" and additionally butanoyl, pentanoyl, hexanoyl and 1,2-(methyl)$_2$propionyl. Examples of "$C_{1-4}$alkanoyloxy" are formyloxy, acetoxy and propionoxy. Examples of "$C_{1-6}$alkanoyloxy" include the examples of "$C_{1-4}$alkanoyloxy" and additionally butanoyloxy, pentanoyloxy, hexanoyloxy and 1,2-(methyl)$_2$propionyloxy. Examples of "N—($C_{1-4}$alkyl)amino" include methylamino and ethylamino. Examples of "N—($C_{1-6}$alkyl)amino" include the examples of "N—($C_{1-4}$alkyl)amino" and additionally pentylamino, hexylamino and 3-methylbutylamino. Examples of "N,N—($C_{1-4}$alkyl)$_2$amino" include N,N-(methyl)$_2$amino, N,N-(ethyl)$_2$amino and N-ethyl-N-methylamino. Examples of "N,N—($C_{1-6}$alkyl)$_2$amino" include the example of "N,N—($C_{1-4}$alkyl)$_2$amino" and additionally N-methyl-N-pentylamino and N,N-(pentyl)$_2$amino. Examples of "N—($C_{1-4}$alkyl)carbamoyl" are methylcarbamoyl and ethylcarbamoyl. Examples of "N—($C_{1-6}$alkyl)carbamoyl" are the examples of "N—($C_{1-4}$alkyl)carbamoyl" and additionally pentylcarbamoyl, hexylcarbamoyl and 1,2-(methyl)$_2$propylcarbamoyl. Examples of "N,N—($C_{1-4}$alkyl)$_2$carbamoyl" are N,N-(methyl)$_2$carbamoyl, N,N-(ethyl)$_2$carbamoyl and N-methyl-N-ethylcarbamoyl. Examples of "N,N—($C_{1-6}$alkyl)$_2$carbamoyl" are the examples of "N N—($C_{1-4}$alkyl)$_2$carbamoyl" and additionally N,N-(pentyl)$_2$carbamoyl, N-methyl-N-pentylcarbamoyl and N-ethyl-N-hexylcarbamoyl. Examples of "N—($C_{1-4}$alkyl)sulphamoyl" are N-(methyl)sulphamoyl and N-(ethyl)sulphamoyl. Examples of "N—($C_{1-6}$alkyl)sulphamoyl" are the examples of "N—($C_{1-4}$alkyl)sulphamoyl" and additionally N-pentylsulphamoyl, N-hexylsulphamoyl and 1,2-(methyl)$_2$propylsulphamoyl. Examples of "N,N—($C_{1-4}$alkyl)$_2$sulphamoyl" are N,N-(methyl)$_2$sulphamoyl, N,N-(ethyl)$_2$sulphamoyl and N-(methyl)-N-(ethyl)sulphamoyl. Examples of "N,N—($C_{1-6}$alkyl)$_2$sulphamoyl" are the examples of "N,N—($C_{1-4}$alkyl)$_2$sulphamoyl" and additionally N,N-(pentyl)$_2$sulphamoyl, N-methyl-N-pentylsulphamoyl and N-ethyl-N-hexylsulphamoyl.

Examples of "cyano($C_{1-4}$)alkyl" are cyanomethyl, cyanoethyl and cyanopropyl. Examples of "$C_{5-7}$cycloalkyl" are cyclopentyl, cyclohexyl and cycloheptyl. Examples of "$C_{3-8}$cycloalkyl" and "$C_{3-7}$cycloalkyl" include $C_{5-7}$cycloalkyl, cyclopropyl, cyclobutyl and cyclooctyl. Examples of "$C_{3-6}$cycloalkyl" inculde cyclopropyl, cyclobutyl, cyclopentyl and cyclohexyl.

The term "amino$C_{1-4}$alkyl" includes aminomethyl, aminoethyl, aminopropyl, aminoisopropyl and aminobutyl. The term "aminoethyl" includes 1-aminoethyl and 2-aminoethyl. The term "aminopropyl" includes 1-aminopropyl, 2-aminopropyl and 3-aminopropyl and an analogous convention applies to terms such as aminoethyl and aminobutyl.

The term "sulfo" means $HOSO_2$—. The term "sulfino" means $HO_2S$—.

Examples of "$C_{1-6}$alkylS(O)$_a$ (wherein a is 0 to 2)" include methylthio, ethylthio, propylthio, methanesulphinyl, ethanesulphinyl, propanesulphinyl, mesyl, ethanesulphonyl, propanesulphonyl, isopropanesulphonyl, pentanesulphonyl and hexanesulphonyl.

Examples of "$C_{1-4}$alkylS(O)$_b$ (wherein b is 0, 1 or 2)" include methylthio, ethylthio, propylthio, methanesulphinyl, ethanesulphinyl, propanesulphinyl, mesyl, ethanesulphonyl, propanesulphonyl and isopropanesulphonyl.

Examples of "$C_{3-6}$cycloalkylS(O)$_b$ (wherein b is 0, 1 or 2)" include cyclopropylthio, cyclopropylsulphinyl, cyclopropylsulphonyl, cyclobutylthio, cyclobutylsulphinyl, cyclobutylsulphonyl, cyclopentylthio, cyclopentylsulphinyl and cyclopentylsulphonyl.

Examples of "arylS(O)$_b$ (wherein b is 0, 1 or 2)" include phenylthio, phenylsulphinyl and phenylsulfonyl. Examples of "benzylS(O)$_b$ (wherein b is 0,1 or 2)" inculde benzylthio, benzylsulfinyl and benzylsulfonyl. Examples of "heterocyclylS(O)$_b$ (wherein b is 0,1 or 2)" include pyridylthio, pyridylsulfinyl, pyridylsulfonyl, imidazolylthio, imidazolylsulfinyl, imidazolylsulfonyl, pyrimidinylthio, pyrimidinylsufinyl, pyrimidinylsulfonyl, piperidylthio, piperidylsulfinyl and piperidylsulfonyl.

Examples of "$C_{1-6}$alkoxycarbonyl" include methoxycarbonyl, ethoxycarbonyl, n- and t-butoxycarbonyl. Examples of "$C_{1-6}$alkoxycarbonylamino" include methoxycarbonylamino, ethoxycarbonylamino, n- and t-butoxycarbonylamino. Examples of "$C_{1-6}$alkylsulphonyl-N—($C_{1-6}$alkyl)amino" include methylsulphonyl-N-methylamino, ethylsulphonyl-N-methylamino and propylsulphonyl-N-ethylamino. Examples of "$C_{1-6}$alkylsulphonylamino" include methylsulphonylamino, ethylsulphonylamino and propylsulphonylamino. Examples of "$C_{1-6}$alkanoylamino" include formamido, acetamido and propionylamino.

Examples of "$C_{1-4}$alkoxy$C_{1-4}$alkoxy" are methoxymethoxy, ethoxymethoxy, ethoxyethoxy and methoxyethoxy. Examples of "hydroxy$C_{1-4}$alkoxy" are hydroxyethoxy and hydroxypropoxy. Examples of "hydroxypropoxy" are 1-hydroxypropoxy, 2-hydroxypropoxy and 3-hydroxypropoxy.

Where optional substituents are chosen from "0, 1, 2 or 3" groups it is to be understood that this definition includes all substituents being chosen from one of the specified groups or the substituents being chosen from two or more of the specified groups. An analogous convention applies to substituents chose from "0, 1 or 2" groups and "1 or 2" groups.

"Heterocyclyl" is a saturated, partially saturated or unsaturated, optionally substituted monocyclic ring containing 5 to 7 atoms of which 1, 2, 3 or 4 ring atoms are chosen from nitrogen, sulphur or oxygen, which may, unless otherwise specified, be carbon or nitrogen linked, wherein a —$CH_2$— group can optionally be replaced by a —C(O)— and a ring sulphur atom may be optionally oxidised to form the S-oxide(s). Examples and suitable values of the term "heterocyclyl" are morpholino, morpholinyl, piperidino, piperidyl, pyridyl, pyranyl, pyrrolyl, imidazolyl, thiazolyl, thienyl, dioxolanyl, thiadiazolyl, piperazinyl, isothiazolidinyl, triazolyl, tetrazolyl, pyrrolidinyl, 2-oxazolidinonyl, 5-isoxazolonyl, thiomorpholino, pyrrolinyl, homopiperazinyl, 3,5-dioxapiperidinyl, 3-oxopyrazolin-5-yl, tetrahydropyranyl, tetrahydrothiopyranyl, 1-oxotetrahydrothiopyranyl, 1,1-dioxotetrahydrothiopyranyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, and oxadiazolyl.

Suitably a "heterocyclyl" is morpholino, morpholinyl, piperidino, piperidyl, pyridyl, pyranyl, pyrrolyl, imidazolyl, thiazolyl, thienyl, thiadiazolyl, piperazinyl, isothiazolidinyl, 1,3,4-triazolyl, tetrazolyl, pyrrolidinyl, thiomorpholino, pyrrolinyl, homopiperazinyl, 3,5-dioxapiperidinyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, 1,3,4-oxadiazolyl, and 1,2,4-oxadiazolyl.

Conveniently "heterocyclyl" is oxazolyl, 1,3,4-oxadiazolyl, 1,2,4-oxadiazolyl, tetrazolyl, thizoyl, thiadiazolyl, pyridyl, imidazolyl, furyl, thienyl, morpholine, pyrimidyl, pyrazinyl, pyridazinyl, pyrazolyl, pyrazolinyl, and piperazinyl.

Suitable optional substituents for "heterocyclyl" as a saturated or partially saturated ring are 1, 2 or 3 substituents independently selected from halo, cyano, hydroxy, $C_{1-4}$alkyl, $C_{1-4}$alkoxy and $C_{1-4}$alkylS(O)$_b$ (wherein b is 0, 1 or 2). Further suitable substituents for "heterocyclyl" as a saturated or partially saturated ring are 1, 2 or 3 substituents independently selected from fluoro, chloro, cyano, hydroxy, methyl, ethyl, methoxy, methylthio, methylsulfinyl and methylsulfonyl.

Suitable optional susbtituents for "heterocyclyl" as an unsaturated ring are 1, 2 or 3 substituents independently selected from halo, cyano, nitro, amino, hydroxy, $C_{1-4}$alkyl, $C_{1-4}$alkoxy, $C_{1-4}$alkylS(O)$_b$ (wherein b is 0, 1 or 2), N—($C_{1-4}$alkyl)amino and N,N—($C_{1-4}$alkyl)$_2$amino. Further suitable optional susbtituents for "heterocyclyl" as an unsaturated ring are 1, 2 or 3 substituents independently selected from fluoro, chloro, cyano, nitro, amino, methylamino, dimethylamino, hydroxy, methyl, ethyl, methoxy, methylthio, methylsulfinyl and methylsulfonyl.

Examples of "(heterocyclyl)$C_{1-4}$alkyl" are morpholinomethyl, morpholinethyl, morpholinylmethyl, morpholinylethyl, piperidinomethyl, piperidinoethyl, piperidylmethyl, piperidylethyl, imidazolylmethyl, imidazolylethyl, oxazolylmethyl, oxazolylethyl, 1,3,4-oxadiazolylmethyl, 1,2,4-oxadiazolylmethyl, 1,2,4-oxadiazolylethyl, pyridylmethyl, pyridylethyl, furylmethyl, furylethyl, (thienyl)methyl, (thienyl)ethyl, pyrazinylmethyl, pyrazinylethyl, piperazinylmethyl and piperazinylethyl.

Examples of "aryl" are optionally substituted phenyl and naphthyl.

Examples of "aryl($C_{1-4}$)alkyl" are benzyl, phenethyl, naphthylmethyl and naphthylethyl.

Suitable optional substituents for "aryl" groups are 1, 2 or 3 substituents independently selected from halo, cyano, nitro, amino, hydroxy, $C_{1-4}$alkyl, $C_{1-4}$alkoxy, $C_{1-4}$alkylS(O)$_b$ (wherein b is 0, 1 or 2), N—($C_{1-4}$alkyl)amino and N,N—($C_{1-4}$alkyl)$_2$amino. Further suitable optional susbtituents for "aryl" groups are 1, 2 or 3 substituents independently selected from fluoro, chloro, cyano, nitro, amino, methylamino, dimethylamino, hydroxy, methyl, ethyl, methoxy, methylthio, methylsulfinyl and methylsulfonyl.

"Heteroarylene" is a diradical of a heteroaryl group. A heteroaryl group is an aryl, monocyclic ring containing 5 to 7 atoms of which 1, 2, 3 or 4 ring atoms are chosen from nitrogen, sulphur or oxygen. Examples of heteroarylene are oxazolylene, oxadiazolylene, pyridylene, pyrimidinylene, imidazolylene, triazolylene, tetrazolylene, pyrazinylene, pyridazinylene, pyrrolylene, thienylene and furylene.

Suitable optional substituents for heteroaryl groups, unless otherwise defined, are 1, 2 or 3 substituents independently selected from halo, cyano, nitro, amino, hydroxy, $C_{1-4}$alkyl, $C_{1-4}$alkoxy, $C_{1-4}$alkylS(O)$_b$ (wherein b is 0, 1 or 2), N—($C_{1-4}$alkyl)amino and N,N—($C_{1-4}$alkyl)$_2$amino. Further suitable optional susbtituents for "heteroaryl" groups are 1, 2 or 3 substituents independently selected from fluoro, chloro, cyano, nitro, amino, methylamino, dimethylamino, hydroxy, methyl, ethyl, methoxy, methylthio, methylsulfinyl and methylsulfonyl.

Preferred values of A, $R^1$, $R^2$, $R^3$, $R^4$, $R^5$ and n are as follows. Such values may be used where appropriate with any of the definitions, claims, aspects or embodiments defined hereinbefore or hereinafter.

In one embodiment of the invention are provided compounds of formula (1), in an alternative embodiment are provided pharmaceutically-acceptable salts of compounds of formula (1), in a further alternative embodiment are provided in-vivo hydrolysable esters of compounds of formula (1), and in a further alternative embodiment are provided pharmaceutically-acceptable salts of in-vivo hydrolysable esters of compounds of formula (1).

In one aspect of the present invention there is provided a compound of formula (1) as depicted above wherein $R^4$ and $R^5$ are together —S—C($R^6$)=C($R^7$)—.

In another aspect of the invention $R^4$ and $R^5$ are together —C($R^7$)=C($R^6$)—S—.

In a further aspect of the invention, $R^6$ and $R^7$ are independently selected from hydrogen, halo or $C_{1-6}$alkyl.

Preferably $R^6$ and $R^7$ are independently selected from hydrogen, chloro, bromo or methyl.

Particularly $R^6$ and $R^7$ are independently selected from hydrogen or chloro.

More particularly one of $R^6$ and $R^7$ is chloro.

In one embodiment, one of $R^6$ and $R^7$ is chloro and the other is hydrogen.

In another embodiment, both $R^6$ and $R^7$ are chloro.

In one aspect of the invention A is phenylene.

In another aspect of the invention A is heteroarylene.

Preferably A is selected from phenylene, pyridylene, pyrimidinylene, pyrrolylene, imidazolylene, triazolylene, tetrazolylene, oxazolylene, oxadiazolylene, thienylene and furylene.

In one aspect of the invention n is 0 or 1.

In one aspect preferably n is 1.

In another aspect, preferably n is 0.

When n is 2, and the two $R^1$ groups, together with the carbon atoms of A to which they are attached, form a 4 to 7 membered ring, optionally containing 1 or 2 heteroatoms independently selected from O, S and N, conveniently such a ring is a 5 or 6 membered ring containing two O atoms (ie a cyclic acetal). When the two $R^1$ groups together form such a cyclic acetal, preferably it is not substituted. Most preferably the two $R^1$ groups together are the group —O—CH$_2$—O—.

In another aspect of the present invention $R^1$ is selected from halo, nitro, cyano, hydroxy, fluoromethyl, difluoromethyl, trifluoromethyl and $C_{1-4}$alkoxy.

In a further aspect $R^1$ is selected from halo, nitro, cyano, hydroxy, fluoromethyl, difluoromethyl, trifluoromethyl, —S(O)$_b$C$_{1-4}$alkyl (wherein b is 0, 1 or 2), $C_{1-4}$alkyl and $C_{1-4}$alkoxy.

In a further aspect $R^1$ is selected from halo, nitro, cyano, hydroxy, fluoromethyl, difluoromethyl, trifluoromethyl, —S(O)$_b$Me (wherein b is 0, 1 or 2), methyl and methoxy.

In a further aspect, $R^1$ is $C_{1-4}$alkyl.

Preferably $R^1$ is selected from halo and $C_{1-4}$alkoxy.

In another embodiment preferably $R^1$ is selected from fluoro, chloro, methyl, ethyl, methoxy and —O—CH$_2$—O—.

In one aspect of the invention

----- is a single bond.

In another aspect of the invention

----- is a double bond.

In one aspect of the invention $R^2$ is hydrogen. In another aspect of the invention $R^2$ is carboxy. In another aspect of the invention $R^2$ is hydroxy.

Preferably $R^2$ is hydrogen.

Suitable values for $R^3$ as heterocyclyl are morpholino, morpholinyl, piperidino, piperidyl, pyridyl, pyranyl, pyrrolyl, imidazolyl, thiazolyl, thienyl, thiadiazolyl, piperazinyl, isothiazolidinyl, 1,3,4-triazolyl, tetrazolyl, pyrrolidinyl, thiomorpholino, pyrrolinyl, homopiperazinyl, 3,5-dioxapiperidinyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, 1,3,4-oxadiazolyl, and 1,2,4-oxadiazolyl, tetrahydrothiopyranyl, 1-oxotetrahydrothiopyranyl, 1,1-dioxotetrahydrothiopyranyl.

More suitable values for $R^3$ as heterocyclyl are pyridyl, pyrimidinyl and imidazolyl.

Further suitable values for $R^3$ as heterocyclyl are tetrahydrothiopyranyl, 1-oxotetrahydrothiopyranyl, 1,1-dioxotetrahydrothiopyranyl.

In one aspect of the invention $R^3$ is selected from hydrogen, hydroxy, $C_{1-4}$alkoxy, $C_{1-4}$alkanoyl, carbamoyl, $C_{3-7}$cycloalkyl (optionally substituted with 1 or 2 hydroxy groups, cyano($C_{1-4}$)alkyl, morpholino, morpholinyl, piperidino, piperidyl, pyridyl, pyranyl, pyrrolyl, imidazolyl, thiazolyl, thienyl, thiadiazolyl, piperazinyl, isothiazolidinyl, 1,3,4-triazolyl, tetrazolyl, pyrrolidinyl, thiomorpholino, pyrrolinyl, homopiperazinyl, 3,5-dioxapiperidinyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, 1,3,4-oxadiazolyl, and 1,2,4-oxadiazolyl, tetrahydrothiopyranyl, 1-oxotetrahydrothiopyranyl, 1,1-dioxotetrahydrothiopyranyl and $C_{1-4}$alkyl (optionally substituted by 1 or 2 $R^8$ groups);

$R^9$ and $R^{10}$ are independently selected from hydrogen, hydroxy, $C_{1-4}$alkyl (optionally substituted by 1 or 2 $R^{13}$ groups), $C_{3-7}$cycloalkyl (optionally substituted by 1 or 2 hydroxy groups), cyano($C_{1-4}$)alkyl, trihalo $C_{1-4}$alkyl, aryl, heterocyclyl and heterocyclyl($C_{1-4}$alkyl);

or $R^9$ and $R^{10}$ together with the nitrogen to which they are attached form a 4- to 6-membered ring where the ring is optionally substituted on carbon by 1 or 2 substituents selected from oxo, hydroxy, carboxy, halo, nitro, cyano, carbonyl and $C_{1-4}$alkoxy, or the ring may be optionally substituted on two adjacent carbons by —O—$CH_2$—O— to form a cyclic acetal wherein one or both of the hydrogens of the —O—$CH_2$—O— group may be replaced by a methyl;

$R^8$ is independently selected from hydroxy, $C_{1-4}$alkoxy$C_{1-4}$alkoxy, hydroxy$C_{1-4}$alkoxy, 5- and 6-membered cyclic acetals and mono- and di-methyl derivatives thereof, aryl, heterocyclyl, $C_{3-7}$cycloalkyl, $C_{1-4}$alkanoyl, $C_{1-4}$alkoxy, $C_{1-4}$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), benzylS(O)$_b$— (wherein b is 0, 1 or 2), —N(OH)CHO, —C(=N—OH)NH$_2$, —C(=N—OH)NHC$_{1-4}$alkyl, —C(=N—OH)N(C$_{1-4}$alkyl)$_2$, —C(=N—OH)NHC$_{3-6}$cycloalkyl, —C(=N—OH)N(C$_{3-6}$cycloalkyl)$_2$, —CO-COOR$^9$, —C(O)N(R$^9$)(R$^{10}$), —NHC(O)R$^9$, —C(O)NHSO$_2$(C$_{1-4}$alkyl), —NHSO$_2$R$^9$, (R$^9$)(R$^{10}$)NSO$_2$—, —COCH$_2$OR$^{11}$, (R$^9$)(R$^{10}$)N— and —COOR$^9$;

$R^{13}$ is selected from hydroxy, halo, trifluoromethyl and $C_{1-4}$alkoxy;

$R^{11}$ is selected from hydrogen, $C_{1-4}$alkyl and hydroxy$C_{1-4}$alkyl.

In a further aspect of the invention $R^3$ is selected from cyano$C_{1-4}$alkyl and $C_{1-4}$alkyl (optionally substituted by 1 or 2 of $R^8$ groups);

$R^8$ is independently selected from hydroxy, phenyl, 2,2-dimethyl-1,3-dioxolan-4-yl; 2,2-dimethyl-1,3-dioxan-4-yl; 2,2-dimethyl-1,3-dioxan-5-yl, 1,2,4-oxadiazolyl, 1,3,4-oxadiazolyl, triazolyl, tetrazolyl, imidazolyl, pyrrolidinyl, piperidyl, tetrahydrofuryl, tetrahydropyranyl, tetrahydrothiopyranyl and tetrahydrothienyl, $C_{1-4}$alkoxy, $C_{1-4}$alkanoyl, $C_{1-4}$alkylS(O)$_b$— (wherein b is 0, 1 or 2), —C(O)N(R$^9$)(R$^{10}$), —COOR$^9$, —C(O)NHSO$_2$Me, —C(=N—OH)NH$_2$, —C(=N—OH)NHC$_{1-4}$alkyl, —C(=N—OH)N(C$_{1-4}$alkyl)$_2$ and —NHSO$_2$R$^9$;

$R^9$ and $R^{10}$ are independently selected from hydrogen, hydroxy, $C_{1-4}$alkyl optionally substituted with $R^{13}$ (wherein $R^{13}$ is $C_{1-4}$alkoxy or hydroxy); or $R^9$ and $R^{10}$ together with the nitrogen to which they are attached form a 4- to 6-membered ring where the ring may be optionally substituted on carbon by 1 or 2 hydroxy groups or carboxy groups), or the ring may be optionally substituted on two adjacent carbons by —O—$CH_2$—O— to form a cyclic acetal wherein one or both of the hydrogens of the —O—$CH_2$—O— group may be replaced by a methyl.

In a further aspect of the invention $R^3$ is selected from cyano$C_{1-4}$alkyl and $C_{1-4}$alkyl (optionally substituted by 1 or 2 $R^8$ groups);

$R^8$ is independently selected from hydroxy, 2,2-dimethyl-1,3-dioxolan-4-yl, 1,2,4-oxadiazolyl, 1,3,4-oxadiazolyl, tetrazolyl, $C_{1-4}$alkoxy, $C_{1-4}$alkanoyl, $C_{1-4}$alkylS(O)$_b$— (wherein b is 0, 1 or 2), —C(O)N(R$^9$)(R$^{10}$), —COOR$^9$, —C(O)NHSO$_2$Me, —C(=N—OH)NH$_2$;

$R^9$ and $R^{10}$ are independently selected from hydrogen, hydroxy, $C_{1-4}$alkyl optionally substituted with $R^{13}$ (wherein $R^{13}$ is $C_{1-4}$alkoxy or hydroxy); or $R^9$ and $R^{10}$ together with the nitrogen to which they are attached form a 4- to 6-membered ring selected from piperidine, 4-hydroxy piperidine, pyrrolidine, 3,4-dihydroxypyrrolidine and the dimethylacetal of 3,4-dihydroxypyrrolidine.

In yet a further aspect of the invention $R^3$ is selected from hydroxypropyl, 2-hydroxybutyl, 3-hydroxy-2-hydroxymethyl-propyl, 2,3-dihydroxypropyl, 1,3-dihydroxyprop-2-yl, (2,2-dimethyl-1,3-dioxolan-4-yl)methyl, (2,2-dimethyl-1,3-dioxan-4-yl)methyl, (2,2-dimethyl-1,3-dioxan-5-yl)methyl, (2-oxo-1,3-dioxan-5-yl)methyl, cyanomethyl, butanoyl, methoxyethyl, (3-hydroxypiperidino)carbonylmethyl, 1,2,4-oxadiazolylmethyl, (5-oxo)-1,2,4-oxadiazolylmethyl, (5-methyl)-1,2,4-oxadiazolylmethyl, (2-amino)-1,3,4-oxadiazolylmethyl, tetrazolylmethyl, (3,4-dihydroxypyrrolidinyl)carbonylmethyl, [(3,4-dihydroxypyrrolidinyl)carbonylmethyl]dimethylacetal, methylthioethyl, methanesulfinylethyl, methanesulfonylethyl, N-methanesulfonamidocarbonylmethyl, N-methanesulfonamidocarbonylethyl, N-(1,3-dihydroxyprop-2-yl)carbamoylmethyl, 2-(dimethylamino)ethyl, 2-hydroxy-3-(dimethylamino)propyl, amino(N-hydroxy)iminomethyl, methoxycarbonylmethyl, hydroxymethylcarbonylmethyl, carboxymethyl, carbamoylmethyl, (dimethylcarbamoyl)methyl, (methylcarbamoyl)methyl, (methylcarbamoyl)ethyl, (hydroxycarbamoyl)methyl, (hydroxyethylcarbamoyl)methyl, and (methoxyethylcarbamoyl)methyl, acetylaminoethyl, trifluoroacetylaminoethyl, N-(pyrid-4-yl)carbamoylmethyl, N-(pyrid-2-yl)carbamoylmethyl, N-(3-methyl-pyrid-2-yl)carbamoylmethyl, N-(6-methyl-pyrid-2-yl)carbamoylmethyl, N-(3-hydroxy-pyrid-2-yl)carbamoylmethyl, N-(6-fluoro-pyrid-2-yl)carbamoylmethyl, N-(6-bromo-pyrid-2-yl)carbamoylmethyl, N-(6-fluoro-pyrid-3-yl)carbamoylmethyl, N-(6-chloro-pyrid-3-yl)carbamoylmethyl, N-(N-methyl-imidazol-3-yl)carbamoylmethyl, N-(imidazol-2-ylmethyl)carbamoylmethyl, N-(tetrazol-5-ylmethyl)carbamoylmethyl, N-(4-methyl-thiazol-2-yl)carbamoylmethyl, N-(1,3,4-thiadiazol-2-yl)carbamoylmethyl, N-(5-methyl-1,3,4-thiadiazol-2-yl)carbamoylmethyl, N-(5-ethyl-1,3,4-thiadiazol-2-yl)carbamoylmethyl, N-(4-cyano-pyridazin-3-yl)carbamoylmethyl, N-(6-chloro-pyridazin-3-yl)carbamoylmethyl, N-(2,4-dimethyl-2H-pyridazin-3-yl)carbamoylmethyl, N-(2-ethyl-2H-pyridazin-3-yl)carbamoylmethyl, N-(pyrazin-2-ylmethyl)carbamoylmethyl, N-(pyrimidin-4-yl)carbamoylmethyl, N-(2-hydroxy-pyrimidin-4-yl)carbamoylmethyl, N-(4-hydroxy-pyrimidin-2-yl)carbamoylmethyl, N-(N-methylpyrazol-3-yl)carbamoylmethyl, N-(5-ethylpyrazol-3-yl)carbamoylmethyl and N-(5-oxo-2H-pyrazol-3-yl)carbamoylmethyl.

In yet a further aspect of the invention $R^3$ is selected from hydrogen, hydroxyethyl, hydroxypropyl, 2-hydroxybutyl, 3-hydroxy-2-hydroxymethyl-propyl, 2,3-dihydroxypropyl, (2,2-dimethyl-1,3-dioxolan-4-yl)methyl, (2,2-dimethyl-1,3-dioxan-4-yl)methyl, (2,2-dimethyl-1,3-dioxan-5-yl)methyl, (2-oxo-1,3-dioxan-5-yl)methyl, cyanomethyl, butanoyl, methoxyethyl, (3-hydroxypiperidino)carbonylmethyl, 1,2,4-oxadiazolylmethyl, (5-oxo)-1,2,4-oxadiazolylmethyl, (5-methyl)-1,2,4-oxadiazolylmethyl, (2-amino)-1,3,4-oxadiazolylmethyl, tetrazolylmethyl, (3,4-dihydroxypyrrolidinyl)carbonylmethyl, [(3,4-dihydroxypyrrolidinyl)carbonylmethyl]dimethylacetal, methylthioethyl, methanesulfinylethyl, methanesulfonylethyl, N-methanesulfonamidocarbonylmethyl, N-(1,3-dihydroxyprop-2-yl)carbamoylmethyl, 2-(dimethylamino)ethyl, 2-hydroxy-3-(dimethylamino)propyl, amino(N-hydroxy)iminomethyl, methoxycarbonylmethyl, carboxymethyl, carbamoylmethyl, (dimethylcarbamoyl)methyl, (methylcarbamoyl)methyl, (methylcarbamoyl)ethyl, (hydroxycarbamoyl)methyl, (hydroxyethylcarbamoyl)methyl, and (methoxyethylcarbamoyl)methyl.

In yet a further aspect of the invention $R^3$ is selected from hydrogen, hydroxyethyl, hydroxypropyl, 2-hydroxybutyl, 3-hydroxy-2-hydroxymethyl-propyl, 2,3-dihydroxypropyl, carbamoylmethyl, (dimethylcarbamoyl)methyl, (methylcarbamoyl)methyl, (methylcarbamoyl)ethyl, (hydroxycarbamoyl)methyl, (hydroxyethylcarbamoyl)methyl, (methoxyethylcarbamoyl)methyl, amino(N-hydroxy)iminomethyl, methanesulfinylethyl, and methanesulfonylethyl.

In one aspect, one of $R^9$ and $R^{10}$ is hydrogen and the other is selected from heterocyclyl and heterocyclyl($C_{1-4}$alkyl). Conveniently $R^9$ or $R^{10}$ as heterocyclyl and heterocyclyl($C_{1-4}$alkyl) is selected from oxazolyl, 1,3,4-oxadiazolyl, 1,2,4-oxadiazolyl, tetrazolyl, thiazoyl, thiadiazolyl, pyridyl, imidazolyl, furyl, thienyl, morpholine, pyrimidyl, pyrazinyl, pyridazinyl, pyrazolyl, pyrazolinyl, piperazinyl, morpholinomethyl, morpholinethyl, morpholinylmethyl, morpholinylethyl, piperidinomethyl, piperidinoethyl, piperidylmethyl, piperidylethyl, tetrahydrothiopyranyl, 1-oxotetrahydrothiopyranyl, 1,1-dioxotetrahydrothiopyranyl, imidazolylmethyl, imidazolylethyl, oxazolylmethyl, oxazolylethyl, 1,3,4-oxadiazolylmethyl, 1,2,4-oxadiazolylmethyl, 1,2,4-oxadiazolylethyl, pyridylmethyl, pyridylethyl, furylmethyl, furylethyl, (thienyl)methyl, (thienyl)ethyl, pyrazinylmethyl, pyrazinylethyl, piperazinylmethyl and piperazinylethyl; wherein the heterocylic ring is optional substituted on any available atom by 1, 2 or 3 substituents independently selected from halo, cyano, hydroxy, $C_{1-4}$alkyl, $C_{1-4}$alkoxy and $C_{1-4}$alkylS(O)$_b$ (wherein b is 0, 1 or 2), and additionally when the heterocyclyl ring is a heteroaryl ring, further suitable optional substituents are selected from nitro, amino, N—($C_{1-4}$alkyl)amino and N,N—($C_{1-4}$alkyl)$_2$amino, and/or wherein any heterocyclic ring is optionally oxidised such that a —CH$_2$— group is replaced by a —C(O)— and/or a ring sulphur atom is oxidised to form the S-oxide(s).

A preferred class of compound is of the formula (1) wherein;

----- is a single bond;
X is CH;
$R^4$ and $R^5$ are together —C($R^7$)=C($R^6$)—S—;
$R^6$ is halo;
$R^7$ is hydrogen;
A is phenylene;
n is 0, 1 or 2;
$R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
$R^2$ is hydrogen;
$R^3$ is selected from cyano$C_{1-4}$alkyl, and $C_{1-4}$alkyl (optionally substituted by 1 or 2 $R^8$ groups);
$R^8$ is independently selected from hydroxy, $C_{3-7}$cycloalkyl, phenyl, 2,2-dimethyl-1,3-dioxolan-4-yl; 2,2-dimethyl-1,3-dioxan-4-yl; 2,2-dimethyl-1,3-dioxan-5-yl, 1,2,4-oxadiazolyl, 1,3,4-oxadiazolyl, triazolyl, tetrazolyl, imidazolyl, pyrrolidinyl, piperidyl, tetrahydrofuryl, tetrahydropyranyl, tetrahydrothiopyranyl and tetrahydrothienyl, $C_{1-4}$alkoxy, $C_{1-4}$alkanoyl, $C_{1-4}$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), —C(O)N($R^9$)($R^{10}$), —COOR$^9$, —C(O)NHSO$_2$Me, —C(=N—OH)NH$_2$, —C(=N—OH)NHC$_{1-4}$alkyl, —C(=N—OH)N($C_{1-4}$alkyl)$_2$—N(OH)CHO, —COCOOR$^9$, —NHC(O)R$^9$, ($R^9$)($R^{10}$)NSO$_2$—, —COCH$^2$OR$^{11}$ and —NHSO$_2$R$^9$;

$R^9$ and $R^{10}$ are independently selected from hydrogen, hydroxy, phenyl, heterocyclyl, heterocyclyl($C_{1-4}$alkyl), $C_{1-4}$alkyl (optionally substituted by 1 or 2 hydroxy groups) and $C_{1-4}$alkyl substituted by $C_{1-4}$alkoxy, and wherein $R^9$ and $R^{10}$ can together with the nitrogen to which they are attached form 4- to 6-membered ring where the ring is optionally substituted on carbon by 1 or 2 substituents selected from hydroxy or carboxy, or the ring may be optionally substituted on two adjacent carbons by —O—CH$_2$—O— to form a cyclic acetal wherein one or both of the hydrogens of the —O—CH$_2$—O— group may be replaced by a methyl;

R$^{11}$ is selected from hydrogen, C$_{1-4}$alkyl and hydroxyC$_{1-4}$alkyl;

or a pharmaceutically acceptable salt or in vivo hydrolysable ester thereof;

with the proviso that the compound of formula (1) is not
i. 2-chloro-5-[N-(1-methyl-2-oxo-1,2,3,4-tetrahydroquinol-3-yl)carbamoyl]-6H-thieno[2,3-b]pyrrole.

Another preferred class of compounds is of formula (1) wherein:

----- is a single bond;
X is CH;
R$^4$ and R$^5$ are together —C(R$^7$)=C(R$^6$)—S—;
R$^6$ is chloro;
R$^7$ is hydrogen;
A is phenylene;
n is 0, 1 or 2;
R$^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
R$^2$ is hydrogen;
R$^3$ is selected from C$_{1-4}$alkyl (optionally substituted by 1 or 2 R$^8$ groups);
R$^8$ is independently selected from hydroxy, phenyl, 2,2-dimethyl-1,3-dioxolan-4-yl; 2,2-dimethyl-1,3-dioxan-4-yl; 2,2-dimethyl-1,3-dioxan-5-yl, 1,2,4-oxadiazolyl, 1,3,4-oxadiazolyl, triazolyl, tetrazolyl, imidazolyl, pyrrolidinyl, piperidyl, tetrahydrofuryl, tetrahydropyranyl, tetrahydrothiopyranyl and tetrahydrothienyl, C$_{1-4}$alkoxy, C$_{1-4}$alkanoyl, C$_{1-4}$alkylS(O)$_b$— (wherein b is 0, 1 or 2), C$_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), —C(O)N(R$^9$)(R$^{10}$), —COOR$^9$, —C(O)NHSO$_2$Me, —C(=N—OH)NH$_2$, —C(=N—OH)NHC$_{1-4}$alkyl, —C(=N—OH)N(C$_{1-4}$alkyl)$_2$ and —NHSO$_2$R$^9$;
R$^9$ and R$^{10}$ are independently selected from hydrogen, hydroxy, phenyl, heterocyclyl, heterocyclyl(C$_{1-4}$alkyl), C$_{1-4}$alkyl (optionally substituted by 1 or 2 hydroxy groups) and C$_{1-4}$alkyl substituted by C$_{1-4}$alkoxy, and wherein R$^9$ and R$^{10}$ together with the nitrogen to which they are attached form a 4- to 6-membered ring selected from piperidine, 4-hydroxy piperidine, pyrrolidine, 3,4-dihydroxypyrrolidine and the dimethylacetal of 3,4-dihydroxypyrrolidine;

or a pharmaceutically acceptable salt or in vivo hydrolysable ester thereof;

with the proviso that the compound of formula (1) is not:
i. 2-chloro-5-[N-(1-methyl-2-oxo-1,2,3,4-tetrahydroquinol-3-yl)carbamoyl]-6H-thieno[2,3-b]pyrrole.

Another preferred class of compounds is of formula (1) wherein:

----- is a single bond;
X is CH;
R$^4$ and R$^5$ are together —C(R$^7$)=C(R$^6$)—S— or —S—C(R$^6$)=C(R$^7$)—;
R$^6$ is hydrogen or chloro;
R$^7$ is hydrogen or chloro;
A is phenylene;
n is 0;
R$^2$ is hydrogen;
R$^3$ is selected from C$_{1-4}$alkyl (optionally substituted by 1 or 2 R$^8$ groups);
R$^8$ is independently selected from hydroxy, C$_{1-4}$alkylS(O)$_b$— (wherein b is 0, 1 or 2), —NHC(O)R$^9$ and —C(O)N(R$^9$)(R$^{10}$);
R$^9$ and R$^{10}$ are independently selected from hydrogen, C$_{1-4}$alkyl (optionally substituted by 1 or 2 hydroxy groups) and C$_{1-4}$alkyl substituted by C$_{1-4}$alkoxy;

or a pharmaceutically acceptable salt or in vivo hydrolysable ester thereof;

with the proviso that the compound of formula (1) is not:
i 2-chloro-5-[N-(1-methyl-2-oxo-1,2,3,4-tetrahydroquinol-3-yl)carbamoyl]-6H-thieno[2,3-b]pyrrole.

Another preferred class of compounds is of formula (1) wherein:

----- is a single bond;
X is CH;
R$^4$ and R$^5$ are together —C(R$^7$)=C(R$^6$)—S—;
R$^6$ is chloro;
R$^7$ is hydrogen;
A is phenylene;
n is 0, 1 or 2;
R$^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
R$^2$ is hydrogen;
R$^3$ is selected from groups of the formulae B and B':

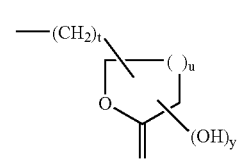

(B)

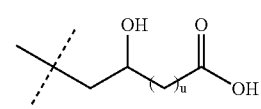

(B')

wherein y is 0 or 1, t is 0, 1, 2 or 3 and u is 1 or 2; provided that the hydroxy group is not a substituent on the ring carbon adjacent to the ring oxygen;

or a pharmaceutically acceptable salt or in vivo hydrolysable ester thereof.

Another preferred class of compound is of the formula (1) wherein:

----- is a single bond;
X is CH;
$R^4$ and $R^5$ are together —S—C($R^6$)=C($R^7$)—;
$R^6$ is hydrogen or halo;
$R^7$ is hydrogen or halo;
A is phenylene;
n is 0, 1 or 2;
$R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
$R^2$ is hydrogen;
$R^3$ is selected from cyanoC$_{1-4}$alkyl, and C$_{1-4}$alkyl (optionally substituted by 1 or 2 $R^8$ groups);
$R^8$ is independently selected from hydroxy, C$_{3-7}$cycloalkyl, phenyl, 2,2-dimethyl-1,3-dioxolan-4-yl; 2,2-dimethyl-1,3-dioxan-4-yl; 2,2-dimethyl-1,3-dioxan-5-yl, 1,2,4-oxadiazolyl, 1,3,4-oxadiazolyl, triazolyl, tetrazolyl, imidazolyl, pyrrolidinyl, piperidyl, tetrahydrofuryl, tetrahydropyranyl, tetrahydrothiopyranyl and tetrahydrothienyl, C$_{1-4}$alkoxy, C$_{1-4}$alkanoyl, C$_{1-4}$alkylS(O)$_b$— (wherein b is 0, 1 or 2), C$_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), —C(O)N($R^9$)($R^{10}$), —COOR$^9$, —C(O)NHSO$_2$Me, —C(=N—OH)NH$_2$, —C(=N—OH)NHC$_{1-4}$alkyl, —C(=N—OH)N(C$_{1-4}$alkyl)$_2$, —N(OH)CHO, —COCOOR$^9$, —NHC(O)R$^9$, ($R^9$)($R^{10}$)NSO$_2$—, —COCH$^2$OR$^{11}$ and —NHSO$_2$R$^9$;
$R^9$ and $R^{10}$ are independently selected from hydrogen, hydroxy, phenyl, heterocyclyl, heterocyclyl(C$_{1-4}$alkyl), C$_{1-4}$alkyl (optionally substituted by 1 or 2 hydroxy groups) and C$_{1-4}$alkyl substituted by C$_{1-4}$alkoxy and wherein $R^9$ and $R^{10}$ can together with the nitrogen to which they are attached form 4- to 6-membered ring where the ring is optionally substituted on carbon by 1 or 2 substituents selected from hydroxy or carboxy, or the ring may be optionally substituted on two adjacent carbons by —O—CH$_2$—O— to form a cyclic acetal wherein one or both of the hydrogens of the —O—CH$_2$—O— group may be replaced by a methyl;
$R^{11}$ is selected from hydrogen, C$_{1-4}$alkyl and hydroxyC$_{1-4}$alkyl;

or a pharmaceutically acceptable salt or in vivo hydrolysable ester thereof.

Another preferred class of compound is of the formula (1) wherein:

----- is a single bond;
X is CH;
$R^4$ and $R^5$ are together —S—C($R^6$)=C($R^7$)—;
$R^6$ is chloro;
$R^7$ is chloro;
A is phenylene;
n is 0, 1 or 2;
$R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
$R^2$ is hydrogen;
$R^3$ is selected from cyanoC$_{1-4}$alkyl, and C$_{1-4}$alkyl (optionally substituted by 1 or 2 $R^8$ groups);
$R^8$ is independently selected from hydroxy, phenyl, 2,2-dimethyl-1,3-dioxolan-4-yl; 2,2-dimethyl-1,3-dioxan-4-yl; 2,2-dimethyl-1,3-dioxan-5-yl, 1,2,4-oxadiazolyl, 1,3,4-oxadiazolyl, triazolyl, tetrazolyl, imidazolyl, pyrrolidinyl, piperidyl, tetrahydrofuryl, tetrahydropyranyl, tetrahydrothiopyranyl and tetrahydrothienyl, C$_{1-4}$alkoxy, C$_{1-4}$alkanoyl, C$_{1-4}$alkylS(O)$_b$— (wherein b is 0, 1 or 2), C$_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), —C(O)N($R^9$)($R^{10}$), —COOR$^9$, —C(O)NHSO$_2$Me, —C(=N—OH)NH$_2$, —C(=N—OH)NHC$_{1-4}$alkyl, —C(=N—OH)N(C$_{1-4}$alkyl)$_2$ and —NHSO$_2$R$^9$;
$R^9$ and $R^{10}$ are independently selected from hydrogen, hydroxy, phenyl, heterocyclyl, heterocyclyl(C$_{1-4}$alkyl), C$_{1-4}$alkyl (optionally substituted by 1 or 2 hydroxy groups) and C$_{1-4}$alkyl substituted by C$_{1-4}$alkoxy, and wherein $R^9$ and $R^{10}$ together with the nitrogen to which they are attached form a 4- to 6-membered ring selected from piperidine, 4-hydroxy piperidine, pyrrolidine, 3,4-dihydroxypyrrolidine and the dimethylacetal of 3,4-dihydroxypyrrolidine;

or a pharmaceutically acceptable salt or in vivo hydrolysable ester thereof.

Another preferred class of compound is of the formula (1) wherein:

----- is a single bond;
X is CH;
$R^4$ and $R^5$ are together —S—C($R^6$)=C($R^7$)—;
$R^6$ is chloro;
$R^7$ is chloro;
A is phenylene;
n is 0, 1 or 2;
$R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
$R^2$ is hydrogen;
$R^3$ is selected from groups of the formulae B and B':

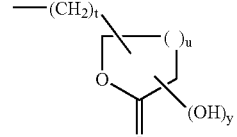
(B)

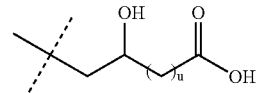
(B')

wherein y is 0 or 1, t is 0, 1, 2 or 3 and u is 1 or 2; provided that the hydroxy group is not a substituent on the ring carbon adjacent to the ring oxygen;

or a pharmaceutically acceptable salt or in vivo hydrolysable ester thereof.

A further preferred class of compound is of the formula (1) wherein;

----- is a single bond;
X is CH;
$R^4$ and $R^5$ are together —C($R^7$)=C($R^6$)—S—;
$R^6$ is halo;
$R^7$ is hydrogen;
A is phenylene;
n is 0, 1 or 2;
$R^1$ is independently selected from halo, cyano, nitro, hydroxy, methyl, fluoromethyl, difluoromethyl, trifluoromethyl, $C_{1-4}$alkoxy and, (when n is 2) methylenedioxy;
$R^2$ is hydrogen;
$R^3$ is selected from $C_{1-4}$alkyl (optionally substituted by 1 or 2 hydroxy groups);

or a pharmaceutically acceptable salt or in vivo hydrolysable ester thereof;

with the proviso that the compound of formula (1) is not
i. 2-chloro-5-[N-(1-methyl-2-oxo-1,2,3,4-tetrahydroquinol-3-yl)carbamoyl]-6H-thieno[2,3-b]pyrrole.

A further preferred class of compound is of the formula (1) wherein;

----- is a single bond;
X is CH;
$R^4$ and $R^5$ are together —C($R^7$)=C($R^6$)—S—;
$R^6$ is halo;
$R^7$ is hydrogen;
A is phenylene;
n is 0, 1 or 2;
$R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
$R^2$ is hydrogen;
$R^3$ is selected from cyano$C_{1-4}$alkyl, and $C_{1-4}$alkyl substituted by $R^8$;
$R^8$ is independently selected from hydroxy, $C_{1-4}$alkylS(O)$_b$— (wherein b is 0, 1 or 2), —NHC(O)$R^9$ and —C(O)N($R^9$)($R^{10}$);
$R^9$ and $R^{10}$ are independently selected from hydrogen, hydroxy, phenyl, heterocyclyl, heterocyclyl($C_{1-4}$alkyl), $C_{1-4}$alkyl (optionally substituted by 1 or 2 hydroxy groups) and $C_{1-4}$alkyl substituted by $C_{1-4}$alkoxy, and wherein $R^9$ and $R^{10}$ together with the nitrogen to which they are attached form a 4- to 6-membered ring selected from piperidine, 4-hydroxy piperidine, pyrrolidine, 3,4-dihydroxypyrrolidine and the dimethylacetal of 3,4-dihydroxypyrrolidine;

or a pharmaceutically acceptable salt or in vivo hydrolysable ester thereof.

Another class of compounds is of the formula (1) wherein

----- is a double bond;
X is CH;
$R^4$ and $R^5$ are together —C($R^7$)=C($R^6$)—S— or —S—C($R^7$)=C($R^6$)—;
$R^6$ is hydrogen or halo;
$R^7$ is hydrogen or halo;
A is phenylene;
n is 0, 1 or 2;
$R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
$R^2$ is hydrogen;
$R^3$ is selected from cyano$C_{1-4}$alkyl, and $C_{1-4}$alkyl (optionally substituted by 1 or 2 $R^8$ groups);
$R^8$ is independently selected from hydroxy, $C_{3-7}$cycloalkyl, phenyl, 2,2-dimethyl-1,3-dioxolan-4-yl; 2,2-dimethyl-1,3-dioxan-4-yl; 2,2-dimethyl-1,3-dioxan-5-yl, 1,2,4-oxadiazolyl, 1,3,4-oxadiazolyl, triazolyl, tetrazolyl, imidazolyl, pyrrolidinyl, piperidyl, tetrahydrofuryl, tetrahydropyranyl, tetrahydrothiopyranyl and tetrahydrothienyl, $C_{1-4}$alkoxy, $C_{1-4}$alkanoyl, $C_{1-4}$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), —C(O)N($R^9$)($R^{10}$), —COOR$^9$, —C(O)NHSO$_2$Me, —C(=N—OH)NH$_2$, —C(=N—OH)NH$C_{1-4}$alkyl, —C(=N—OH)N($C_{1-4}$alkyl)$_2$—N(OH)CHO, —COCOOR$^9$, —NHC(O)$R^9$, ($R^9$)($R^{10}$)NSO$_2$—, —COCH$^2$OR$^{11}$ and —NHSO$_2$R$^9$;
$R^9$ and $R^{10}$ are independently selected from hydrogen, hydroxy, phenyl, heterocyclyl, heterocyclyl($C_{1-4}$alkyl), $C_{1-4}$alkyl (optionally substituted by 1 or 2 hydroxy groups) and $C_{1-4}$alkyl substituted by $C_{1-4}$alkoxy and wherein $R^9$ and $R^{10}$ can together with the nitrogen to which they are attached form 4- to 6-membered ring where the ring is optionally substituted on carbon by 1 or 2 substituents selected from hydroxy or carboxy, or the ring may be optionally substituted on two adjacent carbons by —O—CH$_2$—O— to form a cyclic acetal wherein one or both of the hydrogens of the —O—CH$_2$—O— group may be replaced by a methyl;
$R^{11}$ is selected from hydrogen, $C_{1-4}$alkyl and hydroxy$C_{1-4}$alkyl;

or a pharmaceutically acceptable salt or in vivo hydrolysable ester thereof.

A further class of compound is of formula (1) wherein:

----- is a single bond;
X is CH;
$R^4$ and $R^5$ are together —C($R^7$)=C($R^6$)—S— or —S—C($R^7$)=C($R^6$)—;
$R^6$ is hydrogen or halo;
$R^7$ is hydrogen or hydrogen;
A is heteroarylene;
n is 0, 1 or 2;

$R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;

$R^2$ is hydrogen;

$R^3$ is selected from cyanoC$_{1-4}$alkyl, and C$_{1-4}$alkyl (optionally substituted by 1 or 2 $R^8$ groups)

$R^8$ is independently selected from hydroxy, C$_{3-7}$cycloalkyl, phenyl, 2,2-dimethyl-1,3-dioxolan-4-yl; 2,2-dimethyl-1,3-dioxan-4-yl; 2,2-dimethyl-1,3-dioxan-5-yl, 1,2,4-oxadiazolyl, 1,3,4-oxadiazolyl, triazolyl, tetrazolyl, imidazolyl, pyrrolidinyl, piperidyl, tetrahydrofuryl, tetrahydropyranyl, tetrahydrothiopyranyl and tetrahydrothienyl, C$_{1-4}$alkoxy, C$_{1-4}$alkanoyl, C$_{1-4}$alkylS(O)$_b$— (wherein b is 0, 1 or 2), C$_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), —C(O)N(R$^9$)(R$^{10}$), —COOR$^9$, —C(O)NHSO$_2$Me, —C(=N—OH)NH$_2$, —C(=N—OH)NHC$_{1-4}$alkyl, —C(=N—OH)N(C$_{1-4}$alkyl)$_2$, —N(OH)CHO, —COCOOR$^9$, —NHC(O)R$^9$, (R$^9$)(R$^{10}$)NSO$_2$—, —COCH$^2$OR$^{11}$ and —NHSO$_2$R$^9$;

$R^9$ and $R^{10}$ are independently selected from hydrogen, hydroxy, phenyl, heterocyclyl, heterocyclyl(C$_{1-4}$alkyl), C$_{1-4}$alkyl (optionally substituted by 1 or 2 hydroxy groups) and C$_{1-4}$alkyl substituted by C$_{1-4}$alkoxy and wherein $R^9$ and $R^{10}$ can together with the nitrogen to which they are attached form 4- to 6-membered ring where the ring is optionally substituted on carbon by 1 or 2 substituents selected from hydroxy or carboxy, or the ring may be optionally substituted on two adjacent carbons by —O—CH$_2$—O— to form a cyclic acetal wherein one or both of the hydrogens of the —O—CH$_2$—O— group may be replaced by a methyl;

$R^{11}$ is selected from hydrogen, C$_{1-4}$alkyl, hydroxyC$_{1-4}$alkyl;

or a pharmaceutically acceptable salt or in vivo hydrolysable ester thereof.

Yet another preferred class of compound is of the formula (1) wherein;

----- is a single bond;

X is N;

$R^4$ and $R^5$ are together —C(R$^7$)=C(R$^6$)—S—;

$R^6$ is halo;

$R^7$ is hydrogen;

A is phenylene;

n is 0, 1 or 2;

$R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;

$R^2$ is hydrogen;

$R^3$ is selected from cyanoC$_{1-4}$alkyl, and C$_{1-4}$alkyl (optionally substituted by 1 or 2 $R^8$ groups);

$R^8$ is independently selected from hydroxy, C$_{3-7}$cycloalkyl, phenyl, 2,2-dimethyl-1,3-dioxolan-4-yl; 2,2-dimethyl-1,3-dioxan-4-yl; 2,2-dimethyl-1,3-dioxan-5-yl, 1,2,4-oxadiazolyl, 1,3,4-oxadiazolyl, triazolyl, tetrazolyl, imidazolyl, pyrrolidinyl, piperidyl, tetrahydrofuryl, tetrahydropyranyl, tetrahydrothiopyranyl and tetrahydrothienyl, C$_{1-4}$alkoxy, C$_{1-4}$alkanoyl, C$_{1-4}$alkylS(O)$_b$— (wherein b is 0, 1 or 2), C$_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), —C(O)N(R$^9$)(R$^{10}$), —COOR$^9$, —C(O)NHSO$_2$Me, —C(=N—OH)NH$_2$, —C(=N—OH)NHC$_{1-4}$alkyl, —C(=N—OH)N(C$_{1-4}$alkyl)$_2$, —N(OH)CHO, —COCOOR$^9$, —NHC(O)R$^9$, (R$^9$)(R$^{10}$)NSO$_2$—, —COCH$^2$OR$^{11}$ and —NHSO$_2$R$^9$;

$R^9$ and $R^{10}$ are independently selected from hydrogen, hydroxy, phenyl, heterocyclyl, heterocyclyl(C$_{1-4}$alkyl), C$_{1-4}$alkyl (optionally substituted by 1 or 2 hydroxy groups) and C$_{1-4}$alkyl substituted by C$_{1-4}$alkoxy and wherein $R^9$ and $R^{10}$ can together with the nitrogen to which they are attached form 4- to 6-membered ring where the ring is optionally substituted on carbon by 1 or 2 substituents selected from hydroxy or carboxy, or the ring may be optionally substituted on two adjacent carbons by —O—CH$_2$—O— to form a cyclic acetal wherein one or both of the hydrogens of the —O—CH$_2$—O— group may be replaced by a methyl;

$R^{11}$ is selected from hydrogen, C$_{1-4}$alkyl and hydroxyC$_{1-4}$alkyl;

or a pharmaceutically acceptable salt or in vivo hydrolysable ester thereof.

Another preferred class of compounds is of formula (1) wherein:

----- is a single bond;

X is N;

$R^4$ and $R^5$ are together —C(R$^7$)=C(R$^6$)—S—;

$R^6$ is chloro;

$R^7$ is hydrogen;

A is phenylene;

n is 0, 1 or 2;

$R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;

$R^2$ is hydrogen;

$R^3$ is selected from cyanoC$_{1-4}$alkyl, and C$_{1-4}$alkyl (optionally substituted by 1 or 2 $R^8$ groups);

$R^8$ is independently selected from hydroxy, phenyl, 2,2-dimethyl-1,3-dioxolan-4-yl; 2,2-dimethyl-1,3-dioxan-4-yl; 2,2-dimethyl-1,3-dioxan-5-yl, 1,2,4-oxadiazolyl, 1,3,4-oxadiazolyl, triazolyl, tetrazolyl, imidazolyl, pyrrolidinyl, piperidyl, tetrahydrofuryl, tetrahydropyranyl, tetrahydrothiopyranyl and tetrahydrothienyl, C$_{1-4}$alkoxy, C$_{1-4}$alkanoyl, C$_{1-4}$aakylS(O)$_b$— (wherein b is 0, 1 or 2), C$_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), —C(O)N(R$^9$)(R$^{10}$), —COOR$^9$, —C(O)NHSO$_2$Me, —C(=N—OH)NH$_2$, —C(=N—OH)NHC$_{1-4}$alkyl, —C(=N—OH)N(C$_{1-4}$alkyl)$_2$ and —NHSO$_2$R$^9$;

$R^9$ and $R^{10}$ are independently selected from hydrogen, hydroxy, phenyl, heterocyclyl, heterocyclyl(C$_{1-4}$alkyl), C$_{1-4}$alkyl (optionally substituted by 1 or 2 hydroxy groups) and C$_{1-4}$alkyl substituted by C$_{1-4}$alkoxy and wherein $R^9$ and $R^{10}$ can together with the nitrogen to which they are attached form 4- to 6-membered ring where the ring is optionally substituted on carbon by 1 or 2 substituents selected from hydroxy or carboxy or the ring may be optionally substituted on two adjacent carbons by —O—CH$_2$—O— to form a cyclic acetal wherein one or both of the hydrogens of the —O—CH$_2$—O— group may be replaced by a methyl;

or a pharmaceutically acceptable salt or in vivo hydrolysable ester thereof;

Another preferred class of compound is of the formula (1) wherein:

----- is a single bond;
X is N;
$R^4$ and $R^5$ are together —S—C($R^6$)=C($R^7$)—;
$R^6$ is hydrogen or halo;
$R^7$ is hydrogen or halo;
A is phenylene;
n is 0, 1 or 2;
$R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
$R^2$ is hydrogen;
$R^3$ is selected from cyanoC$_{1-4}$alkyl, and C$_{1-4}$alkyl (optionally substituted by 1 or 2 $R^8$ groups);
$R^8$ is independently selected from hydroxy, phenyl, 2,2-dimethyl-1,3-dioxolan-4-yl; 2,2-dimethyl-1,3-dioxan-4-yl; 2,2-dimethyl-1,3-dioxan-5-yl, 1,2,4-oxadiazolyl, 1,3,4-oxadiazolyl, triazolyl, tetrazolyl, imidazolyl, pyrrolidinyl, piperidyl, tetrahydrofuryl, tetrahydropyranyl, tetrahydrothiopyranyl and tetrahydrothienyl, C$_{1-4}$alkoxy, C$_{1-4}$alkanoyl, C$_{1-4}$alkylS(O)$_b$— (wherein b is 0, 1 or 2), C$_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), —C(O)N($R^9$)($R^{10}$), —COO$R^9$, —C(O)NHSO$_2$Me, —C(=N—OH)NH$_2$, —C(=N—OH)NHC$_{1-4}$alkyl, —C(=N—OH)N(C$_{1-4}$alkyl)$_2$ and —NHSO$_2R^9$;
$R^9$ and $R^{10}$ are independently selected from hydrogen, hydroxy, phenyl, heterocyclyl, heterocyclyl(C$_{1-4}$alkyl), C$_{1-4}$alkyl (optionally substituted by 1 or 2 hydroxy groups) and C$_{1-4}$alkyl substituted by C$_{1-4}$alkoxy and wherein $R^9$ and $R^{10}$ can together with the nitrogen to which they are attached form 4- to 6-membered ring where the ring is optionally substituted on carbon by 1 or 2 substituents selected from hydroxy or carboxy or the ring may be optionally substituted on two adjacent carbons by —O—CH$_2$—O— to form a cyclic acetal wherein one or both of the hydrogens of the —O—CH$_2$—O— group may be replaced by a methyl;

or a pharmaceutically acceptable salt or in vivo hydrolysable ester thereof.

A further preferred class of compound is of the formula (1) wherein;

----- is a single bond;
X is N;
$R^4$ and $R^5$ are together —C($R^7$)=C($R^6$)—S—;
$R^6$ is halo;
$R^7$ is hydrogen;
A is phenylene;
n is 0, 1 or 2;

$R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
$R^2$ is hydrogen;
$R^3$ is selected from C$_{1-4}$alkyl (optionally substituted by 1 or 2 hydroxy groups);

or a pharmaceutically acceptable salt or in vivo hydrolysable ester thereof;

A further preferred class of compound is of the formula (1) wherein;

----- is a single bond;
X is N;
$R^4$ and $R^5$ are together —C($R^7$)=C($R^6$)—S—;
$R^6$ is halo;
$R^7$ is hydrogen;
A is phenylene;
n is 0, 1 or 2;
$R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
$R^2$ is hydrogen;
$R^3$ is selected from cyanoC$_{1-4}$alkyl, and C$_{1-4}$alkyl substituted by $R^8$;
$R^8$ is independently selected from hydroxy, C$_{1-4}$alkylS(O)$_b$— (wherein b is 0, 1 or 2), —NHC(O)$R^9$ and —C(O)N($R^9$)($R^{10}$);
$R^9$ and $R^{10}$ are independently selected from hydrogen, hydroxy, phenyl, heterocyclyl, heterocyclyl(C$_{1-4}$alkyl), C$_{1-4}$alkyl (optionally substituted by 1 or 2 hydroxy groups) and C$_{1-4}$alkyl substituted by C$_{1-4}$alkoxy, and wherein $R^9$ and $R^{10}$ together with the nitrogen to which they are attached form a 4- to 6-membered ring selected from piperidine, 4-hydroxy piperidine, pyrrolidine, 3,4-dihydroxypyrrolidine and the dimethylacetal of 3,4-dihydroxypyrrolidine;

or a pharmaceutically acceptable salt or in vivo hydrolysable ester thereof.

Another class of compounds is of the formula (1) wherein

----- is a double bond;
X is N;
$R^4$ and $R^5$ are together —C($R^7$)=C($R^6$)—S— or —S—C($R^7$)=C($R^6$)—;
$R^6$ is hydrogen or halo;
$R^7$ is hydrogen or halo;
A is phenylene;
n is 0, 1 or 2;
$R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
$R^2$ is hydrogen;
$R^3$ is selected from C$_{1-4}$alkyl (optionally substituted by 1 or 2 $R^8$ groups);

R⁸ is independently selected from hydroxy, $C_{3-7}$cycloalkyl, phenyl, 2,2-dimethyl-1,3-dioxolan-4-yl; 2,2-dimethyl-1,3-dioxan-4-yl; 2,2-dimethyl-1,3-dioxan-5-yl, 1,2,4-oxadiazolyl, 1,3,4-oxadiazolyl, triazolyl, tetrazolyl, imidazolyl, pyrrolidinyl, piperidyl, tetrahydrofuryl, tetrahydropyranyl, tetrahydrothiopyranyl and tetrahydrothienyl, $C_{1-4}$alkoxy, $C_{1-4}$alkanoyl, $C_{1-4}$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), —C(O)N(R⁹)(R¹⁰), —COOR⁹, —C(O)NHSO₂Me, —C(=N—OH)NH₂₂, —C(=N—OH)NHC$_{1-4}$alkyl, —C(=N—OH)N(C$_{1-4}$alkyl)₂, —N(OH)CHO, —COCOOR⁹, —NHC(O)R⁹, (R⁹)(R¹⁰)NSO₂—, —COCH²OR¹¹ and —NHSO₂R⁹;

R⁹ and R¹⁰ are independently selected from hydrogen, hydroxy, phenyl, heterocyclyl, heterocyclyl(C$_{1-4}$alkyl), C$_{1-4}$alkyl (optionally substituted by 1 or 2 hydroxy groups) and C$_{1-4}$alkyl substituted by C$_{1-4}$alkoxy and wherein R⁹ and R¹⁰ can together with the nitrogen to which they are attached form 4- to 6-membered ring where the ring is optionally substituted on carbon by 1 or 2 substituents selected from hydroxy or carboxy, or the ring may be optionally substituted on two adjacent carbons by —O—CH₂—O— to form a cyclic acetal wherein one or both of the hydrogens of the —O—CH₂—O— group may be replaced by a methyl;

R¹¹ is selected from hydrogen, C$_{1-4}$alkyl and hydroxyC$_{1-4}$alkyl;

or a pharmaceutically acceptable salt or in vivo hydrolysable ester thereof.

A further class of compound is of formula (1) wherein:

is a single bond;

X is N;

R⁴ and R⁵ are together —C(R⁷)=C(R⁶)—S— or —S—C(R⁷)=C(R⁶)—;

R⁶ is hydrogen or halo;

R⁷ is hydrogen or hydrogen;

A is heteroarylene;

n is 0, 1 or 2;

R¹ is independently selected from halo, cyano, nitro, hydroxy, methyl, fluoromethyl, difluoromethyl, trifluoromethyl, methoxy, —SMe, —SOMe, —SO₂Me and, (when n is 2) methylenedioxy;

R² is hydrogen;

R³ is selected from C$_{1-4}$alkyl (optionally substituted by 1 or 2 R⁸ groups);

R⁸ is independently selected from hydroxy, $C_{3-7}$cycloalkyl, phenyl, 2,2-dimethyl-1,3-dioxolan-4-yl; 2,2-dimethyl-1,3-dioxan-4-yl; 2,2-dimethyl-1,3-dioxan-5-yl, 1,2,4-oxadiazolyl, 1,3,4-oxadiazolyl, triazolyl, tetrazolyl, imidazolyl, pyrrolidinyl, piperidyl, tetrahydrofuryl, tetrahydropyranyl, tetrahydrothiopyranyl and tetrahydrothienyl, $C_{1-4}$alkoxy, $C_{1-4}$alkanoyl, $C_{1-4}$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), —C(O)N(R⁹)(R¹⁰), —COOR⁹, —C(O)NHSO₂Me, —C(=N—OH)NH₂, —C(=N—OH)NHC$_{1-4}$alkyl, —C(=N—OH)N(C$_{1-4}$alkyl)₂—N(OH)CHO, —COCOOR⁹, —NHC(O)R⁹, (R⁹)(R¹⁰)NSO₂—, —COCH²OR¹¹ and —NHSO₂R⁹;

R⁹ and R¹⁰ are independently selected from hydrogen, hydroxy, phenyl, heterocyclyl, heterocyclyl(C$_{1-4}$alkyl), C$_{1-4}$alkyl (optionally substituted by 1 or 2 hydroxy groups) and C$_{1-4}$alkyl substituted by C$_{1-4}$alkoxy and wherein R⁹ and R¹⁰ can together with the nitrogen to which they are attached form 4- to 6-membered ring where the ring is optionally substituted on carbon by 1 or 2 substituents selected from hydroxy or carboxy, or the ring may be optionally substituted on two adjacent carbons by —O—CH₂—O— to form a cyclic acetal wherein one or both of the hydrogens of the —O—CH₂—O— group may be replaced by a methyl;

R¹¹ is selected from hydrogen, C$_{1-4}$alkyl and hydroxyC$_{1-4}$alkyl;

or a pharmaceutically acceptable salt or in vivo hydrolysable ester thereof.

In another aspect of the invention, a preferred class of compound is of the formula (1) wherein;

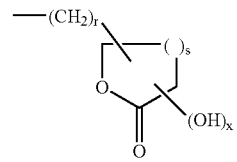

is a single bond;

X is CH;

R⁴ and R⁵ are together —C(R⁷)=C(R⁶)—S—;

R⁶ is halo;

R⁷ is hydrogen;

A is phenylene;

n is 1 or 2;

R¹ is independently selected from hydrogen, halo, cyano, nitro, hydroxy, fluoromethyl, difluoromethyl, trifluoromethyl, C$_{1-4}$alkoxy and R¹ is of the formula A' or A":

—(CH₂)ᵣ—[ring with O, C=O, ()ₛ, (OH)ₓ]  (A')

—CH₂CH(OH)(CH₂)ᵤCO₂H  (A")

wherein x is 0 or 1, r is 0, 1, 2 or 3 and s is 1 or 2; provided that the hydroxy group is not a substituent on the ring carbon adjacent to the ring oxygen;

R² is hydrogen;

R³ is selected from C$_{1-4}$alkyl (optionally substituted by 1 or 2 hydroxy groups provided that when there are 2 hydroxy groups they are not substituents on the same carbon), cyanoC$_{1-4}$alkyl, and C$_{1-4}$alkyl [substituted by 1 or 2 R⁸ groups (provided that when there are 2 R⁸ groups they are not substituents on the same carbon)];

{R⁵ is independently selected from hydroxy, heterocyclyl, C$_{1-4}$alkanoyl, C$_{1-4}$alkoxy, C$_{1-4}$alkanesulfinyl, C$_{1-4}$alkanesulfonyl, —COCOOR⁹, (R⁹)(R¹⁰)NCO—, —COCH₂OR¹¹, (R⁹)(R¹⁰)N—, —COOR⁹ and 2,2-dimethyl-1,3-dioxolan-4-yl;

[R⁹ and R¹⁰ are independently selected from hydrogen, hydroxy, C$_{1-4}$alkyl (optionally substituted by 1 or 2 hydroxy groups provided that when there are 2 hydroxy groups they are not substituents on the same carbon) and C$_{1-4}$alkyl substituted by C$_{1-4}$alkoxy and wherein R⁹ and R¹⁰ can together with the nitrogen to which they are attached form 4- to 6-membered ring where the ring is optionally substituted on carbon by 1 or 2 substituents selected from hydroxy or carboxy;
$R^{11}$ is selected from hydrogen, $C_{1-4}$alkyl, $C_{1-4}$alkoxy and hydroxy$C_{1-4}$alkyl]};

or a pharmaceutically acceptable salt or in vivo hydrolysable ester thereof;

with the proviso that the compound of formula (1) is not:
ii. 2-chloro-5-[N-(2-oxo-1,2,3,4-tetrahydroquinol-3-yl)carbamoyl]-6H-thieno[2,3-b]pyrrole; or
iii. 2-chloro-5-[N—(1-methyl-2-oxo-1,2,3,4-tetrahydroquinol-3-yl)carbamoyl]-6H-thieno[2,3-b]pyrrole.

In another aspect of the invention, another preferred class of compounds is of formula (1) wherein:

is a single bond;
X is CH;
$R^4$ and $R^5$ are together —C($R^7$)═C($R^6$)—S—;
$R^6$ is chloro;
$R^7$ is hydrogen;
A is phenylene;
n is 1 or 2;
$R^1$ is independently selected from hydrogen, halo, nitro, hydroxy, $C_{1-4}$alkyl, $C_{1-4}$alkoxy and
$R^1$ is of the formula A' or A":

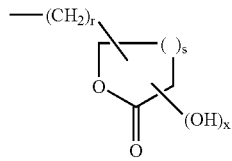

(A')

—CH$_2$CH(OH)(CH$_2$)$_u$CO$_2$H (A")

wherein x is 0 or 1, r is 0, 1, 2 or 3 and s is 1 or 2; provided that the hydroxy group is not a substituent on the ring carbon adjacent to the ring oxygen;
$R^2$ is hydrogen;
$R^3$ is selected from $C_{1-4}$alkyl (optionally substituted by 1 or 2 hydroxy groups provided that when there are 2 hydroxy groups they are not substituents on the same carbon), cyano$C_{1-4}$alkyl, and $C_{1-4}$alkyl [substituted by 1 or 2 $R^8$ groups (provided that when there are 2 $R^8$ groups they are not substituents on the same carbon)];
{$R^8$ is independently selected from hydroxy, heterocyclyl, $C_{1-4}$alkanoyl, $C_{1-4}$alkoxy, $C_{1-4}$alkanesulfinyl, $C_{1-4}$alkylsulfonyl, —COCOOR$^9$, ($R^9$)($R^{10}$)NCO—, —COCH$_2$OR$^{11}$, ($R^9$)($R^{10}$)N—, —COOR$^9$ and 2,2-dimethyl-1,3-dioxolan-4-yl;
[$R^9$ and $R^{10}$ are independently selected from hydrogen, hydroxy, $C_{1-4}$alkyl (optionally substituted by 1 or 2 hydroxy groups provided that when there are 2 hydroxy groups they are not substituents on the same carbon) and $C_{1-4}$alkyl substituted by $C_{1-4}$alkoxy and wherein $R^9$ and $R^{10}$ can together with the nitrogen to which they are attached form 4- to 6-membered ring where the ring is optionally substituted on carbon by 1 or 2 substituents selected from hydroxy or carboxy;
$R^{11}$ is selected from hydrogen, $C_{1-4}$alkyl, $C_{1-4}$alkoxy and hydroxy$C_{1-4}$alkyl]};

or a pharmaceutically acceptable salt or in vivo hydrolysable ester thereof;

with the proviso that the compound of formula (1) is not:
ii. 2-chloro-5-[N-(2-oxo-1,2,3,4-tetrahydroquinol-3-yl)carbamoyl]-6H-thieno[2,3-b]pyrrole; or
iii. 2-chloro-5-[N—(1-methyl-2-oxo-1,2,3,4-tetrahydroquinol-3-yl)carbamoyl]-6H-thieno[2,3-b]pyrrole.

In another aspect of the invention, another preferred class of compound is of the formula (1) wherein:

is a single bond;
X is CH;
$R^4$ and $R^5$ are together —S—C($R^6$)═C($R^7$)—;
$R^6$ is hydrogen or halo;
$R^7$ is hydrogen or halo;
A is phenylene;
n is 1 or 2;
$R^1$ is independently selected from hydrogen, halo, nitro, hydroxy, $C_{1-4}$alkyl, $C_{1-4}$alkoxy and
$R^1$ is of the formula A' or A":

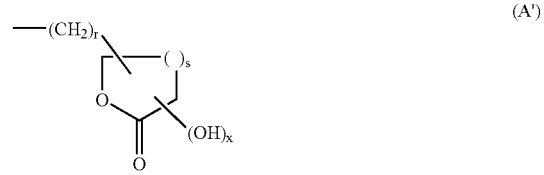

(A')

—CH$_2$CH(OH)(CH$_2$)$_u$CO$_2$H (A")

wherein x is 0 or 1, r is 0, 1, 2 or 3 and s is 1 or 2; provided that the hydroxy group is not a substituent on the ring carbon adjacent to the ring oxygen;
$R^2$ is hydrogen;
$R^3$ is selected from $C_{1-4}$alkyl (optionally substituted by 1 or 2 hydroxy groups provided that when there are 2 hydroxy groups they are not substituents on the same carbon), cyano$C_{1-4}$alkyl, and $C_{1-4}$alkyl [substituted by 1 or 2 $R^8$ groups (provided that when there are 2 $R_8$ groups they are not substituents on the same carbon)];
{$R^8$ is independently selected from hydroxy, heterocyclyl, $C_{1-4}$alkanoyl, $C_{1-4}$alkoxy, $C_{1-4}$alkanesulfinyl, $C_{1-4}$alkylsulfonyl, —COCOOR$^9$, ($R^9$)($R^{10}$)NCO—, —COCH$_2$OR$^{11}$, ($R^9$)($R^{10}$)N—, —COOR$^9$ and 2,2-dimethyl-1,3-dioxolan-4-yl;
[$R^9$ and $R^{10}$ are independently selected from hydrogen, hydroxy, $C_{1-4}$alkyl (optionally substituted by 1 or 2 hydroxy groups provided that when there are 2 hydroxy groups they are not substituents on the same carbon) and $C_{1-4}$alkyl substituted by $C_{1-4}$alkoxy and wherein $R^9$ and $R^{10}$ can together with the nitrogen to which they are attached form 4- to 6-membered ring where the ring is optionally substituted on carbon by 1 or 2 substituents selected from hydroxy or carboxy;
$R^{11}$ is selected from hydrogen, $C_{1-4}$alkyl, $C_{1-4}$alkoxy and hydroxy$C_{1-4}$alkyl]};

or a pharmaceutically acceptable salt or in vivo hydrolysable ester thereof;

with the proviso that the compound of formula (1) is not 2,3-dichloro-5-[N-(2-oxo-1,2,3,4-tetrahydroquinol-3-yl) carbamoyl]-4H-thieno[3,2-b]pyrrole.

In another aspect of the invention, preferred compounds of the invention are any one of:

2-chloro-N-[1-(methoxycarbonylmethyl)-2-oxo-1,2,3,4-tetrahydroquinolin-3-yl]-6H-thieno[2,3-b]pyrrole-5-carboxamide;

N-[1-(carboxymethyl)-2-oxo-1,2,3,4-tetrahydroquinolin-3-yl]-2-chloro-6H-thieno[2,3-b]pyrrole-5-carboxamide;

2-chloro-N-[1-(carbamoylmethyl)-2-oxo-1,2,3,4-tetrahydroquinolin-3-yl]-6H-thieno[2,3-b]pyrrole-5-carboxamide;

2-chloro-N-[1-(N,N-dimethylcarbamoylmethyl)-2-oxo-1,2,3,4-tetrahydroquinolin-3-yl]-6H-thieno[2,3-b]pyrrole-5-carboxamide;

2-chloro-N-[1-(N-methylcarbamoylmethyl)-2-oxo-1,2,3,4-tetrahydroquinolin-3-yl]-6H-thieno[2,3-b]pyrrole-5-carboxamide;

2-chloro-N-[1-(N-hydroxycarbamoylmethyl)-2-oxo-1,2,3,4-tetrahydroquinolin-3-yl]-6H-thieno[2,3-b]pyrrole-5-carboxamide;

2-chloro-N-{1-[N-(2-hydroxyethyl)carbamoylmethyl]-2-oxo-1,2,3,4-tetrahydroquinolin-3-yl}-6H-thieno[2,3-b]pyrrole-5-carboxamide;

2-chloro-N-[1-(2-hydroxyethyl)-2-oxo-1,2,3,4-tetrahydroquinolin-3-yl]-6H-thieno[2,3-b]pyrrol-5-ylcarboxamide;

2-chloro-N-[1-(2,3-dihydroxypropyl)-2-oxo-1,2,3,4-tetrahydroquinolin-3-yl]-6H-thieno[2,3-b]pyrrole-5-carboxamide;

2-chloro-N-{1-[(2,2-dimethyl-1,3-dioxolan-4(S)-yl)methyl]-2-oxo-1,2,3,4-tetrahydroquinolin-3(R,S)-yl}-6H-thieno[2,3-b]pyrrole-5-carboxamide;

2-chloro-N-[1-(2(S),3-dihydroxypropyl)-2-oxo-1,2,3,4-tetrahydroquinolin-3(R,S)-yl]-6H-thieno[2,3-b]pyrrole-5-carboxamide;

2-chloro-N-[1-(2,2-dimethyl-1,3-dioxolan-4(R)-ylmethyl)-2-oxo-1,2,3,4-tetrahydroquinolin-3(R,S)-yl]-6H-thieno[2,3-b]pyrrole-5-carboxamide;

2-chloro-N-[1-(2(R),3-dihydroxypropyl)-2-oxo-1,2,3,4-tetrahydroquinolin-3(R,S)-yl]-6H-thieno [2,3-b]pyrrole-5-carboxamide;

2-chloro-N-{1-[2-(4-hydroxypiperidin-1-yl)-2-oxoethyl]-2-oxo-1,2,3,4-tetrahydroquinolin-3-yl}-6H-thieno[2,3-b]pyrrole-5-carboxamide;

2-chloro-N-{1-[N-(1,3-dihydroxyprop-2-yl)carbamoylmethyl]-2-oxo-1,2,3,4-tetrahydroquinolin-3-yl}-6H-thieno[2,3-b]pyrrole-5-carboxamide;

2-chloro-N-{1-[N-(2-methoxyethyl)carbamoylmethyl]-2-oxo-1,2,3,4-tetrahydroquinolin-3-yl}-6H-thieno[2,3-b]pyrrole-5-carboxamide;

2-chloro-N-(1-{2-[(3a,6a-cis)-2,2-dimethyltetrahydro-5H-[1,3]dioxolo[4,5-c]pyrrol-5-yl]-2-oxoethyl}-2-oxo-1,2,3,4-tetrahydroquinolin-3-yl)-6H-thieno[2,3-b]pyrrole-5-carboxamide;

2-chloro-N-(1-{2-[(cis)-3,4-dihydroxypyrrolidin-1-yl]-2-oxoethyl}-2-oxo-1,2,3,4-tetrahydroquinolin-3-yl)-6H-thieno[2,3-b]pyrrole-5-carboxamide;

2-chloro-N-{1-[2-(dimethylamino)ethyl]-2-oxo-1,2,3,4-tetrahydroquinolin-3-yl}-6H-thieno[2,3-b]pyrrole-5-carboxamide;

2-chloro-N-{1-[(2,2-dimethyl-1,3-dioxan-5-yl)methyl]-2-oxo-1,2,3,4-tetrahydroquinolin-3-yl}-6H-thieno[2,3-b]pyrrole-5-carboxamide;

2-chloro-N-{1-[3-hydroxy-2-(hydroxymethyl)propyl]-2-oxo-1,2,3,4-tetrahydroquinolin-3-yl}-6H-thieno[2,3-b]pyrrole-5-carboxamide;

2,3-dichloro-N-{1-[(2,2-dimethyl-1,3-dioxan-5-yl)methyl]-2-oxo-1,2,3,4-tetrahydroquinolin-3-yl}-4H-thieno[3,2-b]pyrrole-5-carboxamide;

2,3-dichloro-N-{1-[3-hydroxy-2-(hydroxymethyl)propyl]-2-oxo-1,2,3,4-tetrahydroquinolin-3-yl}-4H-thieno[3,2-b]pyrrole-5-carboxamide;

2-chloro-N-(1-{2-[(2,3-dihydroxypropyl)amino]-2-oxoethyl}-2-oxo-1,2,3,4-tetrahydroquinolin-3-yl)-6H-thieno[2,3-b]pyrrole-5-carboxamide;

2-chloro-N-{1-[2-(methoxy)ethyl]-2-oxo-1,2,3,4-tetrahydroquinolin-3-yl}-6H-thieno[2,3-b]pyrrole-5-carboxamide;

2-chloro-N-[1-(cyanomethyl)-2-oxo-1,2,3,4-tetrahydroquinolin-3-yl]-6H-thieno[2,3-b]pyrrole-5-carboxamide;

2-chloro-N-{1-[(3-methyl-1,2,4-oxadiazol-5-yl)methyl]-2-oxo-1,2,3,4-tetrahydroquinolin-3-yl}-6H-thieno[2,3-b]pyrrole-5-carboxamide;

2-chloro-N-[2-oxo-1-(1H-tetrazol-5-ylmethyl)-1,2,3,4-tetrahydroquinolin-3-yl]-6H-thieno[2,3-b]pyrrole-5-carboxamide;

2-chloro-N-(1-{2-[(methylsulphonyl)amino]-2-oxoethyl}-2-oxo-1,2,3,4-tetrahydroquinolin-3-yl)-6H-thieno[2,3-b]pyrrole-5-carboxamide;

N-{1-[(2Z)-2-amino-2-(hydroxyimino)ethyl]-2-oxo-1,2,3,4-tetrahydroquinolin-3-yl}-2-chloro-6H-thieno[2,3-b]pyrrole-5-carboxamide;

2-chloro-N-{2-oxo-1-[(5-oxo-4,5-dihydro-1,2,4-oxadiazol-3-yl)methyl]-1,2,3,4-tetrahydroquinolin-3-yl}-6H-thieno[2,3-b]pyrrole-5-carboxamide;

N-{1-[(5-amino-1,3,4-oxadiazol-2-yl)methyl]-2-oxo-1,2,3,4-tetrahydroquinolin-3-yl}-2-chloro-6H-thieno[2,3-b]pyrrole-5-carboxamide;

2-chloro-N-{1-[2-(methylthio)ethyl]-2-oxo-1,2,3,4-tetrahydroquinolin-3-yl}-6H-thieno[2,3-b]pyrrole-5-carboxamide;

2-chloro-N-{1-[2-(methylsulfinyl)ethyl]-2-oxo-1,2,3,4-tetrahydroquinolin-3-yl}-6H-thieno[2,3-b]pyrrole-5-carboxamide;

2-chloro-N-{1-[2-(methylsulfonyl)ethyl]-2-oxo-1,2,3,4-tetrahydroquinolin-3-yl}-6H-thieno[2,3-b]pyrrole-5-carboxamide;

2,3-dichloro-N-[1-(methoxycarbonylmethyl)-2-oxo-1,2,3,4-tetrahydroquinolin-3-yl]-4H-thieno[3,2-b]pyrrole-5-carboxamide;

N-[1-(carboxymethyl)-2-oxo-1,2,3,4-tetrahydroquinolin-3-yl]-2,3-dichloro-4H-thieno[3,2-b]pyrrole-5-carboxamide;

2,3-dichloro-N-[1-(2-hydroxyethyl)-2-oxo-1,2,3,4-tetrahydroquinolin-3-yl]-4H-thieno[3,2-b]pyrrole-5-carboxamide;

2,3-dichloro-N-{1-[(2R)-2,3-dihydroxypropyl]-2-oxo-1,2,3,4-tetrahydroquinolin-3-yl}-4H-thieno[3,2-b]pyrrole-5-carboxamide;

2-chloro-N-{1-[3-(dimethylamino)-2-hydroxypropyl]-2-oxo-1,2,3,4-tetrahydroquinolin-3-yl}-6H-thieno[2,3-b]pyrrole-5-carboxamide;

2-chloro-N-{2-oxo-1-[(2-oxo-1,3-dioxan-5-yl)methyl]-1,2,3,4-tetrahydroquinolin-3-yl}-6H-thieno[2,3-b]pyrrole-5-carboxamide;

2-chloro-N-[1-(3-hydroxypropyl)-2-oxo-1,2,3,4-tetrahydroquinolin-3-yl]-6H-thieno[2,3-b]pyrrole-5-carboxamide;

2-chloro-N-{1-[3-(methylamino)-3-oxopropyl]-2-oxo-1,2,3,4-tetrahydroquinolin-3-yl}-6H-thieno[2,3-b]pyrrole-5-carboxamide;

2-chloro-N-[2-oxo-1-(2-oxobutyl)-1,2,3,4-tetrahydroquinolin-3-yl]-6H-thieno[2,3-b]pyrrole-5-carboxamide.

2-chloro-N-[1-(2-hydroxybutyl)-2-oxo-1,2,3,4-tetrahydroquinolin-3-yl]-6H-thieno[2,3-b]pyrrole-5-carboxamide;

2,3-dichloro-N-[(6S)-7-oxo-5,6,7,8-tetrahydroimidazo[1,2-a]pyrimidin-6-yl]-4H-thieno[3,2-b]pyrrole-5-carboxamide;

2,3-dichloro-N-(2-oxo-1,2,3,4-tetrahydro-1,5-naphthyridin-3-yl)-4H-thieno[3,2-b]pyrrole-5-carboxamide;

2-chloro-N-(2-oxo-1,2,3,4-tetrahydro-1,7-naphthyridin-3-yl)-6H-thieno[2,3-b]pyrrole-5-carboxamide;

N-(6-fluoro-1,2,3,4-tetrahydroquinolin-3-yl)-6H-thieno[2,3-b]pyrrole-5-carboxamide; and N-(6-methoxy-1,2,3,4-tetrahydroquinolin-3-yl)-6H-thieno[2,3-b]pyrrole-5-carboxamide;

or a pharmaceutically acceptable salt or an in vivo hydrolysable ester thereof.

In another aspect of the invention, preferred compounds of the invention are any one of:

2-chloro-N-[1-(2-hydroxyethyl)-2-oxo-1,2,3,4-tetrahydroquinolin-3-yl]-6H-thieno[2,3-b]pyrrol-5-ylcarboxamide;

2-chloro-N-[1-(2,3-dihydroxypropyl)-2-oxo-1,2,3,4-tetrahydroquinolin-3-yl]-6H-thieno[2,3-b]pyrrole-5-carboxamide;

2-chloro-N-[1-(2(S),3-dihydroxypropyl)-2-oxo-1,2,3,4-tetrahydroquinolin-3(R,S)-yl]-6H-thieno[2,3-b]pyrrole-5-carboxamide;

2-chloro-N-[1-(2(R),3-dihydroxypropyl)-2-oxo-1,2,3,4-tetrahydroquinolin-3(R,S)-yl]-6H-thieno[2,3-b]pyrrole-5-carboxamide;

2-chloro-N-{1-[2-(4-hydroxypiperidin-1-yl)-2-oxoethyl]-2-oxo-1,2,3,4-tetrahydroquinolin-3-yl}-6H-thieno[2,3-b]pyrrole-5-carboxamide;

2-chloro-N-{1-[N-(1,3-dihydroxyprop-2-yl)carbamoylmethyl]-2-oxo-1,2,3,4-tetrahydroquinolin-3-yl}-6H-thieno[2,3-b]pyrrole-5-carboxamide;

2-chloro-N-{1-[N-(2-methoxyethyl)carbamoylmethyl]-2-oxo-1,2,3,4-tetrahydroquinolin-3-yl}-6H-thieno[2,3-b]pyrrole-5-carboxamide;

N-{1-[(2Z)-2-amino-2-(hydroxyimino)ethyl]-2-oxo-1,2,3,4-tetrahydroquinolin-3-yl}-2-chloro-6H-thieno[2,3-b]pyrrole-5-carboxamide;

2-chloro-N-(1-{2-[(3a,6a-cis)-2,2-dimethyltetrahydro-5H-[1,3]dioxolo[4,5-c]pyrrol-5-yl]-2-oxoethyl}-2-oxo-1,2,3,4-tetrahydroquinolin-3-yl)-6H-thieno[2,3-b]pyrrole-5-carboxamide;

2-chloro-N-(1-{2-[(cis)-3,4-dihydroxypyrrolidin-1-yl]-2-oxoethyl}-2-oxo-1,2,3,4-tetrahydroquinolin-3-yl)-6H-thieno[2,3-b]pyrrole-5-carboxamide;

2-chloro-N-{1-[3-hydroxy-2-(hydroxymethyl)propyl]-2-oxo-1,2,3,4-tetrahydroquinolin-3-yl}-6H-thieno[2,3-b]pyrrole-5-carboxamide;

2,3-dichloro-N-{1-[3-hydroxy-2-(hydroxymethyl)propyl]-2-oxo-1,2,3,4-tetrahydroquinolin-3-yl}-4H-thieno[3,2-b]pyrrole-5-carboxamide;

2-chloro-N-(1-{2-[(2,3-dihydroxypropyl)amino]-2-oxoethyl}-2-oxo-1,2,3,4-tetrahydroquinolin-3-yl)-6H-thieno[2,3-b]pyrrole-5-carboxamide;

2-chloro-N-{1-[2-(methylsulfinyl)ethyl]-2-oxo-1,2,3,4-tetrahydroquinolin-3-yl}-6H-thieno[2,3-b]pyrrole-5-carboxamide;

2-chloro-N-{1-[2-(methylsulfonyl)ethyl]-2-oxo-1,2,3,4-tetrahydroquinolin-3-yl}-6H-thieno[2,3-b]pyrrole-5-carboxamide;

2,3-dichloro-N-[1-(2-hydroxyethyl)-2-oxo-1,2,3,4-tetrahydroquinolin-3-yl]-4H-thieno[3,2-b]pyrrole-5-carboxamide;

2,3-dichloro-N-{1-[(2R)-2,3-dihydroxypropyl]-2-oxo-1,2,3,4-tetrahydroquinolin-3-yl}-4H-thieno[3,2-b]pyrrole-5-carboxamide;

2-chloro-N-[1-(3-hydroxypropyl)-2-oxo-1,2,3,4-tetrahydroquinolin-3-yl]-6H-thieno[2,3-b]pyrrole-5-carboxamide;

2-chloro-N-{1-[3-(methylamino)-3-oxopropyl]-2-oxo-1,2,3,4-tetrahydroquinolin-3-yl}-6H-thieno[2,3-b]pyrrole-5-carboxamide; and 2-chloro-N-[1-(2-hydroxybutyl)-2-oxo-1,2,3,4-tetrahydroquinolin-3-yl]-6H-thieno[2,3-b]pyrrole-5-carboxamide;

or a pharmaceutically acceptable salt or an in vivo hydrolysable ester thereof.

In another aspect of the invention, preferred compounds of the invention are any one of:

2-chloro-N-[1-(2-hydroxyethyl)-2-oxo-1,2,3,4-tetrahydroquinolin-3-yl]-6H-thieno[2,3-b]pyrrol-5-ylcarboxamide;

2-chloro-N-[1-(2(R),3-dihydroxypropyl)-2-oxo-1,2,3,4-tetrahydroquinolin-3(R,S)-yl]-6H-thieno[2,3-b]pyrrole-5-carboxamide;

2,3-dichloro-N-{1-[3-hydroxy-2-(hydroxymethyl)propyl]-2-oxo-1,2,3,4-tetrahydroquinolin-3-yl}-4H-thieno[3,2-b]pyrrole-5-carboxamide;

N-{1-[(2Z)-2-amino-2-(hydroxyimino)ethyl]-2-oxo-1,2,3,4-tetrahydroquinolin-3-yl}-2-chloro-6H-thieno[2,3-b]pyrrole-5-carboxamide;

2,3-dichloro-N-{1-[(2R)-2,3-dihydroxypropyl]-2-oxo-1,2,3,4-tetrahydroquinolin-3-yl}-4H-thieno[3,2-b]pyrrole-5-carboxamide; and 2-chloro-N-[1-(3-hydroxypropyl)-2-oxo-1,2,3,4-tetrahydroquinolin-3-yl]-6H-thieno[2,3-b]pyrrole-5-carboxamide;

or a pharmaceutically acceptable salt or an in vivo hydrolysable ester thereof.

Another aspect of the present invention provides a process for preparing a compound of formula (1) or a pharmaceutically acceptable salt or an in vivo hydrolysable ester thereof which process (wherein A, $R^1$, $R^2$, $R^3$, $R^4$, $R^5$, n and - - - are, unless otherwise specified, as defined in formula (1)) comprises of:

a) reacting an acid of the formula (2):

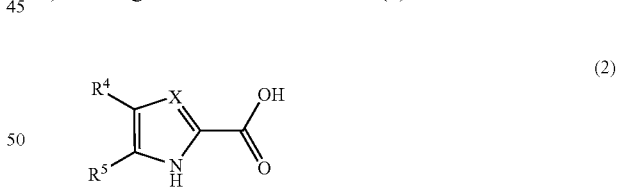

or an activated derivative thereof; with an amine of formula (3):

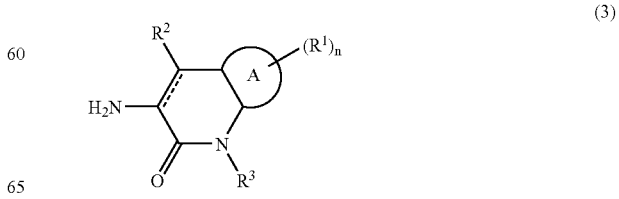

and thereafter if necessary:
i) converting a compound of the formula (1) into another compound of the formula (1);
ii) removing any protecting groups;
iii) forming a pharmaceutically acceptable salt or in vivo hydrolysable ester.

Specific reaction conditions for the above reaction are as follows.

Process a) Acids of formula (2) and amines of formula (3) may be coupled together in the presence of a suitable coupling reagent. Standard peptide coupling reagents known in the art can be employed as suitable coupling reagents, or for example carbonyldiimidazole, 1-ethyl-3-(3-dimethylaminopropyl)carbodi-imide hydrochloride (EDCI) and dicyclohexyl-carbodiimide (DCCI), optionally in the presence of a catalyst such as 1-hydroxybenzotriazole, dimethylaminopyridine or 4-pyrrolidinopyridine, optionally in the presence of a base for example triethylamine, di-isopropylethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C. Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

Where $R^3$ of formula (1) contains an ester group, the conversion of a compound of the formula (1) into another compound of the formula (1) may involve hydrolysis of the ester group, for example, acid or base hydrolysis, for example using lithium hydroxide. The reaction of this type is well known in the art.

Substituted amides wherein $R^3$ is $CH_2C(O)N(R^9)(R^{10})$ may be prepared from the corresponding acids by a coupling reaction using the appropriate amine in the presence of a coupling reagent, for example EDCI. Alternatively, the acid may first be converted to a mixed anhydride, by reaction with, for example, ethyl chloroformate, which is reacted with an appropriate amine to produce the substituted amide. Substituted sulphonamides wherein $R^3$ is $CH_2C(O)NHSO_2R_9$ may be prepared similarly, for instance by coupling the compounds wherein $R^3$ is $CH_2CO_2H$ with the appropriate substituted sulphonamide in the presence of a coupling reagent, for example EDCI.

Compounds of formula (1) wherein $R^3$ is 2-hydroxyethyl may be prepared by reduction of the mixed anhydrides described above with, for example, lithium borohydride. Compounds of formula (1) wherein $R^3$ is an oxadiazol-5-ylmethyl group may be prepared by reaction of the mixed anhydrides described above with an appropriately substituted hydroxyamidine, for example N-hydroxyethanimidamide, in the presence of a base such as N-methylmorpholine.

Compounds of formula (1) wherein $R^3$ is a tetrazol-5-ylmethyl group may be prepared by reaction of the corresponding compounds where $R^3$ is a cyanomethyl group with an azide, for example sodium azide, in the presence of an amine salt, for instance triethylamine hydrochloride. Compounds of formula (1) wherein $R^3$ is 2-amino-2-(hydroxyimino)ethyl may be prepared by reaction of compounds wherein $R^3$ is cyanomethyl with hydroxylamine hydrochloride in the presence of a base, for example sodium methoxide.

Compounds of formula (1) wherein $R^3$ is a 2-(methylsulphonyl)ethyl or 2-(methylsulphinyl)ethyl group may be prepared by reaction of the corresponding compounds where $R^3$ is 2-methylthioethyl with an oxidising agent, for example oxone.

Compounds of formula (1) wherein $R^3$ is a dihydroxyalkyl group, for example 2,3-dihydroxypropyl or 2-(hydroxymethyl)-3-hydroxypropyl may be prepared by acid hydrolysis of the corresponding compounds of formula (1) wherein $R^3$ is a protected dihydroxyalkyl group for example (2,2-dimethyl-1,3-dioxan-5-yl)methyl, (2,2-dimethyl-1,3-dioxolan-4-yl)methyl or (2-oxo-1,3-dioxan-5-yl)methyl.

The acids of formula (2), wherein X is CH, may be prepared according to Scheme 1:

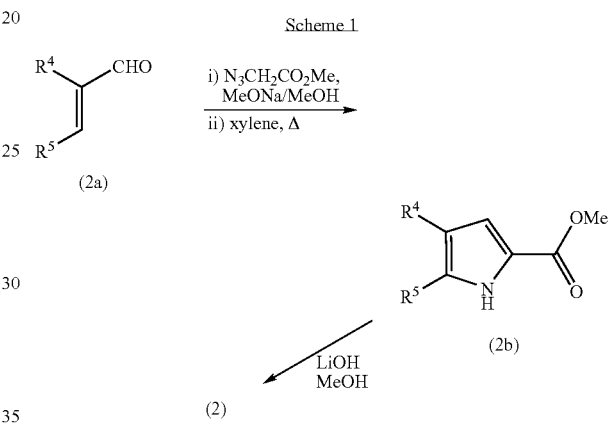

Compounds of formula (2a) are commercially available or they are known compounds or they are prepared by processes known in the art.

The acids of the formula (2), wherein X is N, can be prepared from a compound of the formula (6):

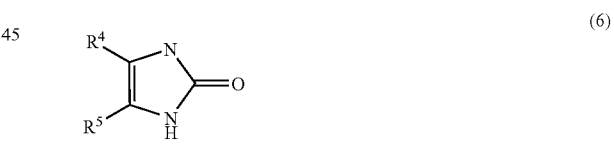

by firstly converting the oxo group to chlorine or bromine with a halogenating agent such as $POCl_3$ or $POBr_3$, in an inert organic solvent such as dichloromethane in a temperature range of ambient temperature to reflux (for example see *Nucleic Acid Chem.* 1991, 4, 24–6), then displacing the chlorine or bromine group with cyanide using a cyanide salt such as potassium cyanide, in an inert organic solvent such as toluene, benzene or xylene, optionally in the presence of a catalyst such as 18-crown-6 (for example see *J. Heterocycl. Chem* 2000, 37(1), 119–126) and finally hydrolysing the cyano group to a carboxy group, with for example, an aqueous acid such as aqueous hydrogen chloride (for example see *Chem. Pharm. Bull.* 1986, 34(9), 3635–43).

Alternatively, a compound of the formula (2) wherein X is N may be formed by reacting the compound of the formula (6) with $(Cl_3CCO)_2O$ and $Cl_3CCO_2H$ in the presence of magnesium chloride using Cl₃CCO₂H as solvent, to form a compound of the formula (7):

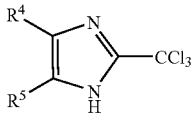
(7)

and then hydrolysing the compound of the formula (7), using, for example, aqueous sodium hydroxide, at a temperature range of ambient temperature to reflux (for example see *J Heterocycl. Chem.* 1980, 17(2), 381–2).

The compound of formula (6) may be prepared from a compound of formula (12) and (13) using conditions known for the Curtius rearrangement (*Tetrahedron* 1999, 55, 6167):

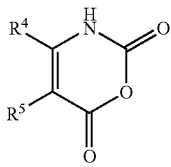
(12)

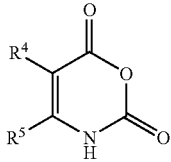
(13)

The compounds of the formula (10) and (11):

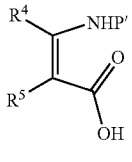
(10)

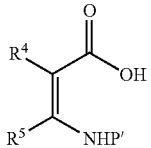
(11)

transform into compounds of the formula (12) and (13) respectively. This transformation either occurs spontaneously or may be induced with acid or base.

Compounds of the formula (10) and (11) may be prepared by introducing a carboxy group into a compound of the formula (8) or (9):

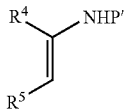
(8)

-continued

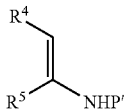
(9)

wherein P' is an amino protecting group such as butoxycarbonyl.

A carboxy group is introduced into the compound of the formula (8) or (9) by reacting an alkyl lithium reagent such as n-butyl lithium, in an inert organic solvent such as THF, at low temperature, for example in the range −10° C. to −78° C. and then forming the compound of the formula (10) or (11) as appropriate by either a) reacting the resulting compound with carbon dioxide; or
b) by reacting with DMF in the temperature range of −10° C. to ambient temperature to form the corresponding aldehyde and oxidizing the aldehyde to carboxy with standard reagents to give the compound of the formula (10) or (11).

Compounds of the formula (8) and (9) may be prepared from a compound of the formula (14) and (15):

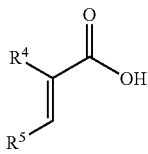
(14)

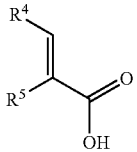
(15)

using conditions known for the Curtius reaction.

Compounds of the formula (14) and (15) may be prepared by oxidizing the corresponding aldehyde using standard oxidizing reagents such as potassium manganate or sodium periodate.

The aldehyde precursor of a compound of the formula (14) or (15) can be prepared using standard techniques known in the art. For example, many compounds of the formula (14) or (15) may be prepared by introducing the appropriate R⁶ and R⁷ into a compound of the formula (16) or (17) as appropriate:

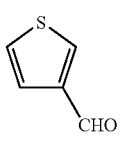
(16)

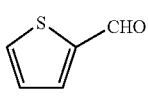
(17)

For example, when $R^6$ and $R^7$ are both chloro a compound of the formula (16) or (17) may be chlorinated with a chlorinating agent such as chlorine in the presence of aluminium chloride or iron (III) chloride, in an inert organic chlorinated solvent such as dichloromethane or 1,2-dichloroethane, followed by treatment with an aqueous base, such as, aqueous sodium hydroxide. The mono chlorinated compound can be formed in the same way.

Compounds of formula (3) may be prepared by reacting an amine of formula (4)

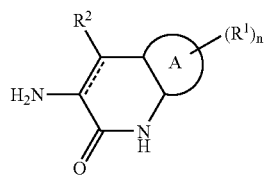

(4)

with $R^3$-L where L is a suitable leaving group (for example chloro, bromo or iodo) in the presence of a base such as sodium hydride in a suitable solvent.

Compounds of the formula (4) wherein A is phenylene and

----- is a single bond may be made from 3-amino-3,4-dihydro-quinolin-2-(1H)-one hydrochloride (J. Med. Chem., 28, 1985, 1511–16). Compounds of the formula (4) wherein A is phenylene and

----- is a double bond may be prepared by the reductive cyclisation of a compound of formula (18), using for example tin (II) chloride in hydrochloric acid, followed by removal of the Boc protecting group, using for example trifluoroacetic acid. Compounds of formula (18) may be prepared by reaction of compounds of formula (19) by reaction with a compound of formula (20) in the presence of a base, for example tetramethylguanidine. Compounds of formula (19) are commercially available or described in the literature.

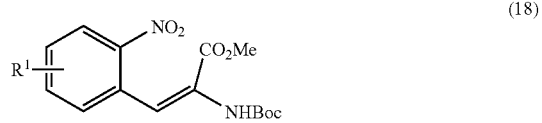

(18)

(19)

(20)

Compounds of the formula (4) wherein A is heterocyclylene can be prepared from cyclisation of suitably functionalised heterocycles. For example, when A is pyridine,

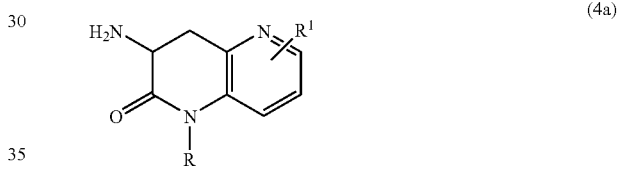

(4a)

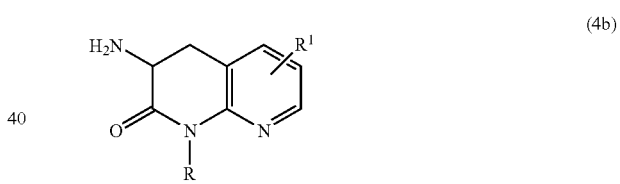

(4b)

compounds of formula (4a) and (4b) may be prepared from an appropriately substituted nitro-methylpyridine or amino-pyridine according to the Schemes 2 and 3:

Scheme 2

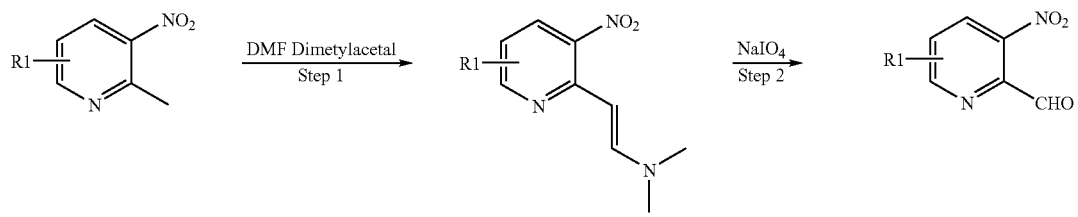

-continued

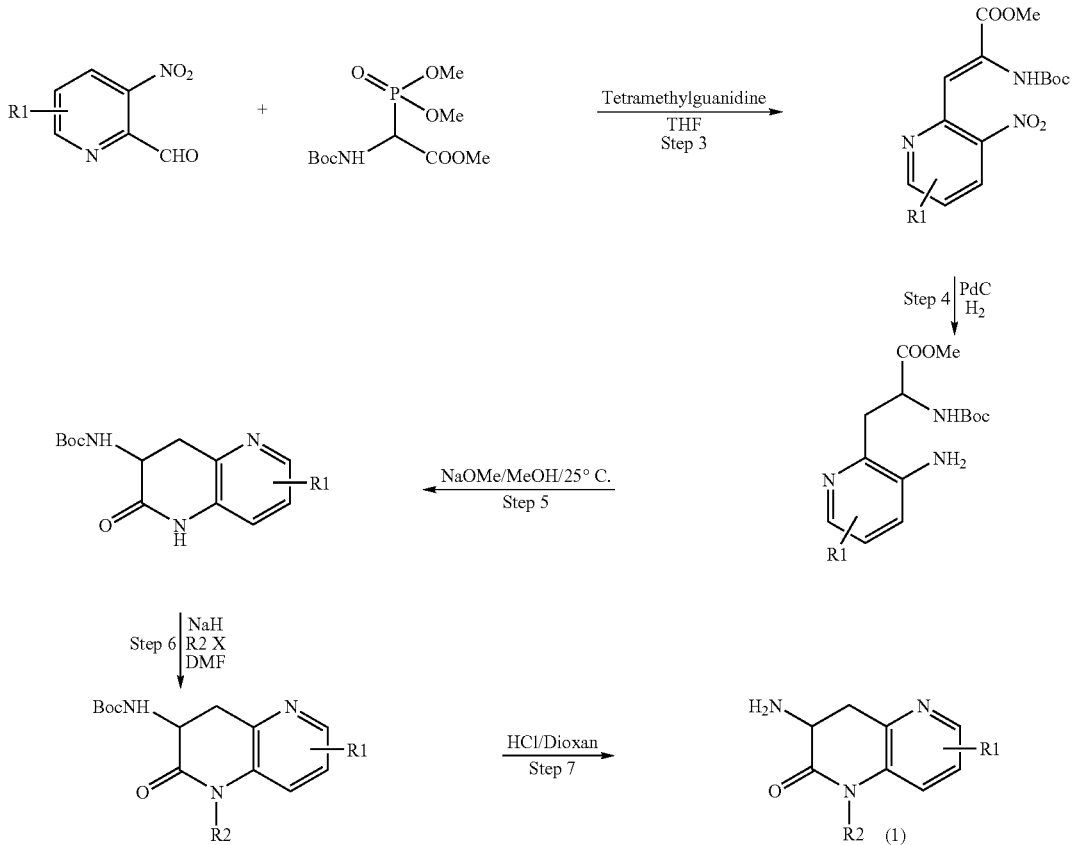

Steps 1 and 2 may be carried out by the process described in Tetrahedron 1998, 54(23), 6311–6318.

Step 3 may be carried out by the method described in Synthesis 1992 (5),487 Assymetric hydrogenation reactions of olefins as shown in Step 4 are well known (see for example, JACS 1993, 115, 10125–10138) and lead to homochiral final products.

Step 5 may alternatively be carried out by hydrolysing the ester and activating the resulting acid with a carbodiimide such as EDCI or DCCI, or by preparing an acid chloride, or activated ester such as an N-hydroxysuccinimide ester. Suitable bases are organic base such as triethylamine or di-isopropylethylamine (DIPEA) or 1,8-diazabicyclo[5.4.0]undec-7-ene (DBU).

In Step 6 X is a leaving group, for example Cl, Br, I, OMesyl. In Step 7 alternative solvents such as dichloromethane or other acids such as trifluoroacetic acid can be used.

Scheme 3

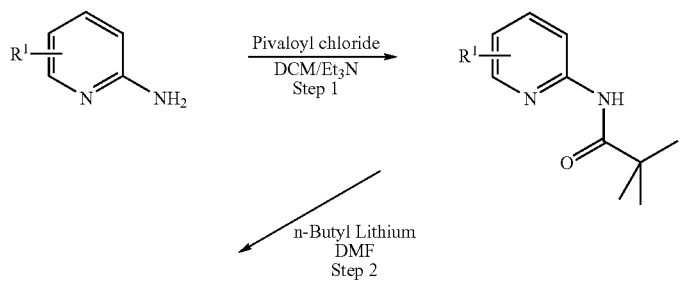

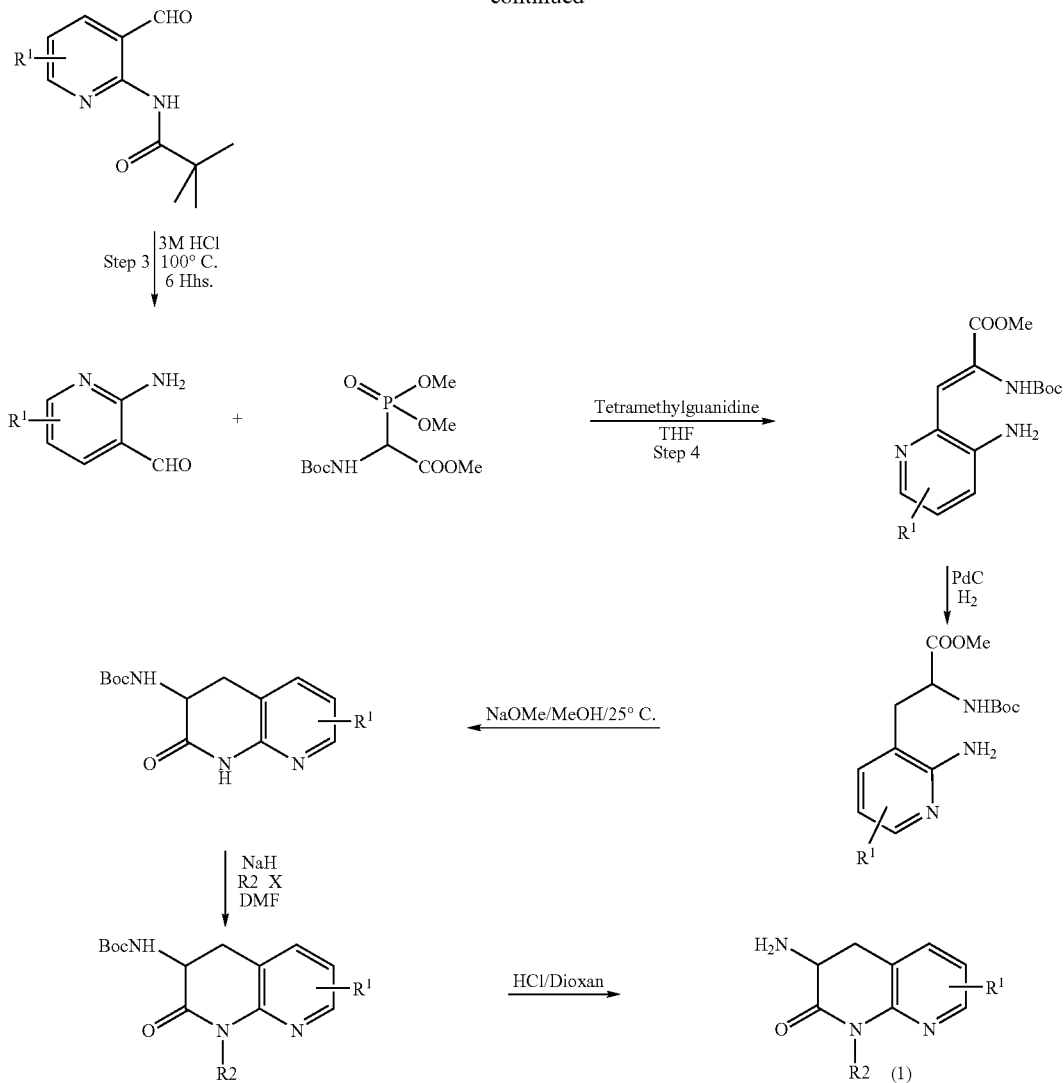

Steps 1, 2, 3 and 4 are described in JOC 1983, 48, 3401–3408.

The processes described above and shown in Schemes 2 and 3 may also be applied to other isomeric pyridines or six membered heterocycles containing more than one nitrogen.

Compounds of the formula (4) wherein A is heteroarylene and there is a bridgehead nitrogen, for example a compound of formula (4c),

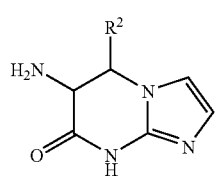

(4c)

may be prepared by cyclisation of a compound of the formula (21):

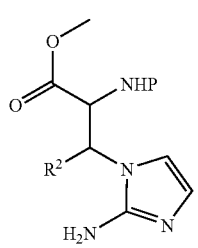

(21)

wherein P is an amino protecting group such as triphenylmethyl. This transformation is induced by heating compounds of the formula (21) to reflux in a solvent, for example, ethanol.

Compounds of the formula (21) may be prepared from a compound of the formula (22) by hydrogenation using a catalyst such as Pd/C at ambient temperature.

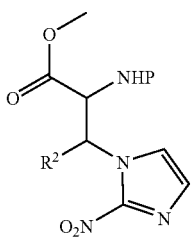

(22)

Compounds of the formula (22) may be prepared from compounds of the formula (23) and (24):

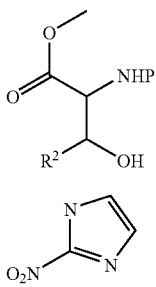

(23)

(24)

using conditions known for the Mitsunobu reaction (*Bull. Chem. Soc. Jpn.,* 1967, 40, 2380). Compounds of the formula (23) and (24) are commercially available.

Compounds of formula (2b) may also be prepared as illustrated in Scheme 4:

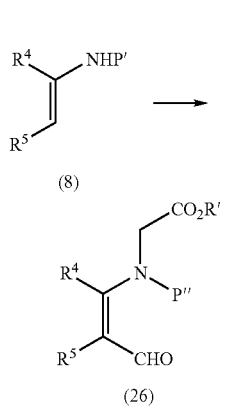

The conversion of compounds of formula (8) into compounds of formula (25) may be carried out by directed ortho lithiation reactions (J. Org. Chem, 2001, volume 66, 3662–3670), for example with n-butyl lithium and (CHO)N(alkyl)$_2$. The protecting group P' in compounds of formula (8) must be suitable directing group for this reaction and may be for example —CO$_2$tBu. Reaction of compounds of formula (25) with LCH$_2$CO$_2$R where L is a leaving group, and replacement of the protecting group P' with an alternative P" (for example —COalkyl) according to standard processes, gives a compound of formula (26). This may be cyclised using a base, for example potassium carbonate or sodium methoxide.

Compounds of the formula (4) wherein A is heteroarylene and there is a bridgehead heteroatom, for example, compounds of the formula (4d) may be made by analogous chemistry to that shown for making compounds of the formula (4c).

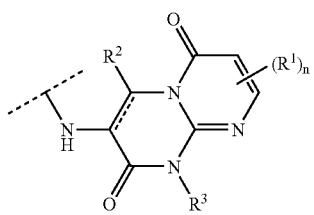

(4d)

It will be appreciated that certain of the various ring substituents in the compounds of the present invention, for example $R^1$, may be introduced by standard aromatic substitution reactions or generated by conventional functional group modifications either prior to or immediately following the processes mentioned above, and as such are included in the process aspect of the invention. Such reactions may convert one compound of the formula (1) into another compound of the formula (1). Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogen group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide.

Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Certain intermediates in the preparation of a compound of the formula (1) are novel and form another aspect of the invention.

As stated hereinbefore the compounds defined in the present invention possesses glycogen phosphorylase inhibitory activity. This property may be assessed, for example, using the procedure set out below.

Assay

The activity of the compounds is determined by measuring the inhibitory effect of the compounds in the direction of glycogen synthesis, the conversion of glucose-1-phosphate into glycogen with the release of inorganic phosphate, as described in EP 0 846 464 A2. The reactions were in 96 well microplate format in a volume of 100 μl. The change in optical density due to inorganic phosphate formation was measured at 620 nM in a Labsystems iEMS Reader MF by the general method of (Nordlie R. C and Arion W. J, Methods of Enzymology, 1966, 619–625). The reaction is in 50 mM HEPES (N-(2-Hydroxyethyl)piperazine-N'-(2-ethanesulfonic acid);4-(2-Hydroxyethyl)piperazine-1-ethanesulfonic acid), 2.5 mM $MgCl_2$, 2.25 mM ethylene glycol-bis(b-aminoethyl ether) N,N,N',N'-tetraacetic acid, 100 mM KCl, 2 mM D-(+)-glucose pH7.2, containing 0.5 mM dithiothreitol, the assay buffer solution, with 0.1 mg type III glycogen, 0.15 ug glycogen phosphorylase a (GPa) from rabbit muscle and 0.5 mM glucose-1-phosphate. GPa is pre-incubated in the assay buffer solution with the type III glycogen at 2.5 mg ml$^{-1}$ for 30 minutes. 40 μl of the enzyme solution is added to 25 μl assay buffer solution and the reaction started with the addition of 25 μl 2 mM glucose-1-phosphate. Compounds to be tested are prepared in 10 μl 10% DMSO in assay buffer solution, with final concentration of 1% DMSO in the assay. The non-inhibited activity of GPa is measured in the presence of 10 μl 10% DMSO in assay buffer solution and maximum inhibition measured in the presence of 30 μM CP320626 (Hoover et al (1998) J Med Chem 41, 2934–8; Martin et al (1998) PNAS 95, 1776–81). The reaction is stopped after 30 min with the addition of 50 μl acidic ammonium molybdate solution, 12 ug ml$^{-1}$ in 3.48% $H_2SO_4$ with 1% sodium lauryl sulphate and 10 ug ml$^{-1}$ ascorbic acid. After 30 minutes at room temperature the absorbency at 620 nm is measured.

The assay is performed at a test concentration of inhibitor of 10 μM or 100 μM. Compounds demonstrating significant inhibition at one or both of these concentrations may be further evaluated using a range of test concentrations of inhibitor to determine an $IC_{50}$, a concentration predicted to inhibit the enzyme reaction by 50%.

Activity is calculated as follows:—

% inhibition=(1−(compound *OD*620−fully inhibited *OD*620)/(non-inhibited rate *OD*620−fully inhibited *OD*620))*100.

*OD*620=optical density at 620 nM.

Typical $IC_{50}$ values for compounds of the invention when tested in the above assay are in the range 100 μM to 1 nM.

The activity of the compounds is alternatively determined by measuring the inhibitory effect of the compounds on glycogen degradation, the production of glucose-1-phosphate from glycogen is monitored by the multienzyme coupled assay, as described in EP 0 846 464 A2, general method of Pesce et al (Pesce, M A, Bodourian, S H, Harris, R C, and Nicholson, J F (1977) Clinical Chemistry 23, 1171–1717). The reactions were in 384 well microplate format in a volume of 50 μl. The change in fluorescence due to the conversion of the co-factor NAD to NADH is measured at 340 nM excitation, 465 nm emission in a Tecan Ultra Multifunctional Microplate Reader. The reaction is in 50 mM HEPES, 3.5 mM $KH_2PO_4$, 2.5 mM $MgCl_2$, 2.5 mM ethylene glycol-bis(b-aminoethyl ether) N,N,N',N'-tetraacetic acid, 100 mM KCl, 8 mM D-(+)-glucose pH7.2, containing 0.5 mM dithiothreitol, the assay buffer solution. Human recombinant liver glycogen phosphorylase α (hrl GPα) 20 nM is pre-incubated in assay buffer solution with 6.25 mM NAD, 1.25 mg type III glycogen at 1.25 mg ml$^{-1}$ the reagent buffer, for 30 minutes. The coupling enzymes, phosphoglucomutase and glucose-6-phosphate dehydrogenase (Sigma) are prepared in reagent buffer, final concentration 0.25 Units per well. 20 μl of the hrl GPa solution is added to 10 μl compound solution and the reaction started with the addition of 20 ul coupling enzyme solution. Compounds to be tested are prepared in 10 μl 5% DMSO in assay buffer solution, with final concentration of 1% DMSO in the assay. The non-inhibited activity of GPα is measured in the presence of 10 μl 5% DMSO in assay buffer solution and maximum inhibition measured in the presence of 5 mgs ml$^{-1}$ N-ethylmaleimide. After 6 hours at 30° C. Relative Fluoresence Units (RFUs) are measured at 340 nM excitation, 465 nm emission.

The assay is performed at a test concentration of inhibitor of 10 μM or 100 μM. Compounds demonstrating significant inhibition at one or both of these concentrations may be further evaluated using a range of test concentrations of inhibitor to determine an $IC_{50}$, a concentration predicted to inhibit the enzyme reaction by 50%.

Activity is calculated as follows:—

% inhibition=(1−(compound RFUs−fully inhibited RFUs)/(non-inhibited rate RFUs−fully inhibited RFUs))*100.

Typical $IC_{50}$ values for compounds of the invention when tested in the above assay are in the range 100 μM to 1 nM. For example, Example 14 gave an $IC_{50}$ value of 2.7 μM.

The inhibitory activity of compounds was further tested in rat primary hepatocytes. Rat hepatocytes were isolated by the collagenase perfusion technique, general method of Seglen (P. O. Seglen, Methods Cell Biology (1976) 13 29–83). Cells were cultured on Nunclon six well culture plates in DMEM (Dulbeco's Modified Eagle's Medium) with high level of glucose containing 10% foetal calf serum, NEAA (non essential amino acids), Glutamine, penicillin/streptomycin ((100 units/100 ug)/ml) for 4 to 6 hours. The hepatocytes were then cultured in the DMEM solution without foetal calf serum and with 10 nM insulin and 10 nM dexamethasone. Experiments were initiated after 18–20 hours culture by washing the cells and adding Krebs-Henseleit bicarbonate buffer containing 2.5 mM $CaCl_2$ and 1% gelatin. The test compound was added and 5 minutes later the cells were challenged with 25 nM glucagon. The Krebs-Henseleit solution was removed after 60 min incubation at 37° C., 95% $O_2$/5% $CO_2$ and the glucose concentration of the Krebs-Henseleit solution measured.

According to a further aspect of the invention there is provided a pharmaceutical composition which comprises a compound of the formula (1), or a pharmaceutically acceptable salt or in vivo hydrolysable ester thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The compound of formula (1) will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The inhibition of glycogen phosphorylase activity described herein may be applied as a sole therapy or may involve, in addition to the subject of the present invention, one or more other substances and/or treatments. Such conjoint treatment may be achieved by way of the simultaneous, sequential or separate administration of the individual components of the treatment. Simultaneous treatment may be in a single tablet or in separate tablets. For example in the treatment of diabetes mellitus chemotherapy may include the following main categories of treatment:

1) Insulin and insulin analogues;
2) Insulin secretagogues including sulphonylureas (for example glibenclamide, glipizide) and prandial glucose regulators (for example repaglinide, nateglinide);
3) Insulin sensitising agents including PPARg agonists (for example pioglitazone and rosiglitazone);
4) Agents that suppress hepatic glucose output (for example metformin).
5) Agents designed to reduce the absorption of glucose from the intestine (for example acarbose);
6) Agents designed to treat the complications of prolonged hyperglycaemia;
7) Anti-obesity agents (for example sibutramine and orlistat);
8) Anti-dyslipidaemia agents such as, HMG-CoA reductase inhibitors (statins, eg pravastatin); PPARα agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
9) Antihypertensive agents such as, β blockers (eg atenolol, inderal); ACE inhibitors (eg lisinopril); Calcium antagonists (eg. nifedipine); Angiotensin receptor antagonists (eg candesartan), α antagonists and diuretic agents (eg. furosemide, benzthiazide);
10) Haemostasis modulators such as, antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and Low molecular weight analogues, hirudin) and warfarin; and
11) Anti-inflammatory agents, such as non-steroidal anti-inflammatory drugs (eg. aspirin) and steroidal anti-inflammatory agents (eg. cortisone).

According to a further aspect of the present invention there is provided a compound of the formula (1), or a pharmaceutically acceptable salt or in vivo hydrolysable ester thereof, as defined hereinbefore, for use in a method of treatment of a warm-blooded animal such as man by therapy.

According to an additional aspect of the invention there is provided a compound of the formula (1), or a pharmaceutically acceptable salt or in vivo hydrolysable ester thereof, as defined hereinbefore, for use as a medicament.

According to an additional aspect of the invention there is provided a compound of the formula (1), or a pharmaceutically acceptable salt or in vivo hydrolysable ester thereof, as defined hereinbefore, for use as a medicament in the treatment of type 2 diabetes, insulin resistance, syndrome X, hyperinsulinaemia, hyperglucagonaemia, cardiac ischaemia or obesity in a warm-blooded animal such as man.

According to this another aspect of the invention there is provided the use of a compound of the formula (1), or a pharmaceutically acceptable salt or in vivo hydrolysable ester thereof, as defined hereinbefore in the manufacture of a medicament for use in the treatment of type 2 diabetes, insulin resistance, syndrome X, hyperinsulinaemia, hyperglucagonaemia, cardiac ischaemia or obesity in a warm-blooded animal such as man.

According to this another aspect of the invention there is provided the use of a compound of the formula (1), or a pharmaceutically acceptable salt or in vivo hydrolysable ester thereof, as defined hereinbefore in the manufacture of a medicament for use in the treatment of type 2 diabetes in a warm-blooded animal such as man.

According to a further feature of this aspect of the invention there is provided a method of producing a glycogen phosphorylase inhibitory effect in a warm-blooded animal, such as man, in need of such treatment which comprises administering to said animal an effective amount of a compound of formula (1).

According to this further feature of this aspect of the invention there is provided a method of treating type 2 diabetes, insulin resistance, syndrome X, hyperinsulinaemia, hyperglucagonaemia, cardiac ischaemia or obesity in a warm-blooded animal, such as man, in need of such treatment which comprises administering to said animal an effective amount of a compound of formula (1).

According to this further feature of this aspect of the invention there is provided a method of treating type 2 diabetes in a warm-blooded animal, such as man, in need of such treatment which comprises administering to said animal an effective amount of a compound of formula (1).

As stated above the size of the dose required for the therapeutic or prophylactic treatment of a particular cell-proliferation disease will necessarily be varied depending on the host treated, the route of administration and the severity of the illness being treated. A unit dose in the range, for example, 1–100 mg/kg, preferably 1–50 mg/kg is envisaged.

In addition to their use in therapeutic medicine, the compounds of formula (1) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

Each Example is independently provided as a further aspect of the invention.

EXAMPLES

The invention will now be illustrated by the following non-limiting examples in which, unless stated otherwise:

(i) temperatures are given in degrees Celsius (°C.); operations were carried out at room or ambient temperature, that is, at a temperature in the range of 18–25° C. and under an atmosphere of an inert gas such as argon;

(ii) organic solutions were dried over anhydrous magnesium sulphate; evaporation of solvent was carried out using a rotary evaporator under reduced pressure (600–4000 Pascals; 4.5–30 mmHg) with a bath temperature of up to 60° C.;

(iii) chromatography means flash chromatography on silica gel; thin layer chromatography (TLC) was carried out on silica gel plates; where a Bond Elut column is referred to, this means a column containing 10 g or 20 g or 50 g of silica of 40 micron particle size, the silica being contained in a 60 ml disposable syringe and supported by a porous disc, obtained from Varian, Harbor City, Calif., USA under the name "Mega Bond Elut SI"; "Mega Bond Elut" is a trademark; where a Biotage cartridge is referred to this means a cartridge containing KP-SIL™ silica, 60μ, particle size 32–63 mM, supplied by Biotage, a division of Dyax Corp., 1500 Avon Street Extended, Charlottesville, Va. 22902, USA;

(iv) in general, the course of reactions was followed by TLC and reaction times are given for illustration only;

(v) yields are given for illustration only and are not necessarily those which can be obtained by diligent process development; preparations were repeated if more material was required;

(vi) where given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$\delta_6$) as solvent unless otherwise indicated, other solvents (where indicated in the text) include deuterated chloroform $CDCl_3$;

(vii) chemical symbols have their usual meanings; SI units and symbols are used;

(viii) reduced pressures are given as absolute pressures in Pascals (Pa); elevated pressures are given as gauge pressures in bars;

(ix) solvent ratios are given in volume: volume (v/v) terms;

(x) mass spectra (MS) were run with an electron energy of 70 electron volts in the chemical ionisation (CI) mode using a direct exposure probe; where indicated ionisation was effected by electron impact (EI), fast atom bombardment (FAB) or electrospray (ESP); values for m/z are given; generally, only ions which indicate the parent mass are reported and unless otherwise stated the value quoted is $(M-H)^-$;

(xi) The following abbreviations are used:

| | |
|---|---|
| SM | starting material; |
| EtOAc | ethyl acetate; |
| MeOH | methanol; |
| EtOH | ethanol; |
| DCM | dichloromethane; |
| HOBT | 1-hydroxybenzotriazole; |
| DIPEA | di-isopropylethylamine; |
| EDCI | 1-ethyl-3-(3-dimethylaminopropyl)carbodi-imide hydrochloride; |
| $Et_2O$ | diethyl ether; |
| THF | tetrahydrofuran; |
| DMF | N,N-dimethylformamide; |
| HATU | O-(7-Azabenzotriazol-1-yl)-N,N,N',N'-tetramethyluroniumhexafluorophosphate |
| DMAP | 4-dimethylaminopyridine |
| TBAF | tetrabutylammonium fluoride |
| TFA | trifluoroacetic acid |

Certain intermediates described hereinafter within the scope of the invention may also possess useful activity, and are provided as a further feature of the invention.

Example 1

2-Chloro-N-[1-(methoxycarbonylmethyl)-2-oxo-1,2,3,4-tetrahydroquinolin-3-yl]-6H-thieno[2,3-b]pyrrole-5-carboxamide

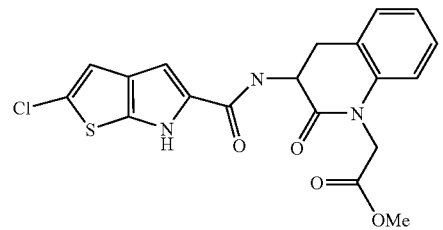

5-Carboxy-2-chloro-6H-thieno[2,3-b]pyrrole (Method 9; 5.07 g, 25.2 mmol), HOBT (3.40 g, 25.2 mmol), anhydrous DMF (100 mL) and finally EDCI (4.82 g, 25.2 mmol) were added to methyl 3-amino-2-oxo-3,4-dihydroquinolin-1 (2H)-yl)acetate (Method 1; 5.89 g, 25.2 mmol) and the reaction was stirred for 18 h. The reaction was then diluted with water (200 mL) and stirred vigorously for 30 min. The resultant precipitate was filtered and washed with water (50 mL), EtOAc (2×20 mL) and Et$_2$O (2×10 mL). The collected solid was further dried under high vacuum for 6 h to furnish the title compound (8.00 g, 76%) as a pale yellow solid.

$^1$H NMR 3.15 (m, 2H), 3.64 (s, 3H), 4.74 (m, 3H), 7.18 (m, 6H), 8.58 (d, 1H), 11.91 (s, 1H); MS m/z MH$^+$ 418, 420.

Example 2

N-[1-(Carboxymethyl)-2-oxo-1,2,3,4-tetrahydroquinolin-3-yl]-2-chloro-6H-thieno [2,3-b]pyrrole-5-carboxamide

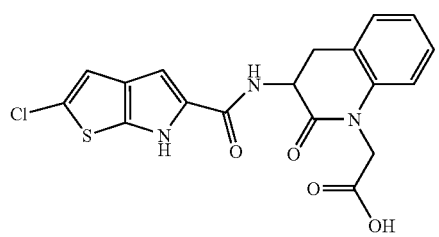

LiOH (1.41 g, 33.6 mmol) in H$_2$O (16.5 mL) was added to a stirring solution of 2-chloro-N-[1-(methoxycarbonylmethyl)-2-oxo-1,2,3,4-tetrahydroquinolin-3-yl]-6H-thieno[2,3-b]pyrrole-5-carboxamide (Example 1; 7.00 g, 16.8 mmol) in THF (88 mL) and the reaction was stirred for 2 h. The reaction was quenched by addition of 1M aqueous HCl (200 mL) and EtOAc (400 mL) and the organic layer was dried (MgSO$_4$), filtered and evaporated. The resultant white foam was triturated with hot Et$_2$O (100 mL) cooled, filtered and dried to afford the title compound (6.00 g, 89%) as a white solid.

$^1$H NMR 3.14 (m, 2H), 4.52 (d, 1H), 4.75 (m, 2H), 7.03 (m, 3H), 7.18 (s, 1H), 7.27 (m, 2H), 7.57 (d, 1H), 11.90 (s, 1H), 12.89 (br. s, 1H); MS m/z MH$^+$ 404, 406.

Example 3

2-Chloro-N-[1-(carbamoylmethyl)-2-oxo-1,2,3,4-tetrahydroquinolin-3-yl]-6H-thieno [2,3-b]pyrrole-5-carboxamide

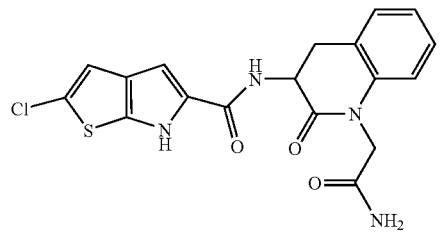

Triethylamine (38 μL, 0.27 mmol) then ethyl chloroformate (26.1 μL, 0.27 mmol) were added to N-[1-(carboxymethyl)-2-oxo-1,2,3,4-tetrahydroquinolin-3-yl]-2-chloro-6H-thieno[2,3-b]pyrrole-5-carboxamide (Example 2; 100 mg, 0.25 mmol) in anhydrous THF (2 mL) at 0° C. followed by stirring for 1 h. Concentrated aqueous NH$_3$ (1 mL) was added and the reaction was stirred for a further 1 h. Water (20 mL) and EtOAc (40 mL) were added and the organic layer was separated, washed with 1M HCl (20 mL) and the organic layer was dried (MgSO$_4$), filtered and evaporated. The residue was purified by column chromatography (MeOH:DCM 1:19) to afford the title compound (56 mg, 56%) as a white solid.

$^1$H NMR 3.15 (m, 2H), 4.23 (d, 1H), 4.67 (d, 1H), 4.82 (m, 1H), 6.88 (d, 1H), 7.05 (m, 2H), 7.14 (s, 2H), 7.24 (m, 2H), 7.54 (s, 1H), 8.51 (d, 1H), 11.91 (s, 1H); MS m/z MH$^+$ 403, 405.

Examples 4–7

The following examples were synthesised by an analogous method to Example 3:

Example 4

2-Chloro-N-[1-(N,N-dimethylcarbamoylmethyl)-2-oxo-1,2,3,4-tetrahydroquinolin-3-yl]-6H-thieno [2,3-b]pyrrole-5-carboxamide Example 5

2-Chloro-N-[1-(N-methylcarbamoylmethyl)-2-oxo-1,2,3,4-tetrahydroquinolin-3-yl]-6H-thieno[2,3-b]pyrrole-5-carboxamide Example 6

2-Chloro-N-[1-(N-hydroxycarbamoylmethyl)-2-oxo-1,2,3,4-tetrahydroquinolin-3-yl]-6H-thieno[2,3-b]pyrrole-5-carboxamide Example 7

2-Chloro-N-{1-[N-(2-hydroxyethyl)carbamoylmethyl]-2-oxo-1,2,3,4-tetrahydroquinolin-3-yl}-6H-thieno[2,3-b]pyrrole-5-carboxamide

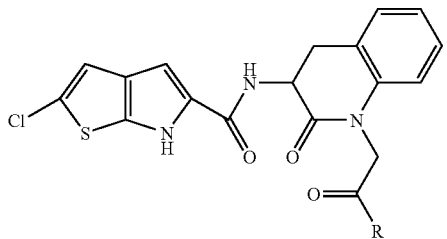

| Example | NR¹R² | ¹H NMR | m/z MH⁺ |
|---|---|---|---|
| 4 | \N/ methyl, methyl | 2.84 (s, 3H), 3.03 (dd, 1H), 3.10 (s, 3H), 3.19 (app. t, 1H), 4.58 (d, 1H), 4.74 (m, 1H), 4.93 (d, 1H), 6.87 (d, 1H), 7.03 (t, 1H), 7.09 (s, 1H), 7.18 (s, 1H), 7.25 (m, 2H), 8.56 (d, 1H), 11.95 (s, 1H). | 431, 433 |
| 5 | \NH/ methyl | 2.60 (s, 3H), 3.05 (dd, 1H), 3.16 (app. t, 1H), 4.37 (d, 1H), 4.68 (d, 1H), 4.87 (m, 1H), 6.88 (d, 1H), 7.04 (t, 1H), 7.10 (s, 1H), 7.18 (s, 1H), 7.27 (m, 2H), 8.00 (m, 1H), 8.52 (d, 1H), 11.91 (s, 1H). | 417, 419 |
| 6 | HO-N(H)-CH₃ | 3.02 (dd, 1H), 3.17 (app. t, 1H), 4.30 (d, 1H), 4.61 (d, 1H), 4.84 (m, 1H), 6.92 (d, 1H), 7.05 (t, 1H), 7.09 (s, 1H), 7.27 (m, 2H), 8.52 (d, 1H), 8.90 (s, 1H), 10.72 (s, 1H), 11.92 (s, 1H). | 419, 421 |
| 7 | HO-CH₂CH₂-N(H)-CH₃ | 3.04 (m, 1H), 3.10 (m, 3H), 3.39 (m, 2H), 4.32 (d, 1H), 4.73 (m, 3H), 6.89 (d, 1H), 7.03 (t, 1H), 7.10 (s, 1H), 7.17 (s, 1H), 7.27 (app. d, 2H), 8.09 (t, 1H), 8.53 (d, 1H), 11.92 (s, 1H). | 447, 449 |

Example 8

2-Chloro-N-[1-(2-hydroxyethyl)-2-oxo-1,2,3,4-tetrahydroquinolin-3-yl]-6H-thieno[2,3-b]pyrrol-5-ylcarboxamide

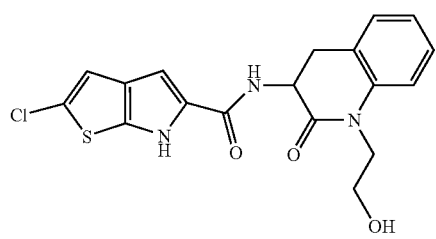

Triethylamine (0.76 mL, 5.47 mmol) then ethyl chloroformate (0.52 mL, 5.47 mmol) were added to N-[1-(carboxymethyl)-2-oxo-1,2,3,4-tetrahydroquinolin-3-yl]-2-chloro-6H-thieno[2,3-b]pyrrole-5-carboxamide (Example 2; 2.0 g, 4.97 mmol) in anhydrous THF (40 mL) at 0° C. followed by stirring for 1 h. LiBH₄ (2.0 M in THF, 3.1 mL, 6.21 mmol) was added slowly and the mixture stirred for a further 30 min. The reaction was carefully quenched with 1M HCl (200 mL) and EtOAc (400 mL) and the organic layer was further washed with sat. aqueous NaHCO₃ (100 mL), brine (100 mL), dried (MgSO₄), filtered and evaporated. The residue was triturated with refluxing Et₂O (30 mL) and after cooling the solid was filtered and dried to afford the title compound (1.70 g, 88%) as a white solid.

¹H NMR 3.04 (m, 2H), 3.59 (m, 2H), 3.91 (m, 1H), 4.01 (m, 1H), 4.72 (m, 1H), 4.83 (m, 1H), 7.18 (m, 6H), 8.48 (d, 1H), 11.90 (s, 1H); MS m/z MH⁺ 390, 392.

Example 9

2-Chloro-N-[1-(2,3-dihydroxypropyl)-2-oxo-1,2,3,4-tetrahydroquinolin-3-yl]-6H-thieno[2,3-b]pyrrole-5-carboxamide

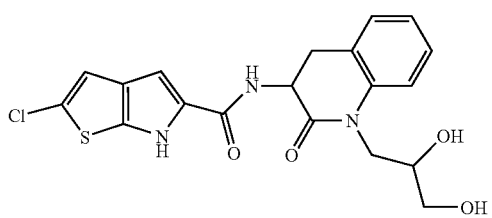

6M Aqueous HCl (1.47 mL) was added to N-{1-(2,2-dimethyl-1,3-dioxolan-4-ylmethyl)-2-oxo-1,2,3,4-tetrahydroquinolin-3-yl}-2-chloro-6H-thieno[2,3-b]pyrrole-5-carboxamide (Method 3; 340 mg, 7.45 mmol) in THF (14 mL) and the reaction was stirred for 4 h. The reaction was quenched by addition of triethylamine (1.5 mL) then diluted with water (30 mL) and EtOAc (40 mL). The organic layer was separated, dried (MgSO$_4$), filtered and evaporated. The residue was triturated with hot Et$_2$O (10 mL) and after cooling was filtered and dried to afford the title compound (260 mg, 83%) as white solid.

$^1$H NMR 3.07 (m, 3H), 3.81 (m, 2H), 4.01 (m, 2H), 4.71 (m, 3H), 7.16 (m, 6H), 8.45 (app. d, 1H), 11.91 (s, 1H); MS m/z MH$^+$ 420, 422.

Example 10

2-Chloro-N-{1-[(2,2-dimethyl-1,3-dioxolan-4(S)-yl)methyl]-2-oxo-1,2,3,4-tetrahydroquinolin-3(R,S)-yl}-6H-thieno[2,3-b]pyrrole-5-carboxamide

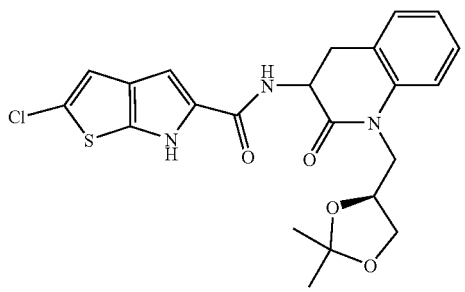

The title compound was prepared as described for Method 2 using [(4R)-2,2-dimethyl-1,3-dioxolan-4-yl]methyl methanesulfonate (*J. Med. Chem.*, 26, 1983 950–57), followed by the coupling procedure of Method 3.

$^1$H NMR 1.32 (s, 1.5H), 1.33 (s, 1.5H), 1.37 (s, 1.5H), 1.42 (s, 1.5H), 2.88 (m, 1H), 3.63 (m, 1H), 3.78 (app. t, 1H), 3.90 (dd, 0.5H), 4.04 (dd, 0.5H), 4.14 (m, 1H), 4.33 (m, 2H), 4.68 (m, 1H), 6.82 (m, 2H), 7.10 (m, 1H), 7.27 (m, 4H), 10.94 (br. s, 1H); MS m/z MNa$^+$ 482, 484.

Example 11

2-Chloro-N-[1-(2(S),3-dihydroxypropyl)-2-oxo-1,2,3,4-tetrahydroquinolin-3(R,S)-yl]-6H-thieno [2,3-b]pyrrole-5-carboxamide

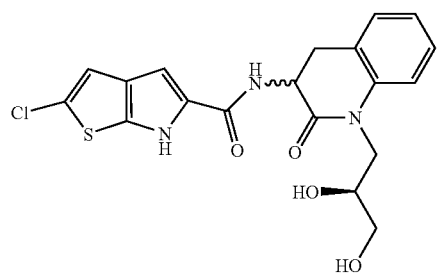

The title compound was prepared (as a mixture of diastereoisomers) by acid hydrolysis as described for Example 9 starting with 2-chloro-N-[1-(2,2-dimethyl-1,3-dioxolan-4(S)-ylmethyl)-2-oxo-1,2,3,4-tetrahydroquinolin-3 (R,S)-yl]-6H-thieno[2,3-b]pyrrole-5-carboxamide (Example 10).

$^1$H NMR 3.07 (m, 3H), 3.81 (m, 2H), 4.01 (m, 2H), 4.71 (m, 3H), 7.16 (m, 6H), 8.45 (app. d, 1H), 11.91 (s, 1H); MS m/z MH$^+$ 420, 422.

Purification of the product by HPLC afforded the two individual diastereoisomers 2-chloro-N-[1-(2(S),3-dihydroxypropyl)-2-oxo-1,2,3,4-tetrahydroquinolin-3(R)-yl]-6H-thieno[2,3-b]pyrrole-5-carboxamide, and 2-chloro-N-[1-(2(S),3-dihydroxypropyl)-2-oxo-1,2,3,4-tetrahydroquinolin-3(S)-yl]-6H-thieno[2,3-b]pyrrole-5-carboxamide as white solids (stereochemistry not assigned):

First Eluting:

$^1$H NMR 3.10 (m, 2H), 3.25 (m, 2H), 3.72 (m, 1H), 3.88 (dd, 1H), 4.03 (dd, 1H), 4.58 (t, 1H), 4.69 (q, 1H), 4.78 (d, 1H), 7.04 (m, 2H), 7.16 (s, 1H), 7.28 (m, 3H), 8.47 (d, 1H), 11.93 (s, 1H); MS m/z 420

Second Eluting:

$^1$H NMR 2.98 (dd, 1H), 3.12 (t, 1H), 3.38 (t, 2H), 3.80 (m, 2H), 3.99 (q, 1H), 4.63 (t, 1H), 4.72 (m, 1H), 4.87 (d, 1H), 7.03 (t, 1H), 7.10 (s, 1H), 7.17 (s, 1H), 7.26 (m, 2H), 7.36 (d, 1H), 8.50 (d, 1H), 11.95 (s, 1H); MS m/z 420

Example 12

2-Chloro-N-[1-(2,2-dimethyl-1,3-dioxolan-4(R)-ylmethyl)-2-oxo-1,2,3,4-tetrahydroquinolin-3(R,S)-yl]-6H-thieno[2,3-b]pyrrole-5-carboxamide

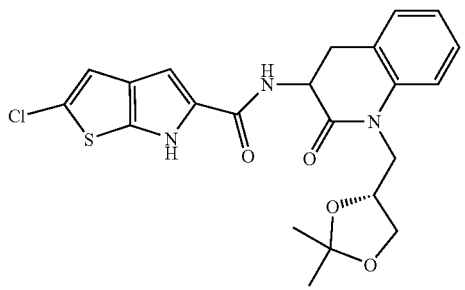

The title compound was prepared as described for Method 2 using [(4S)-2,2-dimethyl-1,3-dioxolan-4-yl]methyl methanesulfonate (*J. Org. Chem,* 64, 1999 6782–6790), followed by the coupling procedure of Method 3.

$^1$H NMR 1.32 (s, 1.5H), 1.33 (s, 1.5H), 1.37 (s, 1.5H), 1.42 (s, 1.5H), 2.88 (m, 1H), 3.63 (m, 1H), 3.78 (app. t, 1H), 3.90 (dd, 0.5H), 4.04 (dd, 0.5H), 4.14 (m, 1H), 4.33 (m, 2H), 4.68 (m, 1H), 6.82 (m, 2H), 7.10 (m, 1H), 7.27 (m, 4H), 10.94 (br. s, 1H); MS m/z MNa$^+$ 482, 484.

Example 13

2-Chloro-N-[1-(2(R),3-dihydroxypropyl)-2-oxo-1,2,3,4-tetrahydroquinolin-3(R,S)-yl]-6H-thieno [2,3-b]pyrrole-5-carboxamide

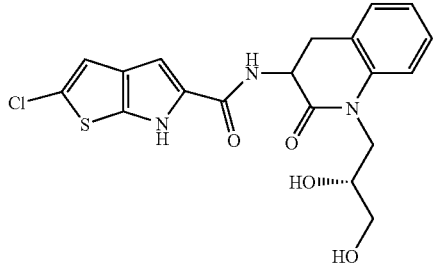

The title compound was prepared by acid hydrolysis as described for Example 9 starting with 2-chloro-N-[1-(2,2-dimethyl-1,3-dioxolan-4(R)-ylmethyl)-2-oxo-1,2,3,4-tetrahydroquinolin-3 (R,S)-yl]-6H-thieno[2,3-b]pyrrole-5-carboxamide (Example 12).

$^1$H NMR 3.07 (m, 3H), 3.81 (m, 2H), 4.01 (m, 2H), 4.71 (m, 3H), 7.16 (m, 6H), 8.45 (app. d, 1H), 11.91 (s, 1H); MS m/z MH$^+$ 420, 422.

Purification of the product by HPLC afforded the two individual diastereoisomers 2-chloro-N-{(3R)-1-[(2R)-2,3-dihydroxypropyl]-2-oxo-1,2,3,4-tetrahydroquinolin-3-yl}-6H-thieno[2,3-b]pyrrole-5-carboxamide, and 2-chloro-N-{(3R)-1-[(2S)-2,3-dihydroxypropyl]-2-oxo-1,2,3,4-tetrahydroquinolin-3-yl}-6H-thieno[2,3-b]pyrrole-5-carboxamide, as white solids (stereochemistry not assigned).

First Eluting:
$^1$H NMR 3.10 (m, 2H), 3.25 (m, 2H), 3.72 (m, 1H), 3.88 (dd, 1H), 4.03 (dd, 1 H), 4.58 (t, 1H), 4.69 (q, 1H), 4.78 (d, 1H), 7.04 (m, 2H), 7.16 (s, 1H), 7.28 (m, 3H), 8.47 (d, 1H), 11.93 (s, 1H); MS m/z 420

Second Eluting:
$^1$H NMR 2.98 (dd, 1H), 3.12 (t, 1H), 3.38 (t, 2H), 3.80 (m, 2H), 3.99 (q, 1 H), 4.63 (t, 1H), 4.72 (m, 1H), 4.87 (d, 1H), 7.03 (t, 1H), 7.10 (s, 1H), 7.17 (s, 1H), 7.26 (m, 2H), 7.36 (d, 1H), 8.50 (d, 1H), 11.95 (s, 1H); MS m/z 420, 422

Example 14

2-Chloro-N-{1-[2-(4-hydroxypiperidin-1-yl)-2-oxo-ethyl]-2-oxo-1,2,3,4-tetrahydroquinolin-3-yl}-6H-thieno[2,3-b]pyrrole-5-carboxamide

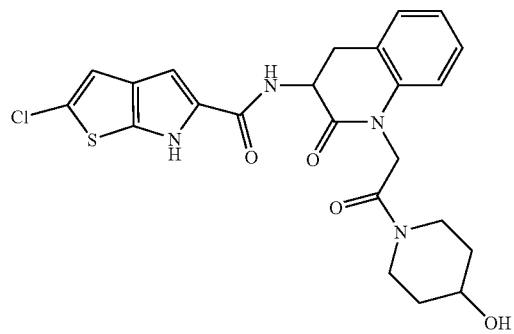

4-Dimethylaminopyridine (5 mg, 0.038 mmol) and 4-hydroxypiperidine (42 mg, 0.41 mmol) were added to a suspension of N-[1-(carboxymethyl)-2-oxo-1,2,3,4-tetrahydroquinolin-3-yl]-2-chloro-6H-thieno[2,3-b]pyrrole-5-carboxamide (Example 2; 150 mg, 0.38 mmol) and EDCI (79 mg, 0.41 mmol) in THF (0.5 mL) under an inert atmosphere. DMF (0.5 mL) was added and the mixture stirred at ambient temperature for 18 h. After pouring into water (10 mL) the resultant solid was filtered off and washed with 1M HCl aq. and water. Chromatography on silica gel (eluent gradient of $CH_2Cl_2$ to MeOH:$CH_2Cl_2$ (1:9)) afforded the title compound (109 mg, 59%) as an off white solid.

$^1$H NMR (400 MHz) 1.20–1.52 (m, 2H), 1.65–1.90 (m, 2H), 3.05 (m, 2H), 3.27(m, 2H), 3.80 (m, 3H), 4.64 (dd, 1H), 4.75 (m, 2H), 4.96 (dd, 1H), 6.89 (d, 1H), 7.04 (t, 1H), 7.11 (s, 1H), 7.19 (s, 1H), 7.28 (t, 1H), 8.54 (d, 1H), 11.93 (s, 1H); MS m/z MH$^+$ 487, 489

Examples 15–17

The following examples were synthesised by an analogous method to Example 14

Example 15

2-Chloro-N-{1-[N-(1,3-dihydroxyprop-2-yl)carbamoylmethyl]-2-oxo-1,2,3,4-tetrahydroquinolin-3-yl}-6H-thieno[2,3-b]pyrrole-5-carboxamide

Example 16

2-Chloro-N-{1-[N-(2-Methoxyethyl)carbamoylmethyl]-2-oxo-1,2,3,4-tetrahydroquinolin-3-yl}-6H-thieno [2,3-b]pyrrole-5-carboxamide

Example 17

2-Chloro-N-(1-{2-[(3a,6a-cis)-2,2-dimethyltetrahydro-5H-[1,3]dioxolo[4,5-c]pyrrol-5-yl]-2-oxoethyl}-2-oxo-1,2,3,4-tetrahydroquinolin-3-yl)-6H-thieno[2,3-b]pyrrole-5-carboxamide

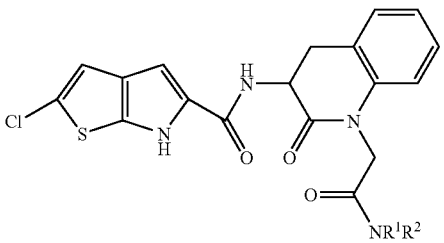

| Example | NR¹R² | ¹H NMR (400 MHz) | m/z | SM (amine) |
|---|---|---|---|---|
| 15 | HN⌇⌇OH / OH | 3.05 (dd, 1H), 3.18 (dd, 1H), 3.42 (m, 4H), 3.73 (m, 1H), 4.40 (d, 1H), 4.63 (m, 2H), 4.77 (m, 2H), 6.93 (d, 1H), 7.05 (t, 1H), 7.11 (s, 1H), 7.19 (s, 1H), 7.28 (t, 1H), 7.88 (d, 1H), 8.55 (d, 1H), 11.94 (s, 1H). | 477, 479 | commercial |
| 16 | HN⌇⌇O⌇ | 3.05 (dd, 1H), 3.25 (m, 9H), 4.33 (d, 1H), 4.73 (d, 1H), 4.85 (m, 1H), 6.90 (d, 1H), 7.06 (t, 1H), 7.11 (s, 1H), 7.19 (s, 1H), 7.29 (t, 1H), 8.20 (t, 1H), 8.54 (d, 1H), 11.94 (s, 1H). | 461, 463 | commercial |
| 17 | (bicyclic dioxolopyrrolidine) | 1.28, 1.29, 1.39, 1.42 (4 × s, 6H), 3.05 (dd, 1H), 3.19 (m, 2H), 3.61 (quintet, 1H), 3.74 (dd, 1H), 3.88 (dd, 1H), 4.59 (dd, 1H), 4.84 (m, 4H), 6.89 (t, 1H), 7.05 (t, 1H), 7.11 (s, 1H), 7.19 (s, 1H), 7.24 (t, 1H), 7.30 (d, 1H), 8.56 (d, 1H), 11.94 (s, 1H). | 529, 531 | Org. Lett., 3, 2001 456–468 |

Example 18

2-Chloro-N-(1-{2-[(cis)-3,4-dihydroxypyrrolidin-1-yl]-2-oxoethyl}-2-oxo-1,2,3,4-tetrahydroquinolin-3-yl)-6H-thieno[2,3-b]pyrrole-5-carboxamide

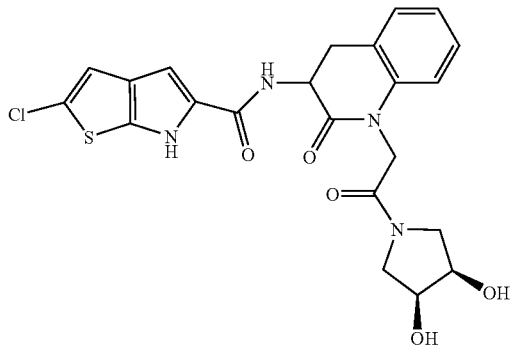

1M HCl aq. (0.46 mL, 0.46 mmol) was added to 2-chloro-N-(1-{2-[(3a,6a-cis)-2,2-dimethyltetrahydro-5H-[1,3]dioxolo[4,5-c]pyrrol-5-yl]-2-oxoethyl}-2-oxo-1,2,3,4-tetrahydroquinolin-3-yl)-6H-thieno[2,3-b]pyrrole-5-carboxamide (Example 17; 200 mg, 0.38 mmol) in EtOH (6 mL) and heated to 70° C. for 3 hrs. 2M HCl (1 mL) was added and the mixture heated to 70° C. for 18 h. After cooling all volatiles were removed under reduced pressure. Chromatography on silica gel (eluent gradient of CH₂Cl₂ to THF) and washing the resultant solid with Et₂O then hexane afforded the title compound (170 mg, 92%) as an off white solid.

¹H NMR (400 MHz) 3.05 (dd, 1H), 3.21 (m, 2H), 3.42 (m, 2H), 3.77 (dd, 1H), 4.03 (m, 1H), 4.14 (m, 1H), 4.51 (dd, 1H), 4.77 (m, 2H), 4.92 (d, 1H), 5.02 (d, 1H), 6.93 (d, 1H), 7.05 (t, 1H), 7.11 (s, 1H), 7.19 (s, 1H), 7.28 (m, 2H), 8.55 (d, 1H), 11.94 (s, 1H); MS m/z MH⁺ 489, 491.

Example 19

There is no Example number 19.

Example 20

2-Chloro-N-{1-[2-(dimethylamino)ethyl]-2-oxo-1,2,3,4-tetrahydroquinolin-3-yl}-6H-thieno[2,3-b]pyrrole-5-carboxamide

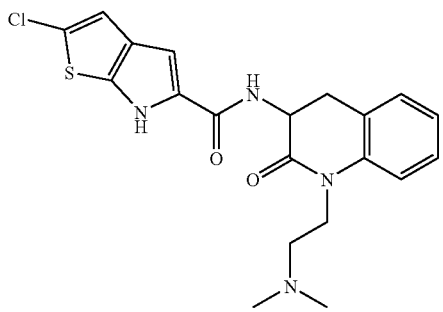

1-Hydroxybenzotriazole (0.69 g, 0.51 mmol) was added to a solution of 3-amino-1-[2-(dimethylamino)ethyl]-3,4-dihydroquinolin-2(1H)-one (Method 10, 100 mg, 0.427 mmol) in DMF (3 mL) followed by 2-chloro-6H-thieno[2,3-b]pyrrole-5-carboxylic acid (Method 9, 86 mg, 0.42 mmol) and EDCI (0.98 g, 0.51 mmol). The reaction was diluted with EtOAc (40 mL) and sat. aqueous NaHCO₃ (20 mL) and the separated organic layer was dried (MgSO₄), filtered and evaporated to dryness. Purification by column chromatography (MeOH:DCM 1:9) afforded the title compound (70 mg, 56%) as a yellow solid.

¹H NMR 2.70 (s, 6H), 3.20 (m, 4H), 4.22 (m, 2H), 4.73 (m, 1H), 7.20 (m, 6H), 8.57 (d, 1H), 12.94 (s, 1H); MS m/z 417, 419

Example 21

2-Chloro-N-{1-[(2,2-dimethyl-1,3-dioxan-5-yl)methyl]-2-oxo-1,2,3,4-tetrahydroquinolin-3-yl}-6H-thieno [2,3-b]pyrrole-5-carboxamide

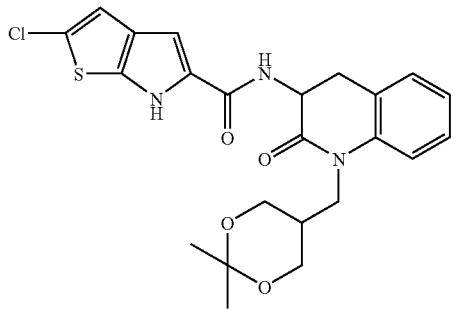

The procedure of Method 3 was followed, using 3-amino-1-[(2,2-dimethyl-1,3-dioxan-5-yl)methyl]-3,4-dihydroquinolin-2(1H)-one (Method 11) and 2-chloro-6H-thieno[2,3-b]pyrrole-5-carboxylic acid (Method 9), to give the title compound (83%) as a white solid.

¹H NMR (CDCl₃) 1.43 (s, 3H), 1.47 (s, 3H), 2.18 (m, 1H), 2.88 (m, 1H), 3.69 (m, 3H), 3.98 (m, 3H), 4.32 (dd, 1H), 4.70 (m, 1H), 6.85 (m, 2H), 7.10 (m, 1H), 7.28 (m, 4H), 10.50 (br, 1H); MS m/z 496, 498.

Example 22

2-Chloro-N-{1-[3-hydroxy-2-(hydroxymethyl)propyl]-2-oxo-1,2,3,4-tetrahydroquinolin-3-yl}-6H-thieno[2,3-b]pyrrole-5-carboxamide

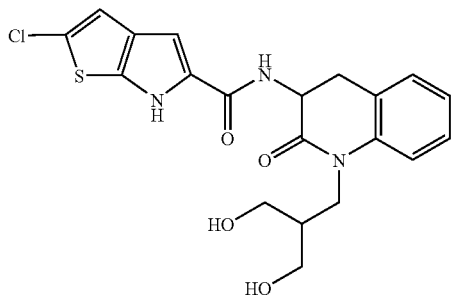

Acid catalysed hydrolysis of the acetonide group of Example 21 following the procedure described for Example 9 gave the title compound (90%) as a white solid.

¹H NMR 1.90 (m, 1H), 3.06 (m, 4H), 3.38 (m, 1H), 3.46 (m, 1H), 3.83 (dd, 1 H), 4.04 (m, 1H), 4.38 (t, 1H), 4.48 (t, 1H), 4.68 (m, 1H), 7.07 (m, 2H), 7.17 (s, 1H), 7.28 (m, 3H), 8.48 (d, 1H), 11.92 (s, 1H); MS m/z 516, 518.

Example 23

2,3-Dichloro-N-{1-[(2,2-dimethyl-1,3-dioxan-5-yl)methyl]-2-oxo-1,2,3,4-tetrahydroquinolin-3-yl}-4H-thieno[3,2-b]pyrrole-5-carboxamide

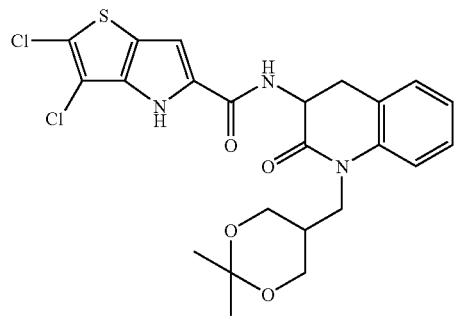

The procedure of Method 3 was followed using 3-amino-1-[(2,2-dimethyl-1,3-dioxan-5-yl)methyl]-3,4-dihydroquinolin-2(1H)-one (Method 11) and 2,3-dichloro-4H-thieno[3,2-b]pyrrole-5-carboxylic acid (Method 8) to give the title compound (85%) as a white solid.

¹H NMR 1.39 (s, 3H), 1.47 (s, 3H), 2.00 (m, 1H), 3.20 (m, 2H), 3.74 (m, 2 H), 3.83 (m, 3H), 4.18 (dd, 1H), 4.72 (quin, 1H), 7.07 (m, 1H), 7.20 (s, 1H), 7.30 (m, 3H), 8.57 (d, 1H), 12.52 (s, 1H); MS m/z (M−H)⁻ 506, 508.

Example 24

2,3-Dichloro-N-{1-[3-hydroxy-2-(hydroxymethyl)propyl]-2-oxo-1,2,3,4-tetrahydroquinolin-3-yl}-4H-thieno[3,2-b]pyrrole-5-carboxamide

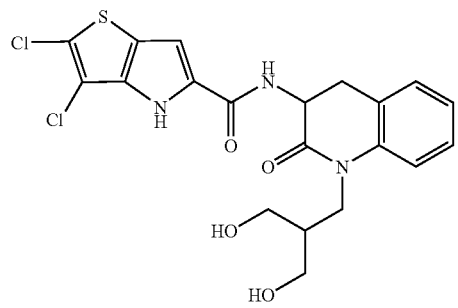

Acid catalysed hydrolysis of the acetonide of Example 23 in exactly the same manner as for the synthesis of Example 9 formed the title compound (91%) as a white solid.

¹H NMR 1.90 (m, 1H), 3.10 (m, 2H), 3.29 (s, 1H), 3.37 (m, 2H), 3.51 (m, 1H), 3.86 (dd, 1H), 4.08 (m, 1H), 4.38 (t, 1H), 4.51 (t, 1H), 4.72 (m, 1H), 7.04 (t, 1H), 7.20 (s, 1H), 7.29 (m, 3H), 8.58 (d, 1H), 12.49 (s, 1H); MS m/z 468

Example 25

2-Chloro-N-(1-{2-[(2,3-dihydroxypropyl)amino]-2-oxoethyl}-2-oxo-1,2,3,4-tetrahydroquinolin-3-yl)-6H-thieno[2,3-b]pyrrole-5-carboxamide

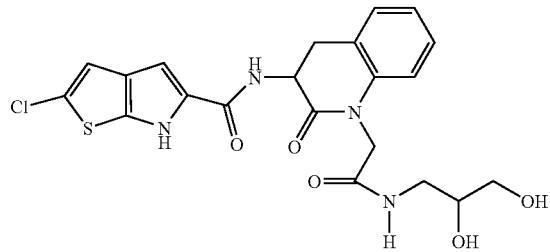

In an similar manner to Example 3, using 2-chloro-6H-thieno[2,3-b]pyrrole-5-carboxylic acid (Method 9) as the carboxylic acid and 3-aminopropane-1,2-diol as the amine the title compound (47%) was prepared as a solid.

$^1$H NMR: 3.03 (m, 2H), 3.16 (d, 1H), 3.24 (t, 1H), 3.29 (m, 2H), 3.52 (m, 1 H), 4.37 (dd, 1H), 4.47 (t, 1H), 4.74 (m, 2H), 4.82 (m, 1H), 6.93 (d, 1H), 7.07 (t, 1H), 7.12 (s, 1H), 7.20 (s, 1H), 7.28 (m, 2H), 8.07 (m, 1H), 8.56 (d, 1H), 11.93 (s, 1H); m/z 477, 479

Example 26

2-Chloro-N-{1-[2-(methoxy)ethyl]-2-oxo-1,2,3,4-tetrahydroquinolin-3-yl}-6H-thieno[2,3-b]pyrrole-5-carboxamide

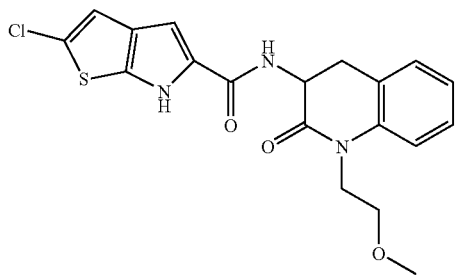

EDCI (225 mg, 1.17 mmol) was added to a suspension of 5-carboxy-2-chloro-6H-thieno[2,3-b]pyrrole (Method 9, 234 mg, 1.06 mmol) and 3-amino-1-(2-methoxyethyl)-3,4-dihydroquinolin-2(1H)-one (Method 12; 215 mg, 1.06 mmol) in DCM (20 mL) and the reaction stirred for 18 hours. The reaction was evaporated and the residue was partitioned between DCM:MeOH (9:1) (100 mL) and water (25 mL). The organic layer was then separated, dried (MgSO$_4$), filtered and evaporated. The residue was purified by column chromatography (DCM to DCM:MeOH (9:1)) to afford the title compound (180 mg, 42%) as a yellow solid.

$^1$H NMR (CDCl$_3$) 2.89 (app. t, 1H), 3.36 (s, 3H), 3.66 (m, 3H), 4.10 (dt, 1H), 4.28 (dt, 1H), 6.83 (d, 1H), 7.11 (dd, 1H), 7.28 (m, 5H), 10.78 (br. s, 1H); MS m/z (M+Na)$^+$ 426, 428.

Example 27

2-Chloro-N-[1-(cyanomethyl)-2-oxo-1,2,3,4-tetrahydroquinolin-3-yl]-6H-thieno[2,3-b]pyrrole-5-carboxamide

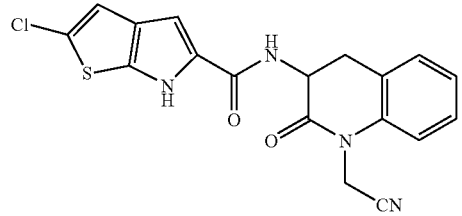

EDCI (1.09 g, 5.65 mmol) was added to a suspension of 5-Carboxy-2-chloro-6H-thieno[2,3-b]pyrrole (Method 9, 1.04 g, 5.13 mmol) and (3-amino-2-oxo-3,4-dihydroquinolin-1(2H)-yl)acetonitrile (Method 13; 1.29 g, 5.13 mmol) in DCM (30 mL) and the reaction stirred for 18 hours. The reaction was evaporated and the residue was partitioned between DCM:MeOH (9:1) (100 mL) and aqueous K$_2$CO$_3$ (25 mL). The organic layer was then separated, dried (MgSO$_4$), filtered and evaporated. The residue was purified by column chromatography (DCM to DCM:MeOH (9:1)) to give a brown solid. The solid was triturated with refluxing Et$_2$O (25 mL) and the solid filtered, washed with Et$_2$O (25 mL) then hexane (25 mL) to afford the title compound (414 mg, 21%) as a pale brown solid.

$^1$H NMR 3.08 (dd, 1H), 3.23 (app. t, 1H), 4.81 (m, 1H), 5.12 (s, 2H), 7.10 (s, 1H), 7.15 (t, 1H), 7.21 (s, 1H), 7.28 (d, 1H), 7.39 (m, 2H), 8.66 (d, 1H), 11.99 (br. s, 1H); MS m/z (M–H)$^-$ 383, 385

Example 28

2-Chloro-N-{1-[(3-methyl-1,2,4-oxadiazol-5-yl)methyl]-2-oxo-1,2,3,4-tetrahydroquinolin-3-yl}-6H-thieno[2,3-b]pyrrole-5-carboxamide

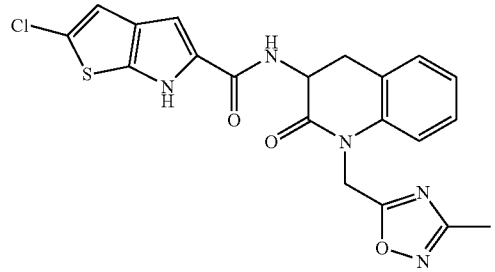

N-Methylmorpholine (118 μL, 1.07 mmol) then ethyl chloroformate (103 μL, 1.07 mmol) were added to N-[1-(carboxymethyl)-2-oxo-1,2,3,4-tetrahydroquinolin-3-yl]-2-chloro-6H-thieno[2,3-b]pyrrole-5-carboxamide (Example 2; 431 mg, 1.07 mmol) in anhydrous THF (10 mL) at 0° C. After 20 minutes N'-hydroxyethanimidamide (119 mg, 1.61 mmol) was added and the reaction stirred at ambient temperature for 3 days then at reflux for 5 hours. After evaporation to dryness the residue was suspended in 1,4-dioxane and refluxed for 18 hours. On cooling the mixture was diluted with EtOAc (100 mL) and washed with H$_2$O (25 mL). The aqueous was extracted with DCM (3×50 mL) and the combined organics dried (MgSO$_4$), filtered and evaporated. The residue was purified by column chromatography

Example 29

2-Chloro-N-[2-oxo-1-(1H-tetrazol-5-ylmethyl)-1,2,3,4-tetrahydroquinolin-3-yl]-6H-thieno [2,3-b]pyrrole-5-carboxamide

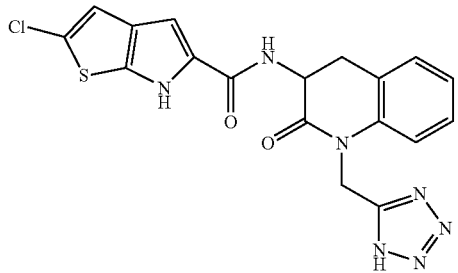

Sodium azide (178 mg, 2.73 mmol) and triethylamine hydrochloride (356 mg, 2.59 mmol) were added to 2-chloro-N-[1-(cyanomethyl)-2-oxo-1,2,3,4-tetrahydroquinolin-3-yl]-6H-thieno[2,3-b]pyrrole-5-carboxamide (Example 27; 300 mg, 0.78 mmol) in 1-methyl-2-pyrrolidinone (7 mL) and then heated at 150° C. for 3 hours. On cooling the mixture was diluted with EtOAc (100 mL) and washed with H$_2$O (50 mL). The aqueous layer was acidified with citric acid and extracted with MeOH:DCM (1:19) and the combined organics dried (MgSO$_4$), filtered and evaporated. The residue was purified by applying the material to a 10 g Isolute NH$_2$ column in MeOH:DCM (1:9) (10 mL) and eluting with MeOH:DCM (1:9) (6×10 mL). The column was eluted with MeOH: 2M HCl in Et$_2$O:DCM (5:4:45) (6×10 mL) and the relevant fractions evaporated to afford the title product (246 mg, 74%) as pale pink powder.

$^1$H NMR 3.09 (dd, 1H), 3.26 (app. t, 1H), 4.90 (m, 1H), 5.31 (d, 1H), 5.59 (d, 1H), 7.09 (m, 3H), 7.19 (s, 1H), 7.31 (m, 2H), 8.59 (d, 1H), 11.95 (br. s, 1H); MS m/z 450, 452

Example 30

2-Chloro-N-(1-{2-[(methylsulphonyl)amino]-2-oxoethyl}-2-oxo-1,2,3,4-tetrahydroquinolin-3-yl)-6H-thieno [2,3-b]pyrrole-5-carboxamide

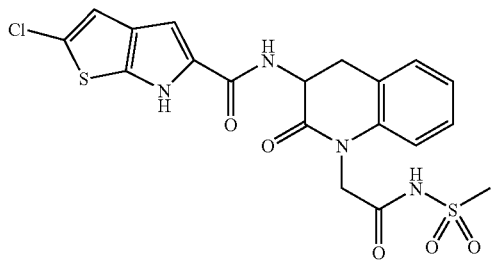

Methanesulphonamide (90 mg, 0.94 mmol), 4-(dimethylamino)pyridine (287 mg, 2.35 mmol) and EDCI (225 mg, 1.17 mmol) were added to a suspension of N-[1-(carboxymethyl)-2-oxo-1,2,3,4-tetrahydroquinolin-3-yl]-2-chloro-6H-thieno[2,3-b]pyrrole-5-carboxamide (Example 2; 315 mg, 0.78 mmol) in DCM (50 mL) and stirred for 2 days. The reaction was diluted with MeOH:DCM (1:19) (50 mL) and washed with 1M HCl(aq). (50 mL), the organic layer was separated, dried (MgSO$_4$), filtered and evaporated. The residue was purified by applying the material to a 10 g Isolute NH$_2$ column in MeOH:DCM (1:9) (10 mL) and eluted with MeOH:DCM (1:9) (6×10 mL) then MeOH: 2M HCl in Et$_2$O:DCM (5:4:45) (6×10 mL) and the relevant fractions evaporated to give a pink gum which was triturated with refluxing Et$_2$O (25 mL) and after cooling the title product (206 mg, 55%) was collected by filtration as pale pink powder.

$^1$H NMR 3.06 (dd, 1H), 3.22 (m, 1H), 4.45–4.87 (m, 6H), 7.00 (d, 1H), 7.09 (m, 2H), 7.19 (s, 1H), 7.30 (m, 2H), 8.59 (d, 1H), 11.95 (br. s, 1H), 12.17 (br. s, 1H); MS m/z (M+Na)$^+$ 503, 505.

Example 31

N-{1-[(2Z)-2-Amino-2-(hydroxyimino)ethyl]-2-oxo-1,2,3,4-tetrahydroquinolin-3-yl}-2-chloro-6H-thieno [2,3-b]pyrrole-5-carboxamide

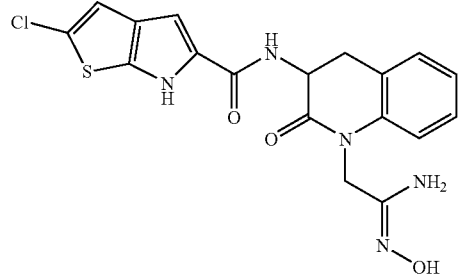

Hydroxylamine hydrochloride (181 mg, 2.60 mmol) in MeOH (5 mL) was added to a solution of NaOMe in MeOH (10.20 mL, 0.25M) under an inert atmosphere followed by 2-chloro-N-[1-(cyanomethyl)-2-oxo-1,2,3,4-tetrahydroquinolin-3-yl]-6H-thieno[2,3-b]pyrrole-5-carboxamide (Example 27; 500 mg, 1.30 mmol) in THF (7 mL) then stirred for 18 hours. The mixture was diluted with EtOAc (100 mL) and washed with brine (25 mL), dried (Na$_2$SO$_4$), filtered and evaporated to afford the title product (550 mg, 100%) as a pale brown solid.

$^1$H NMR 3.04 (dd, 1H), 3.19 (app. t, 1H), 4.30 (d, 1H), 4.76 (m, 1H), 5.39 (br. s, 2H), 7.02 (d, 1H), 7.08 (s, 1H), 7.17 (s, 1H), 7.18 (d, 1H), 7.25–7.33 (m, 2H), 8.56 (d, 1H), 9.17 (br. s, 1H), 11.95 (br. s, 1H), 12.05 (br. s, 1H); MS m/z 418, 420.

Example 32

2-Chloro-N-{2-oxo-1-[(5-oxo-4,5-dihydro-1,2,4-oxadiazol-3-yl)methyl]-1,2,3,4-tetrahydroquinolin-3-yl}-6H-thieno[2,3-b]pyrrole-5-carboxamide

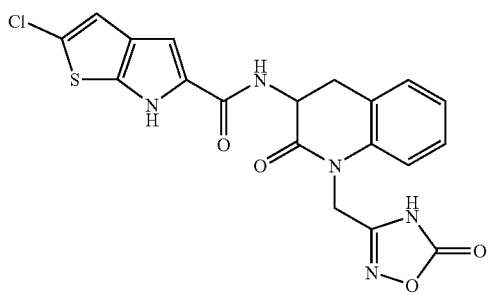

N-[1-((2Z)-2-Amino-2-{[(ethoxycarbonyl)oxy]imino}ethyl)-2-oxo-1,2,3,4-tetrahydroquinolin-3-yl]-2-chloro-6H-thieno[2,3-b]pyrrole-5-carboxamide (Method 14) was dissolved in 1,4-Dioxane and the solvent distilled off with the oil bath temperature 140° C. This was repeated 4 times. The residual solid was triturated with refluxing Et$_2$O (10 mL) and after cooling filtered, washed with Et$_2$O (10 mL) and hexane (10 mL) to give the title product (184 mg, 87% (2 steps)) as a pale brown solid.

$^1$H NMR 3.04 (dd, 1H), 3.22 (app. t, 1H), 4.82 (m, 1H), 4.93 (d, 1H), 5.18 (d, 1H), 7.06–7.20 (m, 4H), 7.26–7.35 (m, 2H), 8.54 (d, 1H), 11.92 (br. s, 1H), 12.54 (br. s, 1H); MS m/z (M–H)$^-$ 442, 444

Example 33

N-{1-[(5-Amino-1,3,4-oxadiazol-2-yl)methyl]-2-oxo-1,2,3,4-tetrahydroquinolin-3-yl}-2-chloro-6H-thieno[2,3-b]pyrrole-5-carboxamide

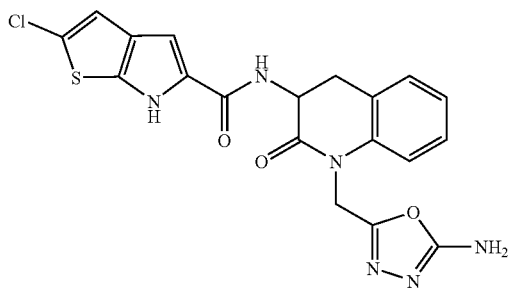

1,4-Dioxane (5 mL), 2-chloro-N-[1-(2-hydrazino-2-oxoethyl)-2-oxo-1,2,3,4-tetrahydroquinolin-3-yl]-6H-thieno[2,3-b]pyrrole-5-carboxamide (Method 15; 300 mg, 0.72 mmol), cyanogen bromide (80 mg, 0.75 mmol) and 1,4-dioxane (2 mL) were added to a solution of Na$_2$CO$_3$ (77 mg, 0.72 mmol) in H$_2$O (1.7 mL) and stirred for 18 hours. The mixture was diluted with EtOAc (50 mL) and THF (20 mL) and washed with H$_2$O (25 mL). The organic was dried (Na$_2$SO$_4$), filtered and evaporated. The residue was purified by reverse phase column chromatography to give a brown solid. This was triturated with refluxing Et$_2$O (25 mL), filtered, washed with Et$_2$O (25 mL) then hexane (25 mL) to afford the title compound (63 mg, 20%) as a brown powder.

$^1$H NMR 2.94 (app. t, 1H), 3.31 (dd, 1H), 4.81 (m, 1H), 5.03 (d, 1H), 5.39 (d, 1H), 6.99 (m, 3H), 7.25 (m, 2H), 7.34 (d, 1H), 7.66 (d, 1H), 11.37 (br. s, 1H); MS m/z (M–H)$^-$ 441, 443.

Example 34

2-Chloro-N-{1-[2-(methylthio)ethyl]-2-oxo-1,2,3,4-tetrahydroquinolin-3-yl}-6H-thieno[2,3-b]pyrrole-5-carboxamide

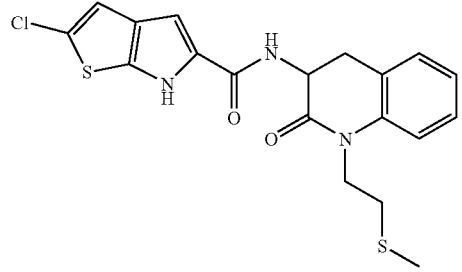

EDCI (915 mg, 4.77 mmol) was added to a suspension of 5-Carboxy-2-chloro-6H-thieno[2,3-b]pyrrole (801 mg, 3.97 mmol), 3-amino-1-[2-(methylthio)ethyl]-3,4-dihydroquinolin-2(1H)-one (Method 16; 1.40 g, 3.97 mmol) and 1-hydroxybenzotriazole (537 mg, 3.97 mmol) in DCM (60 mL) and the reaction stirred for 18 hours. The reaction was evaporated and the residue was partitioned between DCM (100 mL) and water (25 mL). The organic layer was then separated, dried (MgSO$_4$), filtered and evaporated. The residue was purified by column chromatography (DCM to DCM:EtOAc (9:1)) to afford the title compound (660 mg, 40%) as a white solid.

$^1$H NMR 2.13 (s, 3H), 2.69 (t, 2H), 3.02 (dd, 1H), 3.13 (app. t, 1H), 4.13 (t, 2H), 4.70 (m, 1H), 7.06 (d, 1H), 7.11 (s, 1H), 7.19 (s, 1H), 7.22 (d, 1H), 7.27–7.36 (m, 2H), 8.51 (d, 1H), 11.92 (br. s, 1H); MS m/z (M–H)$^-$ 418, 420

Example 35

2-Chloro-N-{1-[2-(methylsulfinyl)ethyl]-2-oxo-1,2,3,4-tetrahydroquinolin-3-yl}-6H—thieno[2,3-b]pyrrole-5-carboxamide and

Example 36

2-Chloro-N-{1-[2-(methylsulfonyl)ethyl]-2-oxo-1,2,3,4-tetrahydroquinolin-3-yl}-6H-thieno[2,3-b]pyrrole-5-carboxamide

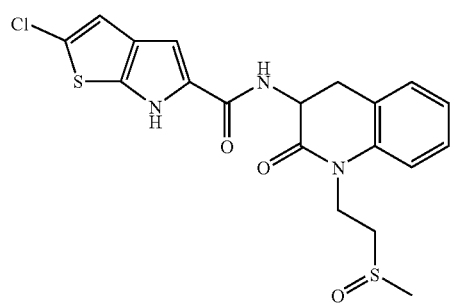

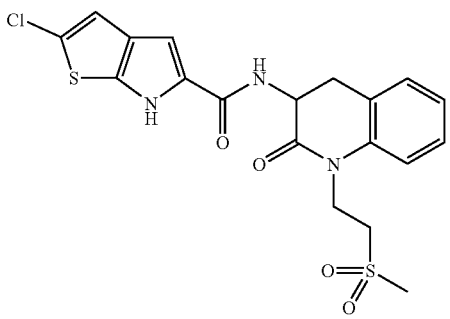

Oxone (701 mg, 1.14 mmol) in H₂O (12 mL) was added to 2-chloro-N-{1-[2-(methylthio)ethyl]-2-oxo-1,2,3,4-tetrahydroquinolin-3-yl}-6H-thieno[2,3-b]pyrrole-5-carboxamide (Example 34; 462 mg, 1.10 mmol) in MeOH (12 mL) and stirred for 18 hours. The mixture was diluted with EtOAc (100 mL) washed with saturated NaHCO₃ (20 mL), dried (Na₂SO₄), filtered and evaporated. The residue was purified by column chromatography (DCM to DCM:THF (3:2) then DCM:MeOH (4:1)) to give 2 yellow solids. Each solid was triturated separately with refluxing Et₂O (25 mL) and filtered, washed with Et₂O (25 mL) then hexane (25 mL) to afford the title compounds (Example 35, 104 mg, 22% and Example 36, 230 mg, 46%) as solids.

Example 35

¹H NMR 2.62 (s, 3H), 3.05 (m, 4H), 4.28 (m, 2H), 4.67–4.77 (m, 1H), 7.09 (m, 2H), 7.19 (s, 1H), 7.31 (m, 3H), 8.52 (dd, 1H), 11.93 (br. s, 1H); MS m/z (M–H)⁻ 434, 436

Example 36

¹H NMR 3.03 (dd, 1H), 3.09 (s, 3H), 3.16 (app. t, 1H), 3.38–3.52 (m, 2H), 4.34 (t, 2H), 4.67–4.77 (m, 1H), 7.06–7.13 (m, 2H), 7.19 (s, 1H), 7.22 (d, 1H), 7.24–7.37 (m, 3H), 8.52 (dd, 1H), 11.94 (br. s, 1H); MS m/z (M–H)⁻ 450, 452

Example 37

2,3-Dichloro-N-[1-(methoxycarbonylmethyl)-2-oxo-1,2,3,4-tetrahydroquinolin-3-yl]-4H-thieno[3,2-b]pyrrole-5-carboxamide

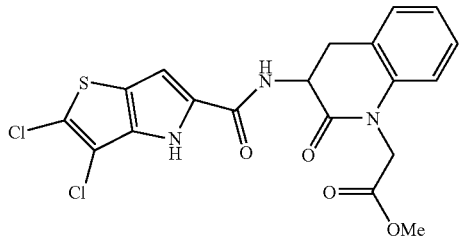

5-Carboxy-2,3-dichloro-4H-thieno[3,2-b]pyrrole (Method 8; 595 mg, 2.52 mmol), HOBt (340 mg, 2.52 mmol), DCM (100 mL) and finally EDCI (483 mg, 2.52 mmol) were added to methyl (3-amino-2-oxo-3,4-dihydroquinolin-1(2H)-yl)acetate (Method 1, 590 mg, 2.52 mmol) and the reaction was stirred for 18 hours The reaction was then diluted with water (50 mL) and stirred vigorously for 30 min. The resultant precipitate was filtered and washed with Et₂O (2×20 mL). After filtration the resultant solid was then triturated with refluxing Et₂O (25 mL) and after cooling the title compound (528 mg, 46%) was collected again by filtration as a white solid.

¹H NMR 3.10 (dd, 1H), 3.21 (app. t, 1H), 3.69 (s, 3H), 4.67 (d, 1H), 4.81 (m, 2H), 7.07 (m, 2H), 7.23 (s, 1H), 7.31 (m, 2H), 8.69 (d, 1H), 12.51 (s, 1H); MS m/z 452, 454.

Example 38

N-[1-(Carboxymethyl)-2-oxo-1,2,3,4-tetrahydroquinolin-3-yl]-2,3-dichloro-4H-thieno[3,2-b]pyrrole-5-carboxamide

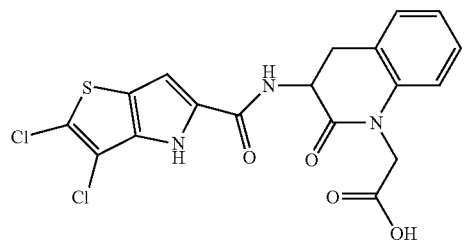

The title compound was prepared by the method described for Example 2 using 2,3-Dichloro-N-[1-(methoxycarbonylmethyl)-2-oxo-1,2,3,4-tetrahydroquinolin-3-yl]-4H-thieno[3,2-b]pyrrole-5-carboxamide (Example 37) as starting material.

¹H NMR 3.15 (m, 2H), 4.54 (d, 1H), 4.78 (m, 2H), 7.06 (m, 2H), 7.21 (m, 1H), 7.28 (m, 2H), 8.67 (d, 1H), 12.52 (s, 1H), 12.94 (br, 1H); MS m/z 438, 440

Example 39

2,3-Dichloro-N-[1-(2-hydroxyethyl)-2-oxo-1,2,3,4-tetrahydroquinolin-3-yl]-4H-thieno[3,2-b]pyrrole-5-carboxamide

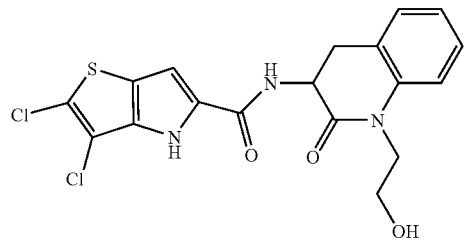

The title compound was prepared by the method described for Example 8 using N-[1-(Carboxymethyl)-2-oxo-1,2,3,4-tetrahydroquinolin-3-yl]-2,3-dichloro-4H-thieno[3,2-b]pyrrole-5-carboxamide (Example 38) as starting material.

¹H NMR 3.10 (m, 2H), 3.61 (m, 2H), 3.98 (m, 2H), 4.79 (m, 2H), 7.05 (m, 1H), 7.28 (m, 3H), 8.57 (d, 1H), 12.49 (s, 1H); MS m/z 424.

Example 40

2,3-Dichloro-N-{1-[(2R)-2,3-dihydroxypropyl]-2-oxo-1,2,3,4-tetrahydroquinolin-3-yl}-4H-thieno[3,2-b]pyrrole-5-carboxamide

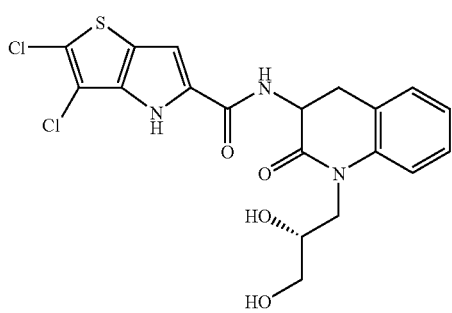

Acid catalysed hydrolysis of 2,3-dichloro-N-{1-[(2R)-2,3-dihydroxypropyl]-2-oxo-1,2,3,4-tetrahydroquinolin-3-yl}-4H-thieno[3,2-b]pyrrole-5-carboxamide (Method 7) following the procedure described for Example 9 gave the title compound (92%) as a white solid.

$^1$H NMR 3.06 (m, 2H), 3.33 (m, 2H), 3.85 (m, 3H), 4.70 (m, 3H), 7.04 (m, 1H), 7.24 (m, 4H), 8.58 (2×d, 1H), 12.49 (s, 1H); MS m/z 454, 456

Example 41

2-Chloro-N-{1-[3-(dimethylamino)-2-hydroxypropyl]-2-oxo-1,2,3,4-tetrahydroquinolin-3-yl}-6H-thieno[2,3-b]pyrrole-5-carboxamide

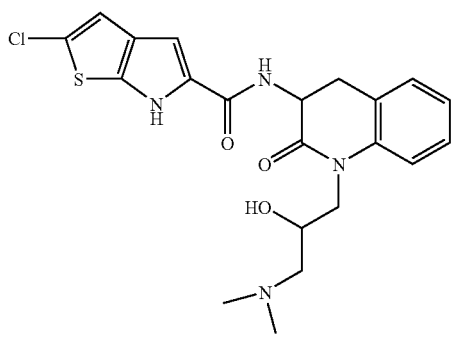

The title compound was prepared by a two-step coupling-epoxide opening sequence. Standard amide bond formation analogous to Method 3 except using 3-amino-1-(oxiran-2-ylmethyl)-3,4-dihydroquinolin-2(1H)-one (Method 19) as amine and 2-chloro-6H-thieno[2,3-b]pyrrole-5-carboxylic acid (Method 9) as the acid component formed the title compound as a white solid which was used without further purification. The crude amide product (150 mg) was dissolved in EtOH (5 mL) followed by addition of dimethylamine in EtOH (5.0–6.0 M in EtOH, 0.5 mL) and the reaction was stirred overnight under argon. The reaction was diluted with EtOAc (40 mL) and sat. aqueous NaHCO$_3$ (20 mL) and the separated organic layer was dried (MgSO$_4$), filtered and evaporated to dryness. Purification by column chromatography (MeOH:DCM 2:9) afforded the title compound (41 mg) as a yellow solid.

$^1$H NMR 1.85 (s, 3H), 2.16 (s, 3H), 2.27 (m, 2H), 3.05 (m, 2H), 3.20 (br, 1 H), 3.63 (m, 1H), 3.84 (m, 1H), 4.08 (m, 1H), 4.68 (m, 1H), 7.15 (m, 6H), 8.48 (d, 1H), 12.00 (s, 1H); MS m/z 447

Example 42

2-Chloro-N-{2-oxo-1-[(2-oxo-1,3-dioxan-5-yl)methyl]-1,2,3,4-tetrahydroquinolin-3-yl}-6H-thieno[2,3-b]pyrrole-5-carboxamide

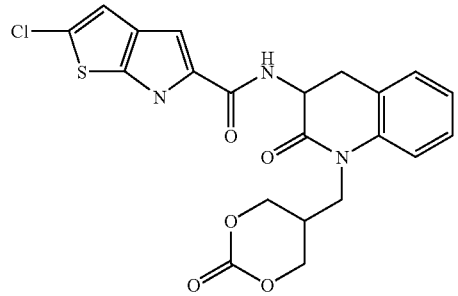

Carbonyl diimidazole (143 mg, 0.88 mmol) was added to 2-chloro-N-{1-[3-hydroxy-2-(hydroxymethyl)propyl]-2-oxo-1,2,3,4-tetrahydroquinolin-3-yl}-6H-thieno[2,3-b]pyrrole-5-carboxamide (Example 22; 250 mg, 0.58 mmol) followed by DMAP (2 mg) and the reaction was heated at 50° C. for 4 hours. The reaction was quenched by addition of EtOAc (50 mL) and H$_2$O (10 mL) and the organic layer was separated and washed further with saturated aqueous NaHCO$_3$, 1M HCl (aq.) and brine. The organic layer was then dried (MgSO$_4$), filtered and evaporated. Trituration with hot Et$_2$O (15 mL), cooling and filtration afforded the title compound (182 mg, 0.40 mmol, 68%) as a white solid.

$^1$H NMR 3.07 (dd, 1H), 3.21 (t, 1H), 4.22 (m, 5H), 4.45 (m, 2H), 4.73 (m, 1 H), 7.07 (m, 2H), 7.18 (s, 1H), 7.21 (m, 3H), 8.50 (d, 1H), 11.95 (s, 1H); MS m/z 460, 462.

Example 43

2-Chloro-N-[1-(3-hydroxypropyl)-2-oxo-1,2,3,4-tetrahydroquinolin-3-yl]-6H-thieno[2,3-b]pyrrole-5-carboxamide

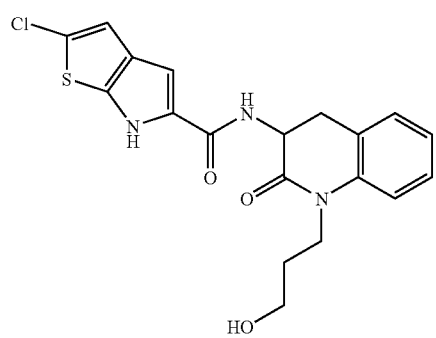

TBAF (1.0 M in THF, 4.92 mL, 4.92 mmol) was added to N-[1-(3-{[tert-butyl(dimethyl)silyl]oxy}propyl)-2-oxo-1,2,3,4-tetrahydroquinolin-3-yl]-2-chloro-6H-thieno[2,3-b]pyrrole-5-carboxamide (Method 20, 1.84 g, 3.56 mmol) in THF (15 mL) and the reaction was stirred for 48 hours. The reaction was quenched by the addition of EtOAc (50 mL) and NH₄Cl (aq.) (20 mL) and the organic layer was dried (MgSO₄), filtered and evaporated. Purification by column chromatography afforded the title compound (1.24 g, 3.08 mmol, 86%) as a white solid.

¹H NMR 1.79 (m, 2H), 3.13 (m, 2H), 3.52 (m, 2H), 4.01 (m, 2H), 4.58 (m, 2H), 4.73 (quin, 1H), 7.20 (m, 6H), 8.53 (d, 1H), 11.96 (s, 1H); MS m/z 404

Example 44

2-Chloro-N-{1-[3-(methylamino)-3-oxopropyl]-2-oxo-1,2,3,4-tetrahydroquinolin-3-yl}-6H-thieno[2,3-b]pyrrole-5-carboxamide

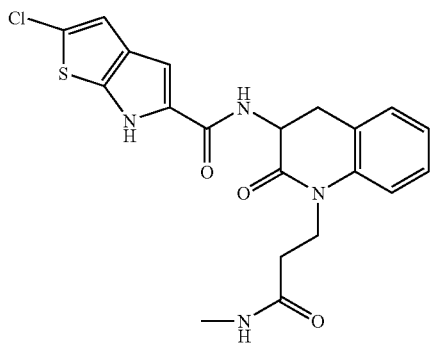

Pyridinium dichromate (329 mg, 0.88 mmol) was added to 2-chloro-N-[1-(3-hydroxypropyl)-2-oxo-1,2,3,4-tetrahydroquinolin-3-yl]-6H-thieno[2,3-b]pyrrole-5-carboxamide (Example 43; 100 mg, 0.248 mmol) in DMF (3 mL) and the reaction was stirred for 24 hours. The reaction was diluted with EtOAC (20 mL) and filtered through celite. The filtrate was washed with 1M HCl (aq.) and the organic layer was dried (MgSO₄), filtered and evaporated to afford the crude acid which was used without purification. Standard amide bond formation analogous to Method 3 except using methylamine (2.0 M in THF) as amine gave the title compound (65 mg, 61% over 2 steps) as a white solid.

¹H NMR 2.43 (m, 2H), 2.60 (s, 3H), 3.08 (m, 2H), 4.12 (m, 2H), 4.70 (m, 1 H), 7.07 (m, 2H), 7.23 (m, 2H), 7.32 (m, 2H), 7.89 (s, 1H), 8.50 (d, 1H), 11,92 (s, 1 H); MS m/z 431

Example 45

2-Chloro-N-[2-oxo-1-(2-oxobutyl)-1,2,3,4-tetrahydroquinolin-3-yl]-6H-thieno[2,3-b]pyrrole-5-carboxamide

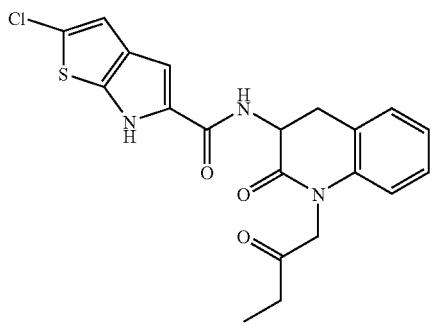

Standard amide bond formation analogous to Method 3 using 3-amino-1-(2-oxobutyl)-3,4-dihydroquinolin-2(1H)-one (Method 22) as amine and 2-chloro-6H-thieno[2,3-b]pyrrole-5-carboxylic acid (Method 9) as the acid component formed the title compound (56%) as a white solid.

¹H NMR 0.95 (t, 3H), 2.58 (m, 2H), 3.04 (dd, 1H), 3.19 (t, 1H), 4.73 (m, 2 H), 4.94 (d, 1H), 6.88 (d, 1H), 7.05 (m, 2H), 7.24 (m, 3H), 8.52 (d, 1H), 11.90 (s, 1H); MS m/z 416, 418

Example 46

2-Chloro-N-[1-(2-hydroxybutyl)-2-oxo-1,2,3,4-tetrahydroquinolin-3-yl]-6H-thieno[2,3-b]pyrrole-5-carboxamide

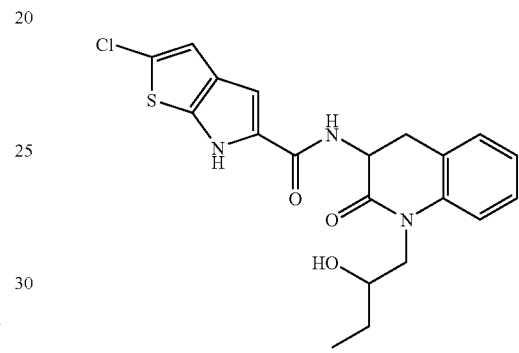

Sodium borohydride (13.7 mg, 0.36 mmol) was added to a solution of 2-chloro-N-[1-(2-hydroxybutyl)-2-oxo-1,2,3,4-tetrahydroquinolin-3-yl]-6H-thieno[2,3-b]pyrrole-5-carboxamide (Example 45, 100 mg, 0.24 mmol) in MeOH (10 mL) and the reaction was stirred for 1 hour. The reaction was quenched by addition of H₂O (5 mL) and EtOAc (20 mL) and the organic layer was dried (MgSO₄), filtered and evaporated. The crude solid was triturated with Et₂O (5 mL) and the product (75 mg, 75%) was collected by filtration and isolated as a 2:1 mixture of diastereomers.

¹H NMR 0.90 (m, 3H), 1.38 (m, 2H), 3.07 (m, 2H), 3.71 (m, 2H), 4.03 (m, 1 H), 4.75 (m, 2H), 7.04 (t, 1H), 7.13 (s, 1H), 7.19 (s, 1H), 7.34 (m, 3H), 8.48 (d, 1H), 11.95 (s, 1H); MS m/z 418

Example 47

2,3-Dichloro-N-[(6S)-7-oxo-5,6,7,8-tetrahydroimidazo[1,2-α]pyrimidin-6-yl]-4H-thieno[3,2-b]pyrrole-5-carboxamide

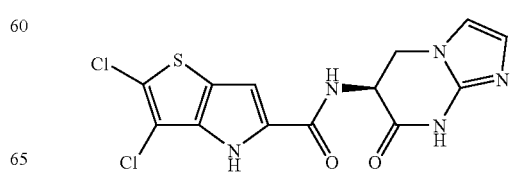

TFA (2 mL) was added to a solution of (6S)-6-(tritylamino)-5,6-dihydroimidazo[1,2-α]pyrimidin-7(8H)-one (Method 23, 400 mg, 1 mmol) in DCM (20 mL) and the reaction was stirred at ambient temperature for 1 hours The volatiles were removed by evaporation under reduced pressure to afford (6S)-6-amino-5,6-dihydroimidazo[1,2-α]pyrimidin-7(8H)-one which was used crude in the next stage.

HOBT (135 mg, 1 mmol) was added to a solution of 2,3-dichloro-4H-thieno[3,2-b]pyrrol-5-yl-2-carboxylic acid (Method 8; 236 mg, 1 mmol) and DIPEA (0.52 mL, 3 mmol) and the reaction stirred at ambient temperature for 5 mins. EDCI (210 mg, 1.1 mmol) was then added and the reaction stirred at ambient temperature for a further 16 hours The reaction mixture was filtered to afford a yellow solid, which was washed with methanol to afford the title compound as a pale yellow solid (202 mg, 55%).

$^1$H NMR 3.97 (t, 1H), 4.35 (dd, 1H), 4.92 (m, 1H), 6.66 (s, 1H), 6.88 (s, 1 H), 7.17 (s, 1H), 8.64 (d, 1H), 11.21 (br s, 1H), 12.51 (br s, 1H); MS m/z 370.

Example 48

2,3-Dichloro-N-(2-oxo-1,2,3,4-tetrahydro-1,5-naphthyridin-3-yl)-4H-thieno[3,2-b]pyrrole-5-carboxamide

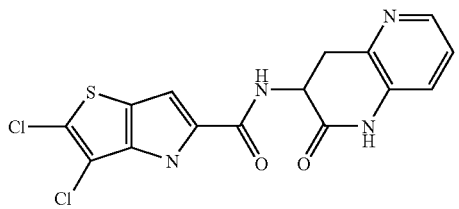

Triethylamine (404 mg, 4 mmol), HOBT (148.5 mg, 1.1 mmol), 2,3-dichloro-4H-thieno[3,2-b]pyrrole-5-carboxylic acid (Method 8, 234 mg, 1.0 mmol) and 3-amino-3,4-dihydro-1,5-naphthyridin-2(1H)-one dihydrochloride (Method 25, 234 mg, 1.0 mmol) were dissolved in dimethylformamide (20 mL.). EDCI (210 mg, 1.1 mmol.) was then added and the reaction mixture stirred at ambient temperature for 2 hours. The reaction mixture was concentrated to small volume and diluted with water (50 mL). The resulting precipitate was collected by filtration, washed with methanol (2×10 mL) and ether and dried under vacuum at 50° C. to give the title compound. (237 mg, 71%)

$^1$H NMR 3.1–3.4 (m, 2H); 4.85 (m, 1H); 7.2 (m, 3H); 8.1 (d, 1H); 8.6 (d, 1H); 10.44 (s, 1H); 12.48 (s, 1H); MS m/z 379.

Example 49

2-Chloro-N-(2-oxo-1,2,3,4-tetrahydro-1,7-naphthyridin-3-yl)-6H-thieno[2,3-b]pyrrole-5-carboxamide

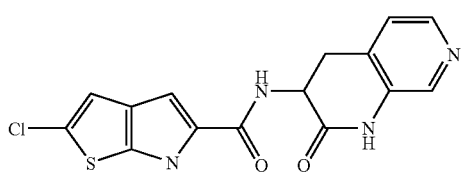

DIPEA (297 mg, 2.3 mmol), HOBT (128 mg, 0.95 mmol), 2-chloro-6H-thieno[2,3-b]pyrrole-5-carboxylic acid (Method 9, 154 mg., 0.767 mmol) and 3-amino-3,4-dihydro-1,7-naphthyridin-2(1H)-one (Method 28, 300 mg, 0.767 mmol) were suspended in DCM (10 mL). EDCI (183 mg, 0.95 mmol) was then added and the reaction mixture stirred at ambient temperature for 2 hrs. The reaction mixture was filtered and the filtrate was diluted with ethyl acetate (100 mL), washed with saturated aqueous sodium bicarbonate (2×25 mL) and brine (25 mL), dried (MgSO$_4$) and evaporated under reduced pressure to give a light brown solid which was washed with methanol (20 mL) and dried to give the title compound (45 mg, 17%).

Example 50

N-(6-Fluoro-1,2,3,4-tetrahydroquinolin-3-yl)-6H-thieno[2,3-b]pyrrole-5-carboxamide

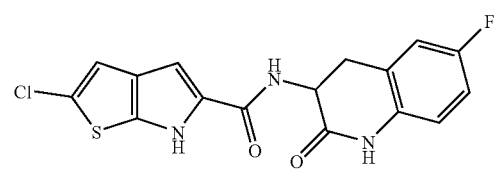

Et$_3$N (184 μL, 1.32 mmol), HOBT (89 mg, 0.66 mmol), 3-amino-6-fluoro-3,4-dihydro-2(1H)-quinolinone monohydrochloride (CAS Reg. No: 82420-54-0) (143 mg, 0.66 mmol), and EDAC (127 mg, 0.66 mmol) were added to a solution of 2-chloro-6H-thieno[2,3-b]pyrrole-5-carboxylic acid (133 mg, 0.66 mmol) in anhydrous DMF (3.5 mL). The reaction was stirred at ambient temperature for approximately 16 h, and then poured into water (50 mL). This was stirred vigorously for about 10 mins. and filtered. The collected precipitate was washed with water and dried in vacuum at 40° C., to give the title compound (203 mg, 84%) as an amorphous solid.

$^1$H NMR 3.12 (m, 2H), 4.71 (m, 1H), 6.89 (m, 1H), 7.02 (m, 1H), 7.07 (m, 1 H), 7.10 (s.1H), 7.13 (dd, 1H), 7.20 (s, 1H), 7.48 (d, 1H), 10.37 (s, 1H), 11.95 (s, 1 H); MS m/z 364, 366.

Example 51

N-(6-Methoxy-1,2,3,4-tetrahydroquinolin-3-yl)-6H-thieno[2,3-b]pyrrole-5-carboxamide

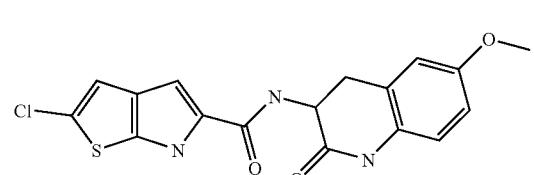

This example was made by the process of Example 50, using 3-amino-3,4-dihydro-6-methoxy-2(1H)-quinolinone monohydrochloride (CAS Reg No: 35287-38-8) and 2-chloro-6H-thieno[2,3-b]pyrrole-5-carboxylic acid (Method 9).

$^1$H NMR 3.03 (dd, 1H), 3.09 (t, 1H), 3.72 (s, 3H), 4.68 (m, 1H), 6.82 (m, 3 H), 7.09 (s, 1H), 7.20 (s, 1H), 8.43 (d, 1H), 10.20 (s, 1H), 11.92 (s, 1H); MS m/z 376,378.

Methods

Method 1

Methyl(3-amino-2-oxo-3,4-dihydroquinolin-1 (2H)-yl)acetate

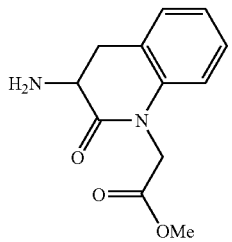

Sodium hydride (60% in oil, 2.52 g, 63.0 mmol) was added to 3-amino-3,4-dihydroquinolin-2(1H)-one hydrochloride (J. Med. Chem., 28, 1985, 1511–16; 5.0 g, 25.2 mmol), in anhydrous DMF (100 mL) at 0° C. over a period of 5 min keeping the internal temperature at <10° C. The reaction was stirred for a further 30 min before addition of methyl bromoacetate (2.85 mL, 30.2 mmol), then stirred for a further 60 min. The reaction was quenched by addition of 1M aqueous HCl (5 mL) and the volatiles were removed by evaporation. The residue was dissolved in DCM (250 mL) and washed with sat. aqueous NaHCO$_3$ (100 mL) and the organic layer was dried (MgSO$_4$), filtered and evaporated to yield the title compound (5.89 g, 25.2 mmol) as yellow paste which was used without further purification.

$^1$H NMR 2.21 (br. s, 2H), 2.78 (d, 1H), 2.97 (dd, 1H), 3.47 (dd, 1H), 3.67 (s, 3H), 4.55 (d, 1H), 4.78 (d, 1H), 6.96 (m, 2H), 7.23 (m, 2H); MS m/z MH$^+$ 235.

Method 2

3-Amino-1-(2,2-dimethyl-1,3-dioxolan-4-ylmethyl)-3,4-dihydroquinolin-2(1H)-one

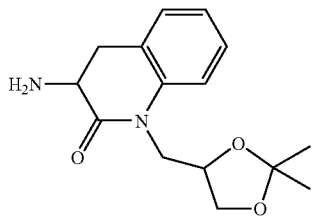

Sodium hydride (60% in oil, 191 mg, 4.70 mmol) was added to 3-amino-3,4-dihydroquinolin-2(1H)-one hydrochloride (J. Med. Chem., 28, 1985; 1511–16,450 mg, 2.27 mmol), in anhydrous DMF (6 mL) at 0° C. over a period of 5 min keeping the internal temperature at <10° C. The reaction was stirred for a further 30 min before addition of (2,2-dimethyl-1,3-dioxolan-4-yl)methyl methanesulfonate (J. Med. Chem. 35, 1992, 1650–62; 528 mg, 2.50 mmol) and the reaction has then heated to 80° C. for a period of 5 h. The reaction was then cooled and evaporated before addition of sat. aqueous NaHCO$_3$ (20 mL) and EtOAc (50 mL). The organic layer was then dried (MgSO$_4$), filtered and evaporated and the residue was purified by column chromatography (MeOH:DCM 1:19) to afford the title compound (330 mg, 53%) as colourless oil.

$^1$H NMR 1.33 (s, 3H), 1.40 (s, 1.5H), 1.45 (s, 1.5H), 1.96 (br. s, 2H), 2.89 (m, 1H), 3.07 (m, 1H), 3.60 (m, 1H), 3.82 (m 1.5H), 4.08 (m, 1.5H), 4.33 (m, 2H), 7.04 (m, 1H), 7.23 (m, 3H); MS m/z MH$^+$ 277.

Method 3

N-{1-(2,2-Dimethyl-1,3-dioxolan-4-ylmethyl)-2-oxo-1,2,3,4-tetrahydroquinolin-3-yl}-2-chloro-6H-thieno[2,3-b]pyrrole-5-carboxamide)

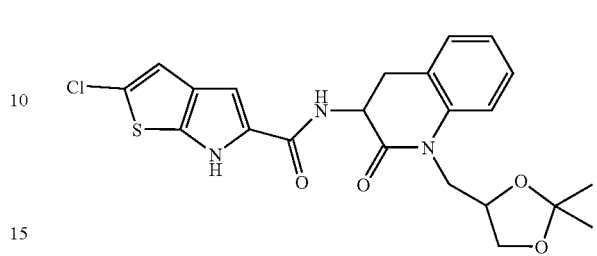

5-Carboxy-2-chloro-6H-thieno[2,3-b]pyrrole (Method 9; 243 mg, 1.20 mmol), HOBT (178 mg, 1.32 mmol), anhydrous DMF (10 mL) and finally EDCI (252 mg, 1.32 mmol) were added to 3-amino-1-[(2,2-dimethyl-1,3-dioxolan-4-yl)methyl]-3,4-dihydroquinolin-2(1H)-one (Method 2, 330 mg, 1.20 mmol) and the reaction was stirred for 18 h. The reaction was evaporated and the residue was dissolved in EtOAc (100 mL) and washed with 1M aqueous HCl (50 mL) and the organic layer was further washed with sat. aqueous NaHCO$_3$ (30 mL) and brine (30 mL). The organic layer was then separated, dried (MgSO$_4$), filtered and evaporated. The residue was purified by column chromatography (EtOAc: hexanes 1:2) to afford the title compound (382 mg, 69%) as a white solid.

$^1$H NMR 1.32 (s, 1.5H), 1.33 (s, 1.5H), 1.37 (s, 1.5H), 1.42 (s, 1.5H), 2.88 (m, 1H), 3.63 (m, 1H), 3.78 (app. t, 1H), 3.90 (dd, 0.5H), 4.04 (dd, 0.5H), 4.14 (m, 1H), 4.33 (m, 2H), 4.68 (m, 1H), 6.82 (m, 2H), 7.10 (m, 1H), 7.27 (m, 4H), 10.94 (br. s, 1H); MS m/z MNa$^+$ 482, 484.

Method 4

3-Chloro-5-methoxycarbonyl-4H-thieno[3,2-b]pyrrole

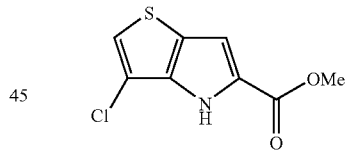

Methanolic sodium methoxide solution (28%) (5 ml, 25.9 mmol) was diluted with MeOH (5 ml) and was cooled to −25° C. under nitrogen. A solution of 4-chloro-2-thienylcarboxaldehyde (J Heterocyclic Chem, 1976, 13, 393; 1.1 g, 7.5 mmol) and methyl azidoacetate (3.0 g, 26.1 mmol) in MeOH (20 ml) was added dropwise, maintaining the temperature at −25° C. On completion of addition the solution was allowed to warm to 5° C. over a period of approximately 16 hours. The solution was added to saturated aqueous ammonium chloride (250 ml) and the mixture was extracted using DCM. The combined organic layers were concentrated at 0° C. The residue was taken up in xylene (30 ml) and this solution was added dropwise to xylene (120 ml) under reflux. The solution was heated under reflux for 30 minutes before being cooled and concentrated. The title compound was purified by a mixture of crystallisation (EtOAc/isohexane) and chromatography on a Bond Elut column eluting with a graduated solvent of 5–50% EtOAc in isohexane (640 mg, 40%). NMR (CDCl$_3$) 9.1 (1H, br), 7.1 (2H, s), 3.9 (3H, s); m/z 214.3.

Methods 5 and 6

The following compounds were made by the process of Method 4 using the appropriate starting materials

| Meth | Compound | NMR (CDCl₃) | M/z |
|---|---|---|---|
| 5[1] | (5,6-dichloro-4H-thieno[3,2-b]pyrrole-2-carboxylic acid methyl ester) | 9.2 (1H, br), 7.0 (1H, s), 3.9 (3H, s) | 248.2 |
| 6[2] | (5-chloro-4H-thieno[2,3-b]pyrrole-2-carboxylic acid methyl ester) | 9.4–9.2 (1H, br), 7.0 (1H, s), 6.9 (1H, s), 3.9 (3H, s) | 214 |

[1] Aldehyde: DE 2814798
[2] Aldehyde: Gronowitz et al. Tetrahedron Vol. 32 1976 p. 1403

Method 7

5-Carboxy-3-chloro-4H-thieno[3,2-b]pyrrole

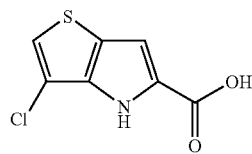

3-Chloro-5-methoxycarbonyl-4H-thieno[3,2-b]pyrrole (Method 4; 0.61 g, 2.83 mmol) was taken up in MeOH (10 ml) and was heated under reflux. Aqueous lithium hydroxide (2.0M, 3.0 ml, 6.0 mmol) was added portionwise over 45 minutes. The mixture was heated under reflux for 30 minutes before being cooled and concentrated. Water (20 ml) was added and the solution was neutralised using aqueous hydrochloric acid (2.0M, 3.0 ml). The solution was extracted using EtOAc, and the combined organic layers were concentrated to afford the title compound as a yellow solid (0.57 g, 100%). NMR: 12.4 (1H, br), 7.4 (1H, s), 7.0 (1H, s); m/z 200.3.

Methods 8 and 9

The following compounds were made by the process of Method 7 using the appropriate starting materials.

| Method | Compound | NMR | M/z | SM |
|---|---|---|---|---|
| 8 | (5,6-dichloro-4H-thieno[3,2-b]pyrrole-2-carboxylic acid) | 7.0 (1H, s) | 234.2 | Method 5 |
| 9 | (5-chloro-4H-thieno[2,3-b]pyrrole-2-carboxylic acid) | 12.6–12.7 (1H, b), 12.0–12.1 (1H, b), 7.15 (1H, s), 6.9 (1H, s) | 183 | Method 6 |

Method 10

3-Amino-1-[2-(dimethylamino)ethyl]-3,4-dihydro-quinolin-2(1H)-one

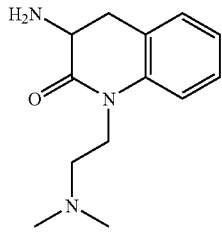

Sodium hydride (60% in oil, 70.5 mg, 1.75 mmol) was added to 3-amino-3,4-dihydroquinolin-2(1H)-one hydrochloride (100 mg, 0.50 mmol), in anhydrous DMF (2 mL) at 0° C. over a period of 5 min. The reaction was stirred for a further 30 min before addition of 2-(dimethylaminoethyl) chloride hydrochloride (80 mg, 0.55 mmol) and the reaction has then heated to 80° C. for a period of 5 hours The reaction was then cooled and evaporated before addition of sat. aqueous $NaHCO_3$ (20 mL) and EtOAc (50 mL). The organic layer was then dried ($MgSO_4$), filtered and evaporated and the residue was used without further purification.

$^1$H NMR 1.25 (s, 2H), 2.35 (s, 6H), 2.56 (m, 2H), 2.81 (d, 1H), 3.05 (dd, 1 H), 3.56 (dd, 1H), 4.08 (m, 2H), 7.15 (m, 4H); MS m/z 234

Method 11

3-Amino-1-[(2,2-dimethyl-1,3-dioxan-5-yl)methyl]-3,4-dihydroquinolin-2(1H)-one

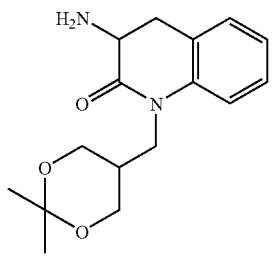

The title compound was prepared in an analogous method to Method 10 using (2,2-dimethyl-1,3-dioxan-5-yl)methyl methanesulfonate [CAS registary number 131372-64-0] as elecrophile.

$^1$H NMR 1.41 (s, 3H), 1.47 (s, 3H), 1.74 (s, 2H), 2.21 (m, 1H), 2.82 (d, 1 H), 3.06 (dd, 1H), 3.57 (dd, 1H), 3.73 (m, 2H), 3.93 (m, 3H), 4.15 (m, 1H), 7.02 (t, 1H), 7.19 (m, 2H), 7.26 (m, 1H); MS m/z 291

Method 12

3-Amino-1-(2-methoxyethyl)-3,4-dihydroquinolin-2(1H)-one

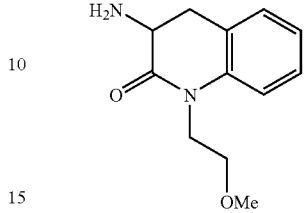

Sodium hydride (60% in oil, 321 mg, 8.03 mmol) was added to 3-amino-3,4-dihydroquinolin-2(1H)-one hydrochloride (J. Med. Chem., 28, 1985; 1511–16; 759 mg, 3.82 mmol) in anhydrous DMF (10 mL) at 0° C. over a period of 5 min. After 1 hour 2-bromoethyl methyl ether (0.40 mL, 4.20 mmol) was added and stirring maintained for 18 hours. The reaction was diluted with EtOAc (100 mL) and washed with sat. aqueous $K_2CO_3$ (20 mL). The aqueous was extracted with DCM (3×50 mL) and the combined organics dried ($Na_2SO_4$), filtered and evaporated. The residue was purified by column chromatography (DCM to DCM:MeOH (4:1)) to afford the title compound (654 mg, 78%) as a brown oil.

$^1$H NMR ($CDCl_3$) 1.82 (br. s, 2H), 2.85 (app. t, 1H), 3.06 (dd, 1H), 3.36 (s, 3 H), 3.61 (m, 3H), 4.02 (dt, 1H), 4.24 (dt, 1H), 7.02 (dt, 1H), 7.19 (m, 2H), 7.27 (t, 1H).

Method 13

3-Amino-1-(2-cyanomethyl)-3,4-dihydroquinolin-2(1H)-one

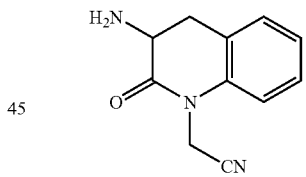

Sodium hydride (60% in oil, 2.74 g, 68.5 mmol) was added to 3-amino-3,4-dihydroquinolin-2(1H)-one hydrochloride (J. Med. Chem., 28, 1985; 1511–16, 6.47 g, 32.6 mmol) in anhydrous DMF (70 mL) at 0° C. over a period of 5 min. After 1 hour the mixture was warmed to ambient temperature, stirred for 2 hours then cooled in an ice bath before bromoacetonitrile (2.28 mL, 32.68 mmol) was added. The mixture was again warmed to ambient temperature and stirred for 18 hours. The reaction was diluted with EtOAc (100 mL) and washed with sat. aqueous $K_2CO_3$ (20 mL). The aqueous was extracted with DCM:MeOH (19:1) (3×50 mL) and the combined organics dried ($Na_2SO_4$), filtered and evaporated. The residue was purified by column chromatography (DCM to DCM:MeOH (9:1)) to afford the title compound (5.28 g, 81%) as a brown oil.

$^1$H NMR ($CDCl_3$) 1.79 (br. s, 2H), 2.90 (app. t, 1H), 3.11 (dd, 1H), 3.65 (dd, 1 H), 4.68 (d, 1H), 5.03 (d, 1H), 7.05 (d, 1H), 7.13 (t, 1H), 7.25 (d, 1H), 7.35 (t, 1H); MS m/z 202.

Method 14

N-[1-((2Z)-2-Amino-2-{[(ethoxycarbonyl)oxy]imino}ethyl)-2-oxo-1,2,3,4-tetrahydroquinolin-3-yl]-2-chloro-6H-thieno[2,3-b]pyrrole-5-carboxamide

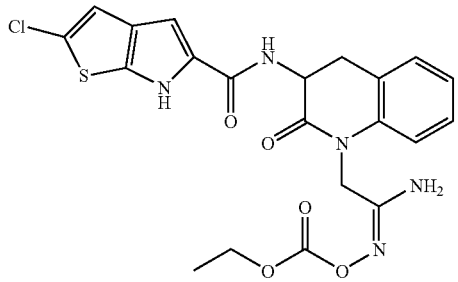

Ethyl chloroformate (60 µL, 0.63 mmol) was added to a suspension of N-{1-[(2Z)-2-amino-2-(hydroxyimino)ethyl]-2-oxo-1,2,3,4-tetrahydroquinolin-3-yl}-2-chloro-6H-thieno[2,3-b]pyrrole-5-carboxamide (Example 31; 200 mg, 0.48 mmol) in dry pyridine (1 mL) under an inert atmosphere then stirred heated to 100° C. for 30 minutes. On cooling THF (10 mL) and added followed by EtOAc (50 mL) and 1M HCl aq. (20 mL). The organic was separated and dried (Na$_2$SO$_4$), filtered and evaporated to give a clear orange oil. This was used in the next stage without characterization or purification.

Method 15

2-Chloro-N-[1-(2-hydrazino-2-oxoethyl)-2-oxo-1,2,3,4-tetrahydroquinolin-3-yl]-6 H-thieno[2,3-b]pyrrole-5-carboxamide

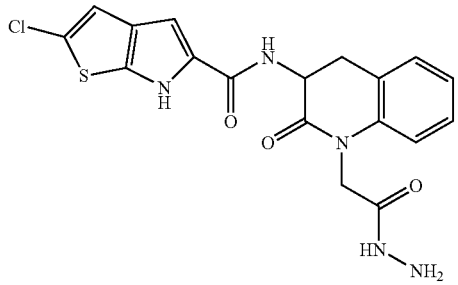

Hydrazine monohydrate (1 mL, 20.6 mmol) was added to a suspension of methyl[3-{[(2-chloro-6H-thieno[2,3-b]pyrrol-5-yl)carbonyl]amino}-2-oxo-3,4-dihydroquinolin-1(2H)-yl]acetate (Example 1); 221 mg, 0.53 mmol) in EtOH (10 mL) and heated to reflux for 20 hours. On cooling the mixture was concentrated under reduced pressure and H$_2$O (20 mL) added and the white precipitate filtered off and dried in vacuo to give the title product (169 mg, 76%) as an off white solid.

$^1$H NMR 3.04 (dd, 1H), 3.18 (app. t, 1H), 4.25 (br. s, 2H), 4.33 (d, 1H), 4.69 (d, 1H), 4.88 (m, 1H), 6.93 (d, 1H), 7.06 (t, 1H), 7.11 (s, 1H), 7.19 (s, 1H), 7.28 (m, 2H), 7.32 (m, 2H), 8.52 (d, 1H), 9.29 (br. s, 1H), 11.67 (br. s, 1H); MS m/z 418, 420.

Method 16

3-Amino-1-[2-(methylthio)ethyl]-3,4-dihydroquinolin-2(1H)-one

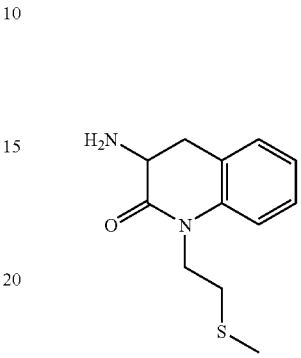

Prepared by an analogous method to 3-amino-1-(2-methoxyethyl)-3,4-dihydroquinolin-2(1H)-one (Method 12) using 2-chloroethyl methyl sulphide instead of 2-bromoethyl methyl ether to give the title product as a clear, brown gum.

$^1$H NMR 2.13 (s, 3H), 2.66 (t, 2H), 2.73 (app. t, 1H), 2.96 (dd, 1H), 3.44 (dd, 1H) 4.09 (t, 2H), 7.01 (t, 1H), 7.14 (d, 1H), 7.23 (m, 2H).

Method 17

2,3-Dichloro-N-{1-[(2R)-2,3-dihydroxypropyl]-2-oxo-1,2,3,4-tetrahydroquinolin-3-yl}-4H-thieno[3,2-b]pyrrole-5-carboxamide

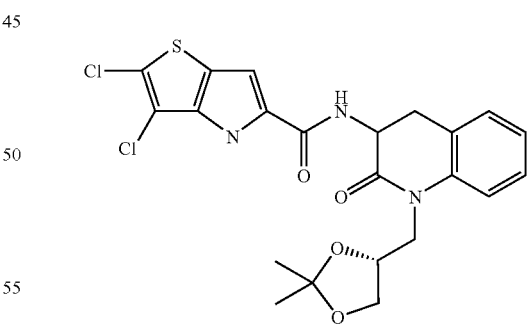

Standard amide bond formation analogous to Method 3 except using 3-amino-1-[(2R)-2,3-dihydroxypropyl]-3,4-dihydroquinolin-2(1H)-one (Method 18) as amine and 2,3-dichloro-4H-thieno[3,2-b]pyrrole-5-carboxylic acid as the acid component formed the title compound as a white solid.

$^1$H NMR 1.23 (s, 3H), 1.30 (s, 3H), 3.12 (m, 2H), 3.71 (m, 1H), 4.15 (m, 4 H), 4.72 (m, 1H), 7.05 (t, 1H), 7.20 (s, 1H), 7.31 (m, 3H), 8.60 (d, 1H), 12.49 (s, 1 H); MS m/z 456

Method 18

3-amino-1-{[(4R)-2,2-dimethyl-1,3-dioxolan-4-yl]methyl}-3,4-dihydroquinolin-2(1H)-one

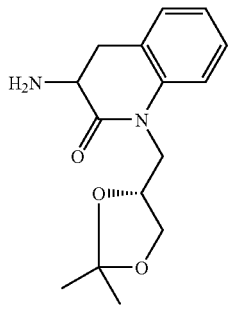

Prepared according to Method 2 using [(4S)-2,2-dimethyl-1,3-dioxolan-4-yl]methyl methanesulfonate (*J. Org. Chem*, 64, 1999 6782–6790) to give the title compound as a pale yellow oil.

$^1$H NMR (CDCl$_3$) 1.42 (m, 6H), 2.99 (m, 2H), 3.60 (m, 1H), 3.83 (m, 1.5H), 4.11 (m, 1.5H), 4.38 (m, 2H), 7.03 (m, 1H), 7.26 (d, 3H).

Method 19

3-Amino-1-(oxiran-2-ylmethyl)-3,4-dihydroquinolin-2(1H)-one

The title compound was prepared in an analogous method to Method 1 using glycidyl tosylate as elecrophile.

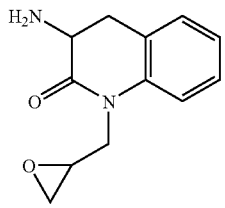

$^1$H NMR 2.70 (m, 1.5H), 3.25 (m, 4H), 4.12 (dd, 0.5H), 4.32 (dd, 0.5H), 4.70 (dd, 0.5H), 7.20 (m, 4H); MS m/z 219

Method 20

N-[1-(3-{[tert-Butyl(dimethyl)silyl]oxy}propyl)-2-oxo-1,2,3,4-tetrahydroquinolin-3-yl]-2-chloro-6H-thieno[2,3-b]pyrrole-5-carboxamide

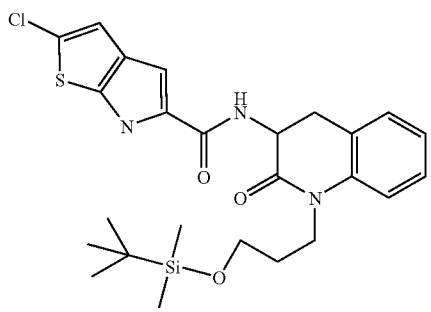

Standard amide bond formation analogous to Method 3 except using 3-amino-1-(3-{[tert-butyl(dimethyl)silyl]oxy}propyl)-3,4-dihydroquinolin-2(1H)-one (Method 21) as amine and 2-chloro-6H-thieno[2,3-b]pyrrole-5-carboxylic acidas the acid component formed the title compound as a white solid.

$^1$H NMR 0.00 (s, 6H), 0.87 (s, 9H), 1.85 (m, 2H), 2.79 (t, 1H), 3.60 (m, 3 H), 4.05 (m, 2H), 4.56 (m, 1H), 6.77 (s, 1H), 6.82 (s, 1H), 7.02 (t, 1H), 7.20 (m, 4H), 10.47 (s, 1H); MS m/z 518

Method 21

3-Amino-1-(3-{[tert-butyl(dimethyl)silyl]oxy}propyl)-3,4-dihydroquinolin-2(1H)-one

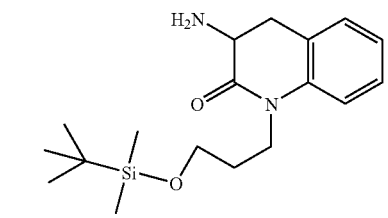

The title compound was prepared in an analogous method to Method 1 using (3-bromopropoxy)(tert-butyl)dimethylsilane as electrophile.

$^1$H NMR 0.00 (s, 6H), 0.88 (s, 9H), 1.75 (s, 2H), 1.83 (m, 2H), 2.74 (d, 1 H), 3.00 (dd, 1H), 3.48 (dd, 1H), 3.66 (m, 2H), 3.98 (m, 2H), 6.96 (t, 1H), 7.16 (m, 3H); MS m/z 335

Method 22

3-Amino-1-(2-oxobutyl)-3,4-dihydroquinolin-2(1H)-one

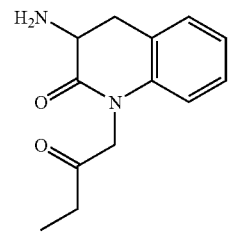

The title compound was prepared in an analogous method to Method 1 using 1-bromo-2-butanone as electrophile.

$^1$H NMR 1.14 (t, 1H), 1.84 (br, 2H), 2.55 (q, 2H), 2.93 (m, 1H), 3.12 (dd, 1 H), 3.67 (dd, 1H), 4.49 (d, 1H), 4.92 (d, 1H), 6.61 (d, 1H), 7.03 (t, 1H), 7.20 (t, 2H); MS m/z 233

Method 23

(6S)-6-(Tritylamino)-5,6-dihydroimidazo[1,2-a]pyrimidin-7(8H)-one

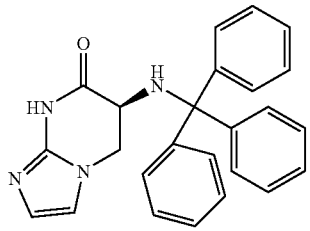

10% Pd/C (260 mg) was added to a solution of methyl 3-(2-nitro-1H-imidazol-1-yl)-N-trityl-L-alaninate (Method 24, 1.2 g, 2.6 mmol) in EtOH (100 mL) and the reaction stirred under an atmosphere of hydrogen for 2 hours The reaction was filtered through celite and the filtrate heated at reflux for approximately 2 hours Upon cooling the volatiles were removed by evaporation under reduced pressure to afford the title compound (1.04 g, 100%) as a white solid.

$^1$H NMR 2.63 (dd, 1H), 3.30 (t, 1H), 3.58 (dd, 1H), 4.13 (s, 1H), 6.20 (d, 1 H), 6.72 (d, 1H), 7.23 (m, 9H), 7.35 (m, 6H); MS m/z 395.

Method 24

Methyl 3-(2-nitro-1H-imidazol-1-yl)-N-trityl-L-alaninate

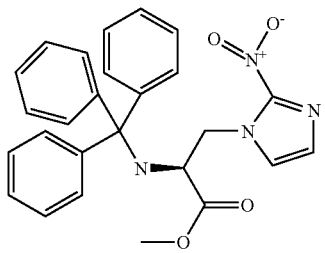

Di-isopropylazodicarboxylate (1.3 mL, 6.6 mmol) was added dropwise to a solution of 2-nitroimidazole (1.0 g, 9 mmol), N-trityl-L-serine methyl ester (2.0 g, 6 mmol) and triphenylphosphine (1.73 g, 6.6 mmol) in THF (100 mL). The reaction was stirred at ambient temperature for approximately 5 hours The volatiles were removed by evaporation under reduced pressure and the residue purified by column chromatography (EtOAc:isohexane 1:19) to afford the title compound (1.2 g, 44%) as a white solid.

$^1$H NMR 3.08 (s, 3H), 3.16 (d, 1H), 3.69 (m, 1H), 4.46 (dd, 1H), 4.62 (dd, 1 H), 7.15 (m, 15H), 7.33 (s, 1H), 7.93 (s, 1H); MS m/Z (M+NH$_4$)$^+$ 479.

Method 25

3-Amino-3,4-dihydro-1,5-naphthyridin-2(1H)-one dihydrochloride

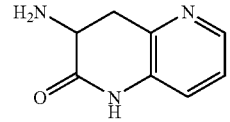

tert-Butyl(2-oxo-1,2,3,4-tetrahydro-1,5-naphthyridine-3-yl)carbamate (Method 26, 263 mg, 1 mmol) was dissolved in DCM (10 mL) and treated with 4M HCl in dioxan (10 mL). After stirring at ambient temperature for 30 mins. the reaction mixture was evaporated under reduced pressure and the residue triturated with ether (20 mL), to give a white solid which was collected by filtration, washed with ether and dried. (234 mg, 100%).

$^1$H NMR 3.4 (m, 1H); 3.4 (m, 1H); 4.5 (m, 1H); 7.5 (m, 2H); 8.3 (d, 1H); 8.75 (bs, 3H); 11.18(s, 1H) MS m/z 164

Method 26 tert-Butyl(2-oxo-1,2,3,4-tetrahydro-1,5-naphthyridine-3-yl)carbamate

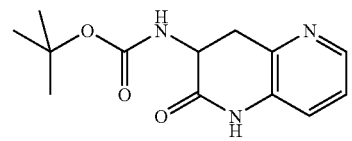

Methyl 2-[(tert-butoxycarbonyl)amino]-3-(3nitropyridin-2-yl)acrylate (4:1 mixture of Z/E isomers) (Method 27, 1.1 g, 3.4 mmol) was dissolved in ethanol and 10% palladium on carbon catalyst (250 mg) was added. The mixture was stirred under 1 atmosphere of hydrogen at ambient temperature for 12 hours. After removing the catalyst by filtration through Celite, the filtrate was concentrated under reduced pressure to give a yellow oil. The oil was dissolved in methanol (20 mL) and treated with a 0.5M solution of sodium methoxide in methanol (8 mL). After stirring at ambient temperature for 4 hrs. the mixture was diluted with water (100 mL) and extracted with ethyl acetate (2×50 mL). The combined extracts were washed with water (2×50 mL) and brine (50 mL), dried (MgSO$_4$) and evaporated under reduced pressure to give a white solid (528 mg, 59%)

$^1$H NMR 1.4 (s, 9H); 3.1 (m, 2H); 4.3 (m, 1H); 7.0 (bd, 1H); 7.2 (m, 2H); 8.1 (t, 1H); 10.26 (s, 1H); MS m/z 208.

Method 27

Methyl 2-[(tert-butoxycarbonyl)amino]-3-(3nitropyridin-2-yl)acrylate

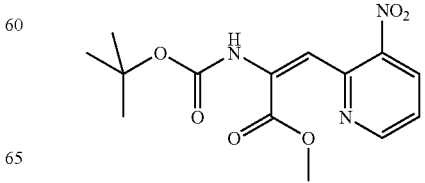

Methyl[(tert-butoxycarbonyl)amino](dimethoxyphosphoryl)acetate (1.33 g, 4.46 mmol) was dissolved in dry THF (20 mL) and cooled to −78° C. under nitrogen. Tetramethylguanidine (490 mg, 4.26 mmol) was added and the solution stirred at −78° C. for a further 10 mins. A solution of 3-nitropyridine-2-carbaldehyde (Tetrahedron vol 0.54 (1998) p 6311) (618 mg, 4.06 mmol) in dry THF (5 mL.) was added drop wise. After stirring the solution for 2 hours. at −78° C. (50 mL) it was diluted with water (150 mL) and extracted with ethyl acetate. The combined extracts were washed with water (2×20 mL) and brine (20 mL), dried (MgSO₄) and evaporated under reduced pressure to give a yellow oil, which was purified by column chromatography (DCM) to give the title compound as a 4:1 mixture of Z/E isomers (1.1 g, 84%).

¹H NMR 1.4 (s, 11.25H); 3.6 (s, 0.75H); 3.8 (s,3H); 6.7 (s, 1H); 6.9 (s, 0.25H); 7.45 (m, 0.25H); 7.6 (m, 1H); 8.37 (d, 0.25H); 8.5 (d, 1H); 8.7 (d, 0.25H); 8.9 (d, 1H); 9.8 (s, 0.25H); 10.3 (s, 1H); MS m/z 322

Method 28

3-Amino-3,4-dihydro-1,7-naphthfridin-2(1H)-one

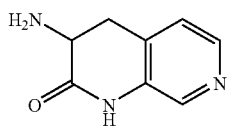

tert-Butyl(2-oxo-1,2,3,4-tetrahydro-1,7-naphthyridine-3-yl)carbamate (Method 29, 284 mg) was dissolved in DCM (10 mL) and treated with trifluoroacetic acid (5 mL). After stirring at ambient temperature for 1 hour the reaction mixture was evaporated under reduced pressure and the residue triturated with ether (20 mL), to give a light brown solid which was collected by filtration, washed with ether and dried to give the title compound (346 mg, 82%) as a bis trifluroacetate salt.

¹H NMR 3.2 (m, 2H); 4.3 (m, 1H), 7.4 (d, 1H); 8.2 (s, 1H); 8.25 (d, 1H); 8.6 (b, 3H); 11.0 (s, 1H)

Method 29 tert-Butyl(2-oxo-1,2,3,4-tetrahydro-1,7-naiphthyridine-3-yl)carbamate

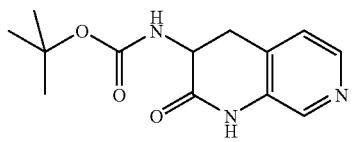

Methyl 2-[(tert-butoxycarbonyl)amino]-3-(3nitropyridin-4-yl)acrylate (10:1 mixture of Z/E isomers) (Method 30, 1.57 g, 4.83 mmol) was dissolved in ethanol and 10% palladium on carbon catalyst (250 mg) was added. The mixture was stirred under 1 atmosphere of hydrogen at ambient temperature for 6 hours. After removing the catalyst by filtration through Celite the filtrate was concentrated under reduced pressure to give a yellow oil which was purified by column chromatography (Eluent DCM/MeOH gradient 0–10%) to give the title compound (284 mg, 22%).

¹H NMR 1.4 (s, 9H); 3.0 (m, 2H); 4.2 (m, 1H); 7.0 (d, 1H); 7.2 (d,1H); 8.1 (m, 2H); 10.36 (s, 1H); MS m/z 264.

Method 30

Methyl-2-[(tert-butoxycarbonyl)amino]-3-(3nitropyridin-4-yl)acrylate

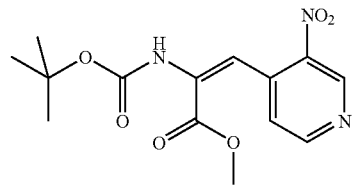

Methyl[(tert-butoxycarbonyl)amino](dimethoxyphosphoryl)acetate (1.73 g, 5.82 mmol) was dissolved in dry THF (20 mL) and cooled to −78° C. under nitrogen. Tetramethylguanidine (638 mg., 5.55 mmol) was added and the solution stirred at −78° C. for a further 10 mins. A solution of 3-nitroisonicotinaldehyde (Method 31, 804 mg, 5.29 mmol) in dry THF (5 mL) was added dropwise. The resulting deep red solution was stirred for 2 hrs. at −78° C., then poured into a mixture of ethyl acetate (100 mL) and water (50 mL). The organic layer was separated, washed with water (2×50 mL) and brine (25 mL), dried (MgSO₄) and evaporated under reduced pressure to give a yellow oil, which was purified by column chromatography (EtOAc:isohexane 1:1) to give the title compound as a 10:1 mixture of Z/E isomers (1.57 g, 92%).

¹H NMR 1.3 (s, 9H); 1.4 (s, 0.9H); 3.55 (s, 0.3H); 3.8 (s, 3H); 6.6 (s, 0.1 H); 7.2 (s, 1H); 7.25(d, 0.1H); 7.5 (d, 1H); 8.75 (d, 0.1H); 8.8 (s, 1.1H); 8.85 (d, 1H); 9.2 (s, 0.11H); 9.25 (s, 1H); MS m/z 322.

Method 31

3-Nitroisonicotinaldehyde

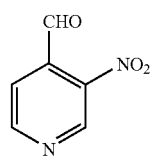

4-Methyl-nitropyridine (1.43 g, 10.36 mmol) was dissolved in dry DME (5 mL) and dimethylformamide dimethyl acetal (2.0 g, 16.8 mmol) was added. The mixture was heated under nitrogen at 140° C. for 2 hours and then evaporated under reduced pressure to give (E)-N,N-dimethyl-2-(3-nitropyridin-4-yl)ethyleneamine as a dark red solid. This was added in one portion at ambient temperature to a stirred solution of sodium periodate (6.61 g, 31 mmol) in THF/Water 1:1 (100 mL). After stirring for 2 hr at ambient temperature the reaction mixture was filtered and the solid washed with ethyl acetate (100 mL). The washings were combined with the filtrate and organic layer separated. The aqueous was extracted with ethyl acetate (2×100 mL) and the combined organic layers were washed with saturated aqueous sodium bicarbonate (100 mL) and brine (100 mL), dried (MgSO$_4$) and evaporated under reduced pressure to give a brown solid which was purified by column chromatography (DCM) to give the title compound. (960 mg, 61%).

$^1$HNMR 7.8 (d, 1H); 9.15 (d, 1H); 9.4(s, 1H); 10.4 (s, 1H)

The invention claimed is:

1. A compound of formula (1):

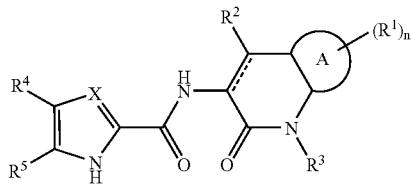

wherein

----- is a single or double bond;

X is N or CH;

R$^4$ and R$^5$ together are —S—C(R$^6$)=C(R$^7$)— or —C(R$^7$)=C(R$^6$)—S—;

R$^6$ and R$^7$ are both chloro or one of R$^6$ and R$^7$ is chloro and the other is hydrogen A is phenylene or heteroarylene;

n is 0, 1, or 2;

R$^1$ is independently selected from halo, nitro, cyano, hydroxy, carboxy, carbamoyl, N—C$_{1-4}$alkylcarbamoyl, N,N—(C$_{1-4}$alkyl)$_2$carbamoyl, sulphamoyl, N—C$_{1-4}$alkylsulphamoyl, N,N—(C$_{1-4}$alkyl)$_2$sulphamoyl, —S(O)$_b$C$_{1-4}$alkyl (wherein b is 0, 1, or 2), C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, hydroxyC$_{1-4}$alkyl, fluoromethyl, difluoromethyl, trifluoromethyl, and trifluoromethoxy; or when n is 2, the two R$^1$ groups, together with the carbon atoms of A to which they are attached, may form a 4- to 7-membered ring, optionally containing 1 or 2 heteroatoms independently selected from O, S, and N, and optionally being substituted with one or two methyl groups;

R$^2$ is hydrogen, hydroxy, or carboxy;

R$^3$ is selected from hydrogen, hydroxy, C$_{1-4}$alkoxy, C$_{1-4}$alkanoyl, carbamoyl, C$_{3-7}$cycloalkyl (optionally substituted with 1 or 2 hydroxy groups), cyano(C$_{1-4}$) alkyl, aryl, heterocyclyl, C$_{1-4}$alkyl (optionally substituted with 1 or 2 R$^8$ groups), and groups of the formulae B or B'

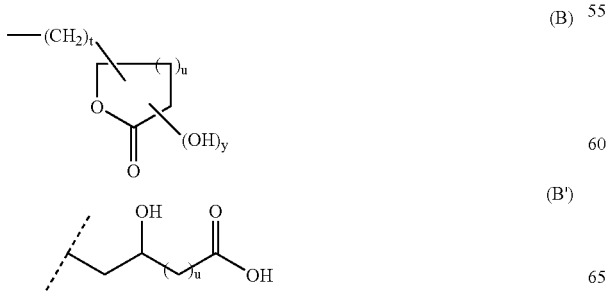

wherein y is 0 or 1, t is 0, 1, 2, or 3 and u is 1 or 2; provided that the hydroxy group is not a substituent on the ring carbon adjacent to the ring oxygen;

R$^8$ is independently selected from hydroxy, C$_{1-4}$alkoxyC$_{1-4}$alkoxy, hydroxyC$_{1-4}$alkoxy, 5- and 6-membered cyclic acetals and mono- and di-methyl derivatives thereof, aryl, heterocyclyl, C$_{3-7}$cycloalkyl, C$_{1-4}$alkanoyl, C$_{1-4}$alkoxy, C$_{1-4}$alkylS(O)$_b$— (wherein b is 0, 1, or 2), C$_{3-6}$cycloalkylS(O)$_b$— (wherein b is 0, 1, or 2), arylS(O)$_b$— (wherein b is 0, 1, or 2), heterocyclylS(O)$_b$— (wherein b is 0, 1, or 2), benzylS(O)$_b$— (wherein b is 0, 1, or 2), —N(OH)CHO, —C(=N—OH)NH$_2$, —C(=N—OH)NHC$_{1-4}$alkyl, —C(=N—OH)N(C$_{1-4}$ alkyl)$_2$, —C(=N—OH)NHC$_{3-6}$cycloalkyl, —C(=N—OH)N(C$_{3-6}$cycloalkyl)$_2$, —COCOOR$^9$, —C(O)N(R$^9$)(R$^{10}$), —NHC(O)R$^9$, —C(O)NHSO$_2$(C$_{1-4}$alkyl), —NHSO$_2$R$^9$, (R$^9$)(R$^{10}$)NSO$_2$—, —COCH$_2$OR$^{11}$, (R$^9$)(R$^{10}$)N—, and —COOR$^9$;

R$^9$ and R$^{10}$ are independently selected from hydrogen, hydroxy, C$_{1-4}$alkyl (optionally substituted with 1 or 2 R$^{13}$), C$_{3-7}$cycloalkyl (optionally substituted with 1 or 2 hydroxy groups), cyano(C$_{1-4}$)alkyl, trihalo(C$_{1-4}$)alkyl, aryl, heterocyclyl, and heterocyclyl(C$_{1-4}$ alkyl); or R$^9$ and R$^{10}$ together with the nitrogen to which they are attached form a 4- to 6-membered ring where the ring is optionally substituted on carbon with 1 or 2 substituents independently selected from oxo, hydroxy, carboxy, halo, nitro, cyano, carbonyl, C$_{1-4}$alkoxy, and heterocyclyl; or the ring may be optionally substituted on two adjacent carbons with —O—CH$_2$—O— to form a cyclic acetal wherein one or both of the hydrogens of the —O—CH$_2$—O— group may be replaced by a methyl;

R$^{13}$ is selected from hydroxy, halo, trihalomethyl, and C$_{1-4}$alkoxy; and R$^{11}$ is independently selected from hydrogen, C$_{1-4}$alkyl, and hydroxyC$_{1-4}$alkyl;

or a pharmaceutically acceptable salt or prodrug thereof; with the proviso that the compound of formula (1) is not:

(i) 2,3-dichloro-5-[N-(2-oxo-1,2,3,4-tetrahydroquinol-3-yl)carbamoyl]4H-thieno[3,2-b]pyrrole;

(ii) 2-chloro-5-[N-(2-oxo-1,2,3,4-tetrahydroquinol-3-yl)carbamoyl]-6H-thieno[2,3-b]pyrrole; or (iii) 2-chloro-5-[N-(1-methyl-2-oxo-1,2,3,4-tetrahydroquinol-3-yl)carbamoyl]-6H-thieno[2,3-b]pyrrole.

2. A compound of claim 1, wherein

R$^3$ is selected from hydrogen, hydroxy, C$_{1-4}$alkoxy, C$_{1-4}$alkanoyl, carbamoyl, C$_{3-7}$cycloalkyl (optionally substituted with 1 or 2 hydroxy groups), cyano(C$_{1-4}$) alkyl, morpholino, morpholinyl, piperidino, piperidyl, pyridyl, pyranyl, pyrrolyl, imidazolyl, thiazolyl, thienyl, thiadiazolyl, piperazinyl, isothiazolidinyl, 1,3,4-triazolyl, tetrazolyl, pyrrolidinyl, thiomorpholino, pyrrolinyl, homopiperazinyl, 3,5-dioxapiperidinyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, 1,3,4-oxadiazolyl, 1,2,4-oxadiazolyl, tetrahydrothiopyranyl, 1-oxotetrahydrothiopyranyl, 1,1-dioxotetrahydrothiopyranyl, and C$_{1-4}$alkyl (optionally substituted with 1 or 2 R$^8$ groups);

R$^9$ and R$^{10}$ are independently selected from hydrogen, hydroxy, C$_{1-4}$alkyl (optionally substituted with 1 or 2 R$^{13}$ groups), C$_{3-7}$cycloalkyl (optionally substituted with 1 or 2 hydroxy groups), cyano($C_{1-4}$)alkyl, trihalo $C_{1-4}$alkyl, aryl, heterocyclyl, and heterocyclyl ($C_{1-4}$alkyl); or $R^9$ and $R^{10}$ together with the nitrogen to which they are attached form a 4- to 6-membered ring where the ring is optionally substituted on carbon with 1 or 2 substituents selected from oxo, hydroxy, carboxy, halo, nitro, cyano, carbonyl, and $C_{1-4}$alkoxy, or the ring may be optionally substituted on two adjacent carbons with —O—$CH_2$—O— to form a cyclic acetal wherein one or both of the hydrogens of the —O—$CH_2$—O— group may be replaced by a methyl;

$R^8$ is independently selected from hydroxy, $C_{1-4}$alkoxy$C_{1-4}$alkoxy, hydroxy$C_{1-4}$alkoxy, 5- and 6-membered cyclic acetals and mono- and di-methyl derivatives thereof, aryl, heterocyclyl, $C_{3-7}$cycloalkyl, $C_{1-4}$alkanoyl, $C_{1-4}$alkoxy, $C_{1-4}$alkylS$(O)_b$— (wherein b is 0, 1, or 2), $C_{3-6}$cycloalkylS$(O)_b$— (wherein b is 0, 1, or 2), arylS$(O)_b$— (wherein b is 0, 1, or 2), heterocyclylS$(O)_b$— (wherein b is 0, 1, or 2), benzylS$(O)_b$— (wherein b is 0, 1, or 2), —N(OH)CHO, —C(=N—OH)$NH_2$, —C(=N—OH)NH$C_{1-4}$alkyl, —C(=N—OH)N($C_{1-4}$ alkyl)$_2$, —C(=N—OH)NH$C_{3-6}$cycloalkyl, —C(=N—OH)N($C_{3-6}$cycloalkyl)$_2$, —COCOO$R^9$, —C(O)N($R^9$)($R^{10}$), —NHC(O)$R^9$, —C(O)NHSO$_2$($C_{1-4}$alkyl), —NHSO$_2R^9$, ($R^9$)($R^{10}$)NSO$_2$—, —CO$CH_2$O$R^{11}$, ($R^9$)($R^{10}$)N—, and —COO$R^9$;

$R^{13}$ is selected from hydroxy, halo, trifluoromethyl, and $C_{1-4}$alkoxy; and $R^{11}$ is selected from hydrogen, $C_{1-4}$alkyl, and hydroxy$C_{1-4}$alkyl;

or a pharmaceutically acceptable salt or in-vivo hydrolysable ester thereof;

provided that the compound of formula (1) is not
(i) 2,3-dichloro-5-[N-(2-oxo-1,2,3,4-tetrahydroquinol-3-yl)carbamoyl]-4H-thieno[3,2-b]pyrrole;
(ii) 2-chloro-5-[N-(2-oxo-1,2,3,4-tetrahydroquinol-3-yl)carbamoyl]-6H-thieno[2,3-b]pyrrole; or
(iii) 2-chloro-5-[N-(1-methyl-2-oxo-1,2,3,4-tetrahydroquinol-3-yl)carbamoyl]-6H-thieno[2,3-b]pyrrole.

3. A compound of claim 1, wherein
$R^3$ is selected from cyano$C_{1-4}$alkyl and $C_{1-4}$alkyl (optionally substituted with 1 or 2 $R^8$ groups);
$R^8$ is independently selected from hydroxy, phenyl, 2,2-dimethyl-1,3-dioxolan-4-yl, 2,2-dimethyl-1,3-dioxan-4-yl; 2,2-dimethyl-1,3-dioxan-5-yl, 1,2,4-oxadiazolyl, 1,3,4-oxadiazolyl, triazolyl, tetrazolyl, imidazolyl, pyrrolidinyl, piperidyl, tetrahydrofuryl, tetrahydropyranyl, tetrahydrothiopyranyl, tetrahydrothienyl, $C_{1-4}$alkoxy, $C_{1-4}$alkanoyl, $C_{1-4}$alkylS$(O)_b$— (wherein b is 0, 1, or 2), —C(O)N($R^9$)($R^{10}$), —COO$R^9$, —C(O)NHSO$_2$Me, —C(=N—OH)$NH_2$, —C(=N—OH)NH$C_{1-4}$alkyl, —C(=N—OH)N($C_{1-4}$alkyl)$_2$, and —NHSO$_2R^9$; and
$R^9$ and $R^{10}$ are independently selected from hydrogen, hydroxy, and $C_{1-4}$alkyl optionally substituted with $R^{13}$ (wherein $R^{13}$ is $C_{1-4}$alkoxy or hydroxy); or
$R^9$ and $R^{10}$ together with the nitrogen to which they are attached form a 4- to 6-membered ring where the ring may be optionally substituted on carbon with 1 or 2 hydroxy groups or carboxy groups, or the ring may be optionally substituted on two adjacent carbons with —O—$CH_2$—O— to form a cyclic acetal wherein one or both of the hydrogens of the —O—$CH_2$—O— group may be replaced by a methyl.
or a pharmaceutically acceptable salt or in-vivo hydrolysable ester thereof;

provided that the compound of formula (1) is not:
2-chloro-5-[N-(1-methyl-2-oxo-1,2,3,4-tetrahydroquinol-3-yl)carbamoyl]-6H-thieno[2,3-b]pyrrole.

4. A compound of claim 1, wherein
$R^3$ is selected from cyano, $C_{1-4}$alkyl and $C_{1-4}$alkyl (optionally substituted with 1 or 2 $R^8$ groups);
$R^8$ is independently selected from hydroxy, 2,2-dimethyl-1,3-dioxolan-4-yl, 1,2,4-oxadiazolyl, 1,3,4-oxadiazolyl, tetrazolyl, $C_{1-4}$alkoxy, $C_{1-4}$alkanoyl, $C_{1-4}$alkylS$(O)_b$— (wherein b is 0, 1, or 2), —C(O)N($R^9$)($R^{10}$), —COO$R^9$, —C(O)NHSO$_2$Me, and —C(=N—OH)$NH_2$; and
$R^9$ and $R^{10}$ are independently selected from hydrogen, hydroxy, and $C_{1-4}$alkyl optionally substituted with $R^{13}$ (wherein $R^{13}$ is $C_{1-4}$alkoxy or hydroxy); or
$R^9$ and $R^{10}$ together with the nitrogen to which they are attached form a 4- to 6-membered ring selected from piperidine, 4-hydroxy piperidine, pyrrolidine, 3,4-dihydroxypyrrolidine, and the dimethylacetal of 3,4-dihydroxypyrrolidine;

or a pharmaceutically acceptable salt or in-vivo hydrolysable ester thereof;

provided that the compound of formula (1) is not
2-chloro-5-[N-(1-methyl-2-oxo-1,2,3,4-tetrahydroquinol-3-yl)carbamoyl]-6H-thieno[2,3-b]pyrrole.

5. A compound of claim 1, wherein
$R^4$ and $R^5$ together are —S—C($R^6$)=C($R^7$)— or a pharmaceutically acceptable salt or in-vivo hydrolysable ester thereof.

6. A compound of claim 1, wherein
$R^4$ and $R^5$ together are —C($R^7$)=C($R^6$)—S—, or a pharmaceutically acceptable salt or in-vivo hydrolysable ester thereof.

7. A compound of claim 1, wherein X is CH, or a pharmaceutically acceptable salt or in-vivo hydrolysable ester thereof.

8. A compound of claim 1, wherein X is N, or a pharmaceutically acceptable salt or in-vivo hydrolysable ester thereof.

9. A compound of claim 1, wherein A is phenylene, or a pharmaceutically acceptable salt or in-vivo hydrolysable ester thereof.

10. A compound of claim 1, wherein A is heteroarylene, or a pharmaceutically acceptable salt or in-vivo hydrolysable ester thereof.

11. A compound of claim 1, wherein

===== is a single bond, or a pharmaceutically acceptable salt or in-vivo hydrolysable ester thereof.

12. A compound of claim 1, selected from
2-chloro-N-[1-(methoxycarbonylmethyl)-2-oxo-1,2,3,4-tetrahydroquinolin-3-yl]-6H-thieno[2,3-b]pyrrole-5-carboxamide;
N-[1-(carboxymethyl)-2-oxo-1,2,3,4-tetrahydroquinolin-3-yl]-2-chloro-6H-thieno[2,3-b]pyrrole-5-carboxamide;
2-chloro-N-[1-(carbamoylmethyl)-2-oxo-1,2,3,4-tetrahydroquinolin-3-yl]-6H-thieno[2,3-b]pyrrole-5-carboxamide;
2-chloro-N-[1-(N,N-dimethylcarbamoylmethyl)-2-oxo-1,2,3,4-tetrahydroquinolin-3-yl]-6H-thieno[2,3-b]pyrrole-5-carboxamide;

2-chloro-N-[1-(N-methylcarbamoylmethyl)-2-oxo-1,2,3,4-tetrahydroquinolin-3-yl]-6H-thieno[2,3-b]pyrrole-5-carboxamide;

2-chloro-N-[1-(N-hydroxycarbamoylmethyl)-2-oxo-1,2,3,4-tetrahydroquinolin-3-yl]-6H-thieno[2,3-b]pyrrole-5-carboxamide;

2-chloro-N-{1-[N-(2-hydroxyethyl)carbamoylmethyl]-2-oxo-1,2,3,4-tetrahydroquinolin-3-yl}-6H-thieno[2,3-b]pyrrole-5-carboxamide;

2-chloro-N-[1-(2-hydroxyethyl)-2-oxo-1,2,3,4-tetrahydroquinolin-3-yl]-6H-thieno[2,3-b]pyrrol-5-ylcarboxamide;

2-chloro-N-[1-(2,3-dihydroxypropyl)-2-oxo-1,2,3,4-tetrahydroquinolin-3-yl]-6H-thieno[2,3-b]pyrrole-5-carboxamide;

2-chloro-N-{1-[(2,2-dimethyl-1,3-dioxolan-4(S)-yl)methyl]-2-oxo-1,2,3,4-tetrahydroquinolin-3(R,S)-yl}-6H-thieno[2,3-b]pyrrole-5-carboxamide;

2-chloro-N-[1-(2(S),3-dihydroxypropyl)-2-oxo-1,2,3,4-tetrahydroquinolin-3 (R,S)-yl]-6H-thieno[2,3-b]pyrrole-5-carboxamide;

2-chloro-N-[1-(2,2-dimethyl-1,3-dioxolan-4(R)-ylmethyl)-2-oxo-1,2,3,4-tetrahydroquinolin-3(R,S)-yl]-6H-thieno[2,3-b]pyrrole-5-carboxamide 2-chloro-N-[1-(2(R),3-dihydroxypropyl)-2-oxo-1,2,3,4-tetrahydroquinolin-3(R,S)-yl]-6H-thieno[2,3-b]pyrrole-5-carboxamide;

2-chloro-N-{1-[2-(4-hydroxypiperidin-1-yl)-2-oxoethyl]-2-oxo-1,2,3,4-tetrahydroquinolin-3-yl}-6H-thieno[2,3-b]pyrrole-5-carboxamide;

2-chloro-N-{1-[N-(1,3-dihydroxyprop-2-yl)carbamoylmethyl]-2-oxo-1,2,3,4-tetrahydroquinolin-3-yl}-6H-thieno[2,3-b]pyrrole-5-carboxamide;

2-chloro-N-{1-[N-(2-Methoxyethyl)carbamoylmethyl]-2-oxo-1,2,3,4-tetrahydroquinolin-3-yl}-6H-thieno[2,3-b]pyrrole-5-carboxamide;

2-chloro-N-(1-{2-[(3a,6a-cis)-2,2-dimethyltetrahydro-5H-[1,3]dioxolo[4,5-c]pyrrol-5-yl]-2-oxoethyl}-2-oxo-1,2,3,4-tetrahydroquinolin-3-yl)-6H-thieno[2,3-b]pyrrole-5-carboxamide;

2-chloro-N-(1-{2-[(cis)-3,4-Dihydroxypyrrolidin-1-yl]-2-oxoethyl}-2-oxo-1,2,3,4-tetrahydroquinolin-3-yl)-6H-thieno[2,3-b]pyrrole-5-carboxamide;

2-chloro-N-{1-[2-(dimethylamino)ethyl]-2-oxo-1,2,3,4-tetrahydroquinolin-3-yl}-6 H-thieno[2,3-b]pyrrole-5-carboxamide;

2-chloro-N-{1-[(2,2-dimethyl-1,3-dioxan-5-yl)methyl]-2-oxo-1,2,3,4-tetrahydroquinolin-3-yl}-6H-thieno[2,3-b]pyrrole-5-carboxamide;

2-chloro-N-{1-[3-hydroxy-2-(hydroxymethyl)propyl]-2-oxo-1,2,3,4-tetrahydroquinolin-3-yl}-6H-thieno[2,3-b]pyrrole-5-carboxamide;

2,3-dichloro-N-{1-[(2,2-dimethyl-1,3-dioxan-5-yl)methyl]-2-oxo-1,2,3,4-tetrahydroquinolin-3-yl}-4H-thieno[3,2-b]pyrrole-5-carboxamide;

2,3-dichloro-N-{1-[3-hydroxy-2-(hydroxymethyl)propyl]-2-oxo-1,2,3,4-tetrahydroquinolin-3-yl}-4H-thieno[3,2-b]pyrrole-5-carboxamide;

2-chloro-N-(1-{2-[(2,3-dihydroxypropyl)amino]-2-oxoethyl}-2-oxo-1,2,3,4-tetrahydroquinolin-3-yl)-6H-thieno[2,3-b]pyrrole-5-carboxamide;

2-chloro-N-{1-[2-(methoxy)ethyl]-2-oxo-1,2,3,4-tetrahydroquinolin-3-yl}-6H-thieno[2,3-b]pyrrole-5-carboxamide;

2-chloro-N-[1-(cyanomethyl)-2-oxo-1,2,3,4-tetrahydroquinolin-3-yl]-6H-thieno[2,3-b]pyrrole-5-carboxamide;

2-chloro-N-{1-[(3-methyl-1,2,4-oxadiazol-5-yl)methyl]-2-oxo-1,2,3,4-tetrahydroquinolin-3-yl}-6H-thieno[2,3-b]pyrrole-5-carboxamide;

2-chloro-N-[2-oxo-1-(1H-tetrazol-5-ylmethyl)-1,2,3,4-tetrahydroquinolin-3-yl]-6 H-thieno[2,3-b]pyrrole-5-carboxamide;

2-chloro-N-(1-{2-[(methylsulphonyl)amino]-2-oxoethyl}-2-oxo-1,2,3,4-tetrahydroquinolin-3-yl)-6H-thieno[2,3-b]pyrrole-5-carboxamide;

N-{1-[(2Z)-2-amino-2-(hydroxyimino)ethyl]-2-oxo-1,2,3,4-tetrahydroquinolin-3-yl}-2-chloro-6H-thieno[2,3-b]pyrrole-5-carboxamide;

2-chloro-N-{2-oxo-1-[(5-oxo-4,5-dihydro-1,2,4-oxadiazol-3-yl)methyl]-1,2,3,4-tetrahydroquinolin-3-yl}-6H-thieno[2,3-b]pyrrole-5-carboxamide;

N-{1-[(5-amino-1,3,4-oxadiazol-2-yl)methyl]-2-oxo-1,2,3,4-tetrahydroquinolin-3-yl}-2-chloro-6H-thieno[2,3-b]pyrrole-5-carboxamide;

2-chloro-N-{1-[2-(methylthio)ethyl]-2-oxo-1,2,3,4-tetrahydroquinolin-3-yl}-6H-thieno[2,3-b]pyrrole-5-carboxamide;

2-chloro-N-{1-[2-(methylsulfinyl)ethyl]-2-oxo-1,2,3,4-tetrahydroquinolin-3-yl}-6 H-thien[2,3-b]pyrrole-5-carboxamide;

2-chloro-N-{1-[2-(methylsulfonyl)ethyl]-2-oxo-1,2,3,4-tetrahydroquinolin-3-yl}-6 H-thieno[2,3-b]pyrrole-5-carboxamide;

2,3-dichloro-N-[1-(methoxycarbonylmethyl)-2-oxo-1,2,3,4-tetrahydroquinolin-3-yl]-4H-thieno[3,2-b]pyrrole-5-carboxamide;

N-[1-(carboxymethyl)-2-oxo-1,2,3,4-tetrahydroquinolin-3-yl]-2,3-dichloro-4H-thieno[3,2-b]pyrrole-5-carboxamide;

2,3-dichloro-N-[1-(2-hydroxyethyl)-2-oxo-1,2,3,4-tetrahydroquinolin-3-yl]-4H-thieno[3,2-b]pyrrole-5-carboxamide;

2,3-dichloro-N-{1-[(2R)-2,3-dihydroxypropyl]-2-oxo-1,2,3,4-tetrahydroquinolin-3-yl}-4H-thieno[3,2-b]pyrrole-5-carboxamide;

2-chloro-N-{1-[3-(dimethylamino)-2-hydroxypropyl]-2-oxo-1,2,3,4-tetrahydroquinolin-3-yl}-6H-thieno[2,3-b]pyrrole-5-carboxamide;

2-chloro-N-{2-oxo-1-[(2-oxo-1,3-dioxan-5-yl)methyl]-1,2,3,4-tetrahydroquinolin-3-yl}-6H-thieno[2,3-b]pyrrole-5-carboxamide;

2-chloro-N-[1-(3-hydroxypropyl)-2-oxo-1,2,3,4-tetrahydroquinolin-3-yl]-6H-thieno[2,3-b]pyrrole-5-carboxamide;

2-chloro-N-{1-[3-(methylamino)-3-oxopropyl]-2-oxo-1,2,3,4-tetrahydroquinolin-3-yl}-6H-thieno[2,3-b]pyrrole-5-carboxamide;

2-chloro-N-[2-oxo-1-(2-oxobutyl)-1,2,3,4-tetrahydroquinolin-3-yl]-6H-thieno[2,3-b]pyrrole-5-carboxamide;

2-chloro-N-[1-(2-hydroxybutyl)-2-oxo-1,2,3,4-tetrahydroquinolin-3-yl]-6H-thieno[2,3-b]pyrrole-5-carboxamide;

2,3-dichloro-N-[(6S)-7-oxo-5,6,7,8-tetrahydroimidazo[1,2-α]pyrimidin-6-yl]-4H-thieno[3,2-b]pyrrole-5-carboxamide;

2,3-dichloro-N-(2oxo-1,2,3,4-tetrahydro-1,5-naphthyridin-3-yl)-4H-thieno[3,2-b]pyrrole-5-carboxamide;

2-chloro-N-(2-oxo-1,2,3,4-tetrahydro-1,7-naphthyridin-3-yl)-6H-thieno[2,3-b]pyrrole-5-carboxamide;

N-(6-fluoro-1,2,3,4-tetrahydroquinolin-3-yl)-6H-thieno[2,3-b]pyrrole-5-carboxamide; and N-(6-methoxy-1,2,3,4-tetrahydroquinolin-3-yl)-6H-thieno[2,3-b]pyrrole-5-carboxamide;

or a pharmaceutically acceptable salt or an in-vivo hydrolysable ester thereof.

13. A pharmaceutical composition which comprises a compound of claim 1, or a pharmaceutically acceptable salt or in-vivo hydrolysable ester thereof in association with a pharmaceutically acceptable diluent or carrier.

14. A method for the treatment of type 2 diabetes, insulin resistance, syndrome X, hyperinsulinaemia, hyperglucagonaemia, cardiac ischaemia, or obesity in a warm-blooded animal, comprising administering a compound of claim 1, or a pharmaceutically acceptable salt or in-vivo hydrolysable ester thereof.

15. A process for the preparation of claim 1, which process comprises:

reacting an acid of the formula (2)

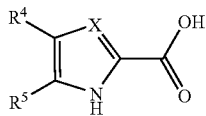 (2)

or an activated derivative thereof; with an amine of formula (3)

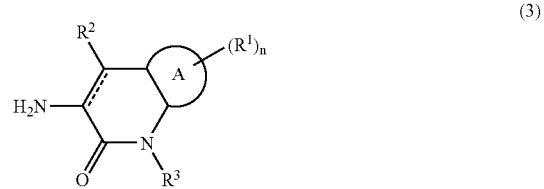 (3)

and thereafter if necessary
i) converting a compound of the formula (1) into another compound of the formula (1);
ii) removing any protecting groups; or
iii) forming a pharmaceutically acceptable salt or in-vivo hydrolysable ester.

* * * * *